US007183059B2

(12) United States Patent
Verdine et al.

(10) Patent No.: US 7,183,059 B2
(45) Date of Patent: Feb. 27, 2007

(54) SYNTHESIS OF COMPOUNDS AND LIBRARIES OF COMPOUNDS

(75) Inventors: Gregory L. Verdine, Lexington, MA (US); Milan Chytil, Cambridge, MA (US); Mary T. Didiuk, Mystic, CT (US); Tiffany Malinky, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/949,280

(22) Filed: Sep. 7, 2001

(65) Prior Publication Data

US 2002/0016010 A1    Feb. 7, 2002

(51) Int. Cl.
*G01N 33/53*   (2006.01)
*C04B 1/00*    (2006.01)

(52) U.S. Cl. ............... 435/7.1; 435/4; 435/DIG. 29; 530/333; 564/12

(58) Field of Classification Search ............... 435/4, 435/DIG. 29, 7.1, DIG. 46–58; 530/333
See application file for complete search history.

(56) References Cited

U.S. PATENT DOCUMENTS

| 5,288,514 | A | 2/1994 | Ellman ............... 427/2 |
| 5,512,131 | A | 4/1996 | Kumar et al. ........ 156/655.1 |
| 5,545,568 | A | 8/1996 | Ellman ............... 436/518 |
| 5,565,324 | A | 10/1996 | Still et al. ............ 435/6 |
| 5,639,603 | A | 6/1997 | Dower et al. .......... 435/6 |
| 5,663,046 | A | 9/1997 | Baldwin et al. ........ 435/6 |
| 5,712,171 | A | 1/1998 | Zambias et al. ....... 436/518 |
| 5,721,099 | A | 2/1998 | Still et al. ............ 435/6 |
| 5,723,598 | A | 3/1998 | Lerner et al. ......... 536/25.3 |
| 5,789,172 | A | 8/1998 | Still et al. ............ 435/6 |
| 5,811,515 | A | 9/1998 | Grubbs et al. ......... 530/330 |
| 5,929,237 | A | 7/1999 | Kahn .................. 544/279 |
| 6,348,551 | B1 * | 2/2002 | Furstner et al. ....... 526/171 |
| 6,486,324 | B2 * | 11/2002 | Cuny et al. ........... 546/183 |
| 6,794,534 | B2 * | 9/2004 | Grubbs et al. ........ 560/205 |

FOREIGN PATENT DOCUMENTS

| WO | WO 92/00091 | 1/1992 |
| WO | WO 96/40202 | 12/1996 |
| WO | WP 97/14814 | 4/1997 |
| WO | WO 97/35199 | 9/1997 |
| WO | WO 98/12156 | 3/1998 |

OTHER PUBLICATIONS

Abiko et al. "The Anti-Selective Boron-Mediated Asymmetric Aldol Reaction of Carboxylic Esters" *J. Am. Chem. Soc.* 1997, 119, 2586.
Adang et al. "Case Histories of Peptidomimetics: Progression from Peptides to Drugs" *Recued des Travaux Chimiques des Pays-Bas* 1994, 113, 63.
Amidon et al. "Absorption of Peptide and Peptidomimetic Drugs" *Annu. Rev. Pharmacol. Toxicol.* 1994, 34, 321.
Anthony et al. "Pseudo-Allylic A I,3 Strain as a Conformational Control Element: Stereoselective Syntheses of Ψ [CH2O] Pseudodipeptides" *Tet. Lett.* 1995, 36, 3821.
Babine et al. "Molecular Recognition of Protein-Ligand Complexes: Applications to Drug Design" *Chem. Rev.* 1997, 97, 1359.
Beeley et al. "Peptidomimetics and Small-Molecule Drug Design: Towards Improved Bioavailability and in vivo Stability" *TIBTECH*, Jun. 1994, 12, 213.
Blondelle et al. "Soluble Combinatorial Libraries of Organic, Peptidomimetic and Peptide Diversities" *Trends in Analytical Chemistry* 1995, 14, 83.
Bohnstedt et al. "Synthesis of E- and Z-alkene Dipeptide Isoteres" *Tet. Lett.* 1993, 34, 5217.
Borman, S. "Combinatorial Chemistry" *Chemical & Engineering; News*, Feb. 1997, 43.
Brady et al. "Reflections on a Peptide" Nature 1994, 368, 692.
Canet et al., *Chemical & Engineering News*, Jan. 6, 199 "NMR Measures Enantiome6c Excesses of Amines", p. 24.
Chakraborty et al. "Synthesis of a Peptidomimetic Analog of the Binding Domain of Rapamycin" *Chem. Lett.* 1997, 9.
Czamik, A. W. "Encoding Methods for Combinatorial Chemistry" *Curr. Opin. Chem. Biol.* 1997, 1, 60.
Dean, P. "Recent Advances in Drug Design Methods: Where Will They Lead?" *BioEssays* 1994, 16, 683.
Doemer et al. "The of Peptidomimetic Combinatc trial Libraries Through Successive Amide Alkylations" *Bioorg. & Med. Chem.* 1996, 4, 709. Synthesis.
Eichler et al. "Peptide, Peptidomimetic, and Organic Synthetic Combinatorial Libraries" *Medicinal Research Reviews* 1995, 15, 481.
Fruchtel et al. "Organic Chemistry on Solid Supports" *Angewandte Chem. Int. Ed.* 35(1); 17-42, 1996.
Gallop et al. "Applications of Combinatorial Technologies to Drug Discovery. 1. Background and Peptide Combinatorial Libraries" *J.Med. Chem.* 1994,37, 1233.
Gante, J. "Peptidomimetics-Tailored Enzyme Inhibitors" *Angew. Chem. Int. Ed. Engl.* 1994, 33, 1699.
Goodman et al. "Peptidomimetic Building Blocks for Drug Discovery" *Pure & Appl. Chem.* 1996, 68, 1303.

(Continued)

*Primary Examiner*—T. D. Wessendorf
(74) *Attorney, Agent, or Firm*—Edwards Angell Palmer & Dodge; Jeffrey D. Hsi

(57) ABSTRACT

A method of generating a compound having at least one biological activity of a peptide. The method includes identifying a biologically active peptide, providing a first monomer which contains terminal reactive moieties and at least one functionalizable group, providing a second monomer which contains terminal reactive moieties and at least one functionalizable group, and reacting first and second monomer under stereo-and/or regiochemically controlled conditions to yield a compound in which the monomers are attached by way of terminal reactive moieties.

26 Claims, 49 Drawing Sheets

OTHER PUBLICATIONS

Hagihara et al. "Vinylogous Polypeptides: An Alternative Peptide Backbone" *J. Am. Chem. Soc. 1992*, 114, 6568.

Heathcock, et al. "1, 4- and 1, 5-Stereoselection by sequenetial aldol addition to alpha, beta-unsaturated aldehydes followed by Claisen rearrangement. Application. to total synthesis of the vitamin E side chain and the archaebacterial C40 diol" J. Org. *Chem.* 53:1922-42, 1988.

Hirschmann et al. "De Novo Design and Synthesis of Somatostatin Non-Peptide Peptidomimetics Utilizing β-D-Glucose as a Novel Scaffolding" *J. Am. Chem. Soc. 1993*, 115, 12550.

Hirschmann R. "Medicinal Chemistry in the Golden Age of Biology: Lessons from Steroid and Peptide Research" *Angew. Chem. Int. Ed Engl. ,1991*, 30, 1278.

Hruby et al. "Synthesis of Oligopeptide and Peptidomimetir Libraries" *Curr. Opin. Chem. Biol. 1997*, 1, 114.

Ibukaet al. "A Stereoselective Synthesis of (E)-Alkene Dipeptide Isoteres via Organocyanocopper-Lewis Acid Mediated Reaction" *J. Org. Highly Chem. 1991*, 56, 4370.

Kahn et al. "The Design and Synthesis of a Nonpeptide Mimic of an Immunosuppressing Peptide" *Tet. Lett.* 1986, 27, 4841.

Kaltenbronn et al. "Renin Inhibitors Containing Isosteric Replacements of the Amide Bond Connecting the P3 and P2 Sites" J. *Med. Chem.* 1990, 33, 838.

Kazmierski et al. "Recent Advances in the Design and Synthesis of Small-Molecule Mimetic Drugs" *TIBTECH*, Jun. 1994, vol. 12, p. 216.

Lam et al. "A New Type of Synthetic Peptide Library for Identifying Ligand-Binding Activity" *Nature* 1991, 354, 82.

Marshall et al. "A Hierarchical Approach to PeptidomimeticDesign" *Tetrahedron* 1993, 49, 3547.

Masse et al. "Asymmetric C-N Bond Constructions via Crotylsilane Addition Reactions: A Stereocontrolled Route to Dipeptide Isosteres" . J.*Am. Chem. Soc.* 1997, 119, 6040.

Miller et al. "Synthesis of Conformationally Restricted Amino Acids and Peptides Employing Olefin Metathesis" *J. Am. Chem. Soc.* 1995, 117, 5855.

Miller et al. "Application of Ring Closing Metathesis to the Synthesis of Rigidified Amino Acids and Peptides" *J. Am. Chem. Soc.* 1996, 118, 9606.

Moody et al. "A New Approach to Peptide Synthesis" *Chem. Commun.* 1997, 2391.

Norman et al. "Stereoselective Synthesis of Novel Methylen c Ether Dipeptide Isosteres" *Tet. Lett* 1995, 36, 4151.

Oliyai, R. "Prodrugs of Peptides and Peptidomimetics for Improved Formulation and Delivery" *Adv. Drug Del. Rev.* 1996, 19, 275.

Ostresh et al. "Generation and Use of Nonsupport-Bound Peptide and Peptidomimetic Combinatorial Libraries" *Methods in Enzymology*1996, 267, 220.

Palazzi et al. "Improved Enantioselective Synthesis of Anti-α-methyl-β-hydroxyesters through TiCl4- PPh3 Mediated Aldol Condensation" *Tet.Lett.* 1986, 27,1735.

Rutjes et al. "Ruthenium-Catalyzed Ring Closing Olefin Metathesis of Non-Natural α-Amino Acids" *Tet. Lett.* 1997, 38, 677.

Schuster et al. "Olefin Metathesis in Organic Chemistry" *Angew. Chem. Int. Ed. Engl.* 1997, 36, 2036.

Schuster et al. "Ruthenium-Catalyzed Metathesis of Polymer-Bound Olefins" *Angew. Chem. Int. Ed. Engl.* 1996, 35, 1979.

Simon, et al. "Peptoids: A Modular Approach to Drug Discovery" Proc. Nat. Acad. Sci. USA 89:9367-71, 1992.

Smith et al. "The Design and Synthesis of 2,5-Linked Pyrrolinones. A Potential Non-Peptide Peptidomimetic Scaffold" Bioorg. & *Med. Chem.* 1996, 4, 1021.

Terrett, et al. "Combinatorial Synthesis—the Design of Compound Libraries and Their Application to Drug Discovery" *Tetrahedron Ltrs.* 51(30):8135-73, 1 9955.

Thaisrivongs, et al. "Renin inhibitors. Design of Arigiotensinogen transition-state analogues containing novel (2R, 3R, 4R, 5S -5-amino-3, 4-dihydroxy -2-isopropyl-7-me thyloctanoic acid" *J. Med. Chem.* 30:976-82, 1987.

Thompson et al. "Synthesis and Applications of Small Molecule Libraries" *Chem. Rev.* 96(1):555-600, 1996.

Virgilio et al. "Synthesis and Evaluation of a Library of Peptidorrlimetics Based Upon β-Turn" *Tetrahedron* 1997, 53, 6635.

Wai et al. "An Efficient Synthesis of γ-Aikylated E-Olefin Dipeptide Isosteres" *Tet. Lett.* 1995, 36, 3461.

Wiley et al. "Peptidomimetics Derived from Natural Products" *Medicinal Research Reviews* 1993, 13, 327.

Yoshimitsu, et al. "Application of newly developed anti-selective aldol methodology: synthesis of C6-C13 and C19-C28 fragments of mivakolide" J. Org. *Chem.* 62:8978-9 1997.

Zuckerman, et al. "Efficient Method for the Preparation of Peptoids Oligo (NU-Substituted Glycines) by Sumonomer Solid-Phase Synthesis" *J. Am. Chem. Soc.* 114(26):10646-7, 1992.

Zuckerman, R. "The Chemical Synthesis of Peptidomimetic libraries" *Curr. Opin. Struc. Biol.* 1993, 3, 580.

\* cited by examiner

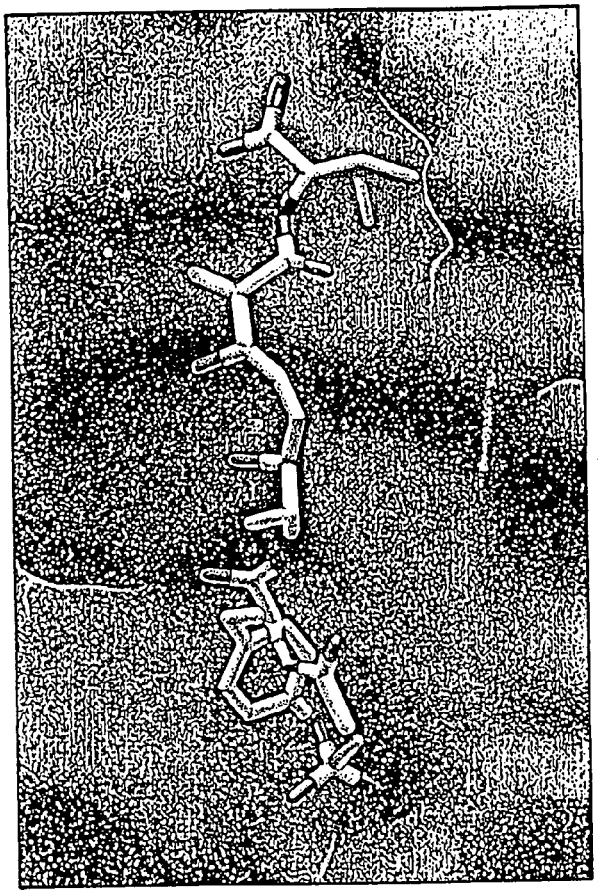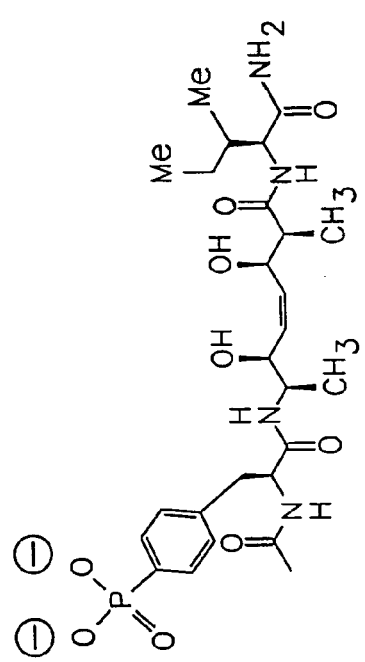
FIG. 26

SYNTHESIS OF COMPOUNDS AND LIBRARIES OF COMPOUNDS

PRIORITY INFORMATION

This application claims priority to co-pending U.S. patent application Ser. No. 09/273,597, entitled "Synthesis of Compounds and Libraries of Compounds", filed Mar. 22, 1999, which claims priority to U.S. provisional application 60/079,035, entitled "Synthesis of Compounds with Peptide Characteristics", filed Mar. 23, 1998, the entire contents of both which are incorporated herein by reference.

BACKGROUND OF THE INVENTION

The important biological roles that peptides play as hormones enzyme inhibitors, substrates, neurotransmitters, and neuromediators has led to the widespread use of peptides in medicinal chemistry as therapeutic agents. Through binding to receptors or enzymes, peptides Marc are able to influence cell-cell communication and control vital cell functions such as metabolism, immune defense and reproduction. (Babine et al., *Chem. Rev.* 1997, 97, 1359) Unfortunately, the utility of peptides as drugs is severely limited by several factors, including their rapid degradation by peptidases under physiological conditions, their poor cell permeability, and their lack of binding specificity resulting from conformational flexibility.

In response to these unfavorable characteristics of peptide drugs, many research groups have developed strategies for the design and synthesis of chemical compounds, known as "peptidomimetics", in which sensitive peptide moieties are removed and replaced with more robust functionalities. In particular, researchers have sought to improve peptide stability and cell permeability by replacing the amide functionality with groups such as hydroxyethylene, (E)-alkenes, carba groups and phosphonamide groups (Gante, J., *Angew. Chem. Int. Ed. Engl.* 1994, 33, 1699–1720, and references cited therein).

In most cases, these peptidomimetic compounds have been prepared one at a time. A few researchers have also attempted to design combinatorial strategies to produce peptidomimetic libraries (Boger, D, WO 96/03424; Ellman, J., U.S. Pat. No. 5,545,568; Simon. R. et al., *Proc. Natl. Acad. Sci. USA* 1992, 89, 9367; Bartlett et al.,i Proc. Natl. Acad. Sci. USA 1992, 89, 9367). Unfortunately, these efforts are often limited by lack of stereochemical complexity and control, and/or by restricted ability to substitute base molecules. Also, existing peptidomimetic strategies generally rely on a fixed structure to mimic the peptide bond, and do not allow subsequent modification and diversification of this structure.

There remains a need to develop a synthetic strategy capable of producing complex. highly diversified libraries of compounds that can act as peptidomimetics. There is a particular need for methods and compounds that allow significant stereochemical control and functional group diversity in the production of such libraries. Furthermore, because of the importance of stereochemical complexity in the synthesis of these and other libraries, there also remains a need for the development of stereodiverse compounds and libraries of compounds.

SUMMARY OF THE INVENTION

The present invention provides a system for the production of chemical compounds that are capable of mimicking structural and/or functional properties of peptides. The inventive system allows simultaneous production of multiple complex compounds, and provides for significant stereochemical and regiochemical control, as well as functional group diversity. While the prior art describes attempts to reproduce a particular peptide structure, the present invention provides a broad new approach to the production of compounds with certain structural and/or functional properties characteristic of peptides. The term "peptidomimetic", therefore, when used herein in the context of the present invention, encompasses more expansive concepts than are found in the prior art. In addition to providing a broad new approach to the production of compounds with certain structural and/or functional characteristics of peptides, the present invention teaches a broad new approach for the synthesis of libraries of compounds having stereochemistry as a diversity element.

According to the present invention, both the structure replacing the peptide bond and that replacing the peptide functional group can be modified and diversified. Furthermore, the present invention enables not only the diversification of chemical structure and the synthesis of compounds having peptide characteristics, but also enables the synthesis of stereodiverse compounds. The present invention therefore can be seen as providing methods and compounds that transform peptide functionalities into alternative chemical structures and stereoisomers of these chemical structures. In one sense, the invention constitutes a system for "morphing" peptides into other compounds.

In one aspect, the present invention provides methods for producing collections of peptidomimetic compounds. In certain preferred embodiments, these methods involve (1) providing two diversifiable monomers containing terminal reactive moieties; (2) reacting the monomers under conditions that allow for the control of stereochemistry as well as chemoselectivity, and (3) generating diversifiable, isolable compounds or libraries of compounds. In other preferred embodiments, the methods involve (1) providing one diversifiable monomer containing terminal reactive moieties; (2) reacting the monomer with a reagent under conditions that allow for the control of stereochemistry as well as selectivity, and (3) generating diversifiable isolable compounds or libraries of compounds.

As discussed, the present invention provides a system for the stereochemical control of the synthesis of compounds and libraries of compounds. As will be appreciated by one of ordinary skill in the art, this aspect is not limited to the synthesis of libraries of peptide mimics. Rather, the present invention encompasses the broader concept of providing any collection of chemical compounds having stereodiversity. Thus, in another aspect, the present invention provides methods for the generation of compounds and libraries of compounds, peptidomimetics and non-peptidomimetics alike, having stereochemical diversity. This method involves the steps of (1) selecting desired synthetic precursors having a predefined stereochemical relationship; (2) reacting the synthetic precursors so that a compound having a specific stereochemistry is obtained; and (3) repeating these steps of selecting and reacting until a desired library of compounds having stereochemical diversity is obtained. In preferred embodiments, a library of compounds having only diversity of stereochemistry is provided. For these embodiments, it is particularly preferred that at least 4 stereoisomers are provided, more particularly preferred that at least 8 stereoisomers are provided, and most particularly preferred that at least 16 stereoisomers are provided. In other preferred embodiments, a library of compounds having structural diversity and stereochemical diversity is provided. Thus, for each compound having a specific structural formula, it is particularly preferred that for each structure at least 4 stereoisomers are provided, more particularly preferred that at least 8 stereoisomers are provided, and most particularly preferred that at least 16 stereoisomers are provided.

The present invention also provides methods of preparing and screening libraries of compounds generated to mimic desired functional and/or structural aspects of a particular peptide or portion thereof. As such, the invention provides methods for "morphing" peptides into alternate chemical compounds.

In yet another aspect, the invention provides various chemical compounds useful for production of complex peptidomimetic libraries. These compounds may be diversified at the level of functional group units, monomer units, segment units, and biomolecule units. Furthermore, each of these units may be diversified structurally, i.e., by functional group diversification, or may be diversified stereochemically.

DESCRIPTION OF THE DRAWING

FIG. 26 depicts a model structure of the binding of a morphed peptide to a $SH_2$ domain.

DEFINITIONS

Figure 1:
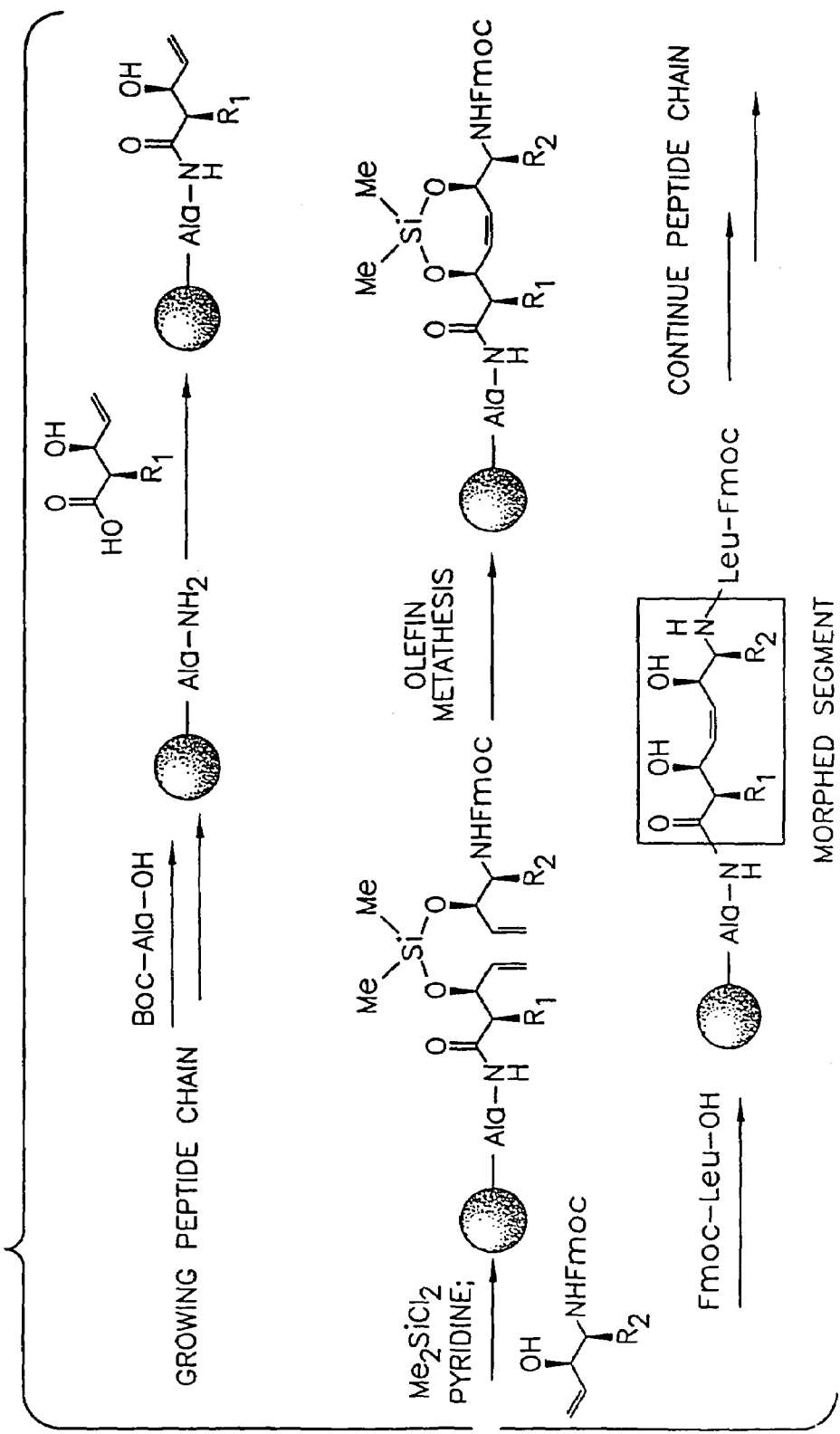
FIG. 1 depicts the Peptide Morphing strategy of the present invention.

"Peptidomimetic": The term "peptidomimetic", as used herein, refers to a chemical compound that, at least in part, mimics one or more structural or functional properties of a peptide. As discussed above, the prior art definition of peptidomimetic focuses on compounds in which one or more of the characteristic chemical moieties of a peptide is substituted with alternative functional groups. The present invention provides a broader concept of peptidomimetic, describing a system for producing a wide variety of chemical compounds that may have one or more structural or functional aspects of biologically active peptides. That is, for the purposes of the present invention, a peptidomimetic does not necessarily refer to a compound that per se imitates the properties of a peptide, but can also refer to a compound in which a segment unit replacement of the amide functionality, which bears no structural relationship to a peptide functionality, is capable of interacting with a biological receptor or ligand with desired specificity. To give but a few specific examples, peptidomimetics include, but are not limited to compounds in which the amide bond of a peptide is replaced with alkene, hydroxyethylene or carba functionalities. Peptidomimetics also include compounds in which the α—CH group is replaced with aza, C-alkyl, or bora functionalities, among others.

"Combinatorial Library": The term "combinatorial library", as used herein, refers to a collection of compounds produced in a manner that allows "segment units", "functionality units", "monomer units", "biomolecule units", or any combination thereof, to be varied in a systematic fashion. The segment unit may be generated from any compatible reaction between monomers (or upon a monomer) that results in a replacement of the amide functionality with any other functionality. The functionality units may be varied on individual monomers, or after monomers have been joined together. These functionality units may be present within the segment unit of the joined monomers, or may be present at other sites within the monomers.

"Biomolecules": The term "biomolecules", as used herein, refers to molecules (e.g., proteins, amino acids, nucleic acids, nucleotides, carbohydrates sugars, lipids, etc.) that are found in living cells in nature.

"Monomer unit": The term "monomer unit", as used herein, refers in one aspect to a molecule that can be joined together to form another molecule or set of molecules, such as a set of oligomers or polymers. In another aspect "monomer unit", as used herein, refers to a molecule that can be diversified at particular sites on the monomer unit. More particularly, the present invention refers to a monomer that is characterized in that it contains reactive moieties available for diversification and optionally is characterized by the presence of a reactive moiety that allows linkage of multiple individual monomers by way of a segment unit functionality.

"Diversity element": The term "diversity element", as used herein, refers to structural (i.e., functional group diversity), stereochemical, diastereochemical, and/or regiochemical diversity in a particular compound. As will be appreciated by one of ordinary skill in the art, the present invention provides for the synthesis of compounds and libraries of compounds having any of these diversity elements alone or in combination with one or more of the other diversity elements.

"Stereoisomer": The term "stereoisomer", as used herein, refers to a structure of the same constitution as another structure, differing only in the spatial arrangement. Stereoisomers are described by specifying their topology and the nature of their relationship to other stereoisomers of the same constitution.

"Enantiomer": The term "enantiomer", as used herein, refers to a stereoisomer that is related to another stereoisomer as an object and its mirror image.

"Diastereomer": The term "diastereomer", as used herein, refers to a stereoisomer that is related to another stereoisomer in a manner other than as an object and its mirror image. For example, one stereogenic center relative to another stereogenic center is different for diastereomers. Diastereomers differ from one another both in physical properties and in chemical reactivities. For example, different diasteriomers generally have different melting points, boiling points, and solubility characteristics.

"Stereoselective Reaction": The term "stereoselective reaction" refers to a chemical reaction in which one of the stereoisomeric products is formed in excess.

"Enantioselective Reaction": The term "enantioselective reaction" refers to a chemical reaction in which one of the enantiomeric products is formed in excess.

"Diastereoselective Reaction": The term "diastereoselective reaction" refers to a reaction in which only one of the diastereomeric products is formed in excess, or one in which the major product is diastereomerically pure.

"Regioselective Reaction": The term "regioselective reaction" refers to a reaction in which an unsymmetrical alkene gives a predominance of one of the two possible addition products. The reaction is regiospecific if one of the products is formed exclusively.

DETAILED DESCRIPTION OF CERTAIN PREFERRED EMBODIMENTS

As discussed above, the present invention provides methods and compounds related to production of complex libraries of chemical compounds with certain structural and/or functional characteristics of peptides. In addition to providing compounds and libraries of peptide-like compounds and methods for their syntheses, the present invention, in a broader aspect, provides for the generation of chemical libraries of peptidomimetics and non-peptidomimetics alike, having stereoisomerism as a diversity element.

In one particularly preferred embodiment, as shown in FIG. 1, the inventive reactions involve steps of (1) providing at least two monomer compounds, each of which has at least two terminal reactive moieties; and (2) reacting the monomers with one another, under conditions that allow for the control of stereochemistry as well as chemoselectivity, so that they become linked together at one of their reactive moieties and generate a segment unit, and (3) generating diversifiable isolable compounds or libraries of compounds. Typically, each monomer contains multiple reactive moieties, and additional reactions are performed to functionalize these moieties either before or after the monomers are linked to one another, so that highly complex libraries are produced.

In another particularly preferred embodiment, the inventive reactions involve steps of (1) providing at least one monomer compound, which has at least two terminal reactive moieties; (2) reacting the monomer with a reagent that allows for the control of stereochemistry as well as chemoselectivity, and (3) generating diversifiable isolable compounds or libraries of compounds with characteristics reminiscent of peptides.

One advantage of the inventive synthetic system is that it allows simultaneous production of a large number of complex peptidomimetic compounds under conditions of controlled stereo- and regio-selectivity. Preferred peptidomimetic compounds produced according to the present invention contain both peptide bond and functional group substitutions when compared with peptides. Thus, the present invention represents a broadening of the conception of peptidomimetics. In fact, another advantage of the present system is that these substitutions are not necessarily limited to compounds that represent structural mimics of peptides, as might be found in the prior art. Instead, the inventive system, through a segment unit replacement, enables the maximization of the diversification of structures. The invention therefore enables the discovery of heretofore unanticipated interactions of compounds, that bear little or no structural relation with peptides, with biological receptors or ligands.

As will be appreciated by one of ordinary skill in the art, the method of the present invention and the ability to control the specific stereochemistry has a broader context than the immediate application to peptidomimetics. Rather, the present invention also provides for the generation of libraries having stereodiversity. Thus, in another aspect, the present invention provides methods for the generation of compounds and libraries of compounds, peptidomimetics and non-peptidomimetics alike, having stereochemical diversity. This method involves the steps of (1) selecting desired synthetic precursors having a predefined stereochemical relationship: (2) reacting the synthetic precursors so that a compound having a specific stereochemistry is obtained; and (3) repeating these steps of selecting and reacting until a desired library of compounds having stereochemical diversity is obtained. In preferred embodiments, a library of compounds having only diversity of stereochemistry is provided. For these embodiments, it is particularly preferred that at least 4 stereoisomers are provided, more particularly preferred that at least 8 stereoisomers are provided, and most particularly preferred that at least 16 stereoisomers are provided. In other preferred embodiments, a library of compounds having structural diversity and stereochemical diversity is provided. Thus, for each compound having a specific structural formula, it is particularly preferred that for each structure at least 4 stereoisomers are provided, more particularly preferred that at least 8 stereoisomers are provided, and most particularly preferred that at least 16 stereoisomers are provided.

Various characteristics of the monomers and reactions utilized in preferred embodiments of the present invention are discussed in more detail below; certain examples of inventive reactions and compounds are also presented.

Monomers

Figure 2:
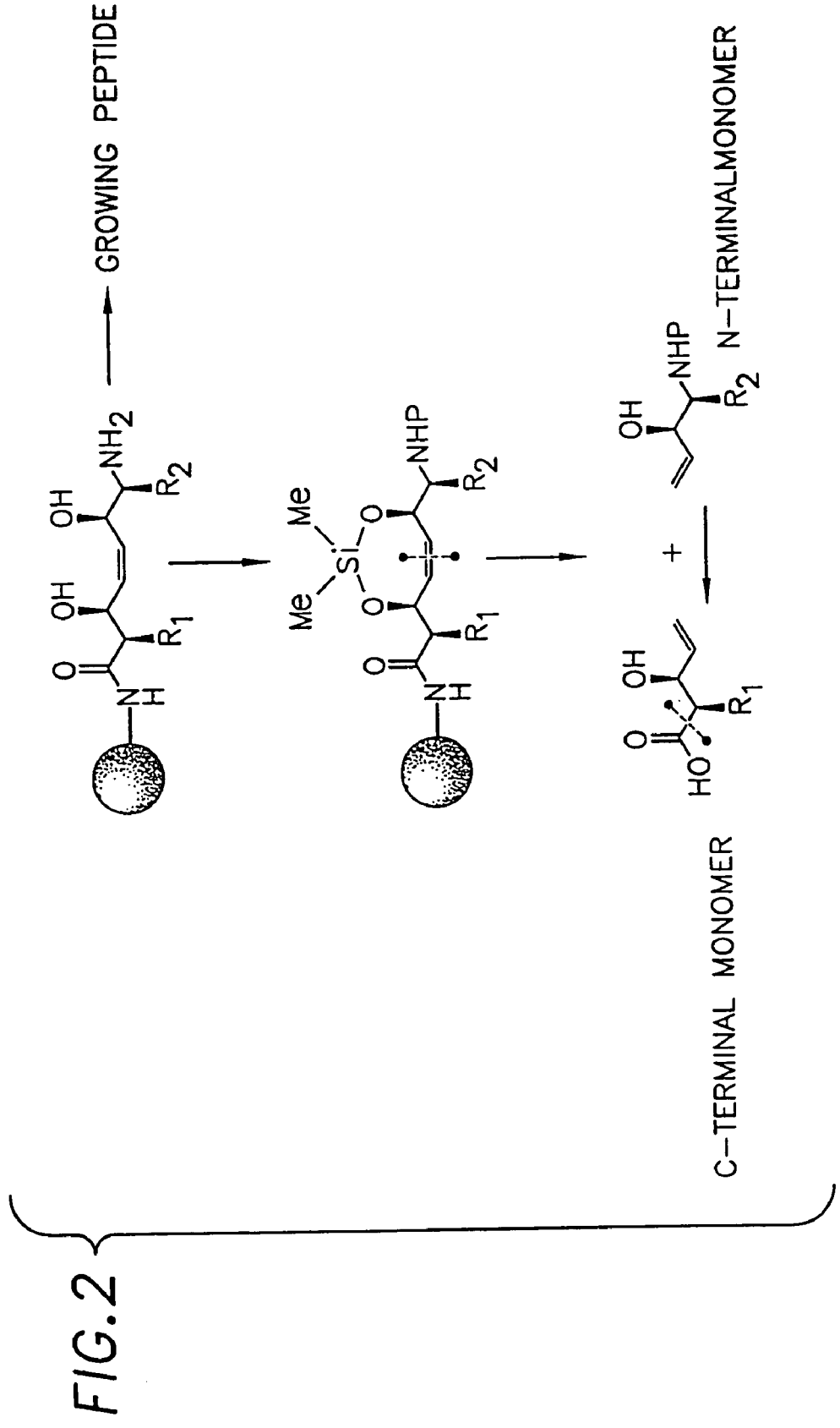
FIG. 2 depicts a retrosynthetic analysis of a preferred structure of the present invention.

As mentioned above, preferred embodiments of the invention utilize either a single monomer or at least two monomers. FIG. 2 depicts the retrosynthetic analysis of a preferred diversifiable peptidomimetic core, in which two monomers are used to generate the desired structure. Each monomer is characterized either by the presence of a reactive moiety that facilitates the linkage of the monomers to one another by way of a segment unit, or by the presence of a reactive moiety that facilitates the reaction of the monomers with chemical reagents. Each monomer preferably also contains additional reactive moieties available for diversification, so that the peptidomimetic compounds produced according to the present invention can be diversified both at the level of the segment unit structure and at the level of functional groups. Preferably, each monomer contains at least one terminal reactive moiety that allows the monomer to be linked to a biomolecule. In particularly preferred embodiments, each monomer contains a moiety available for linkage to a peptide, so that the inventive peptidomimetic compounds can readily be embedded within a peptide chain.

The monomers utilized in accordance with the present invention are selected to allow for significant control of the stereo- and regio-chemistry of the reactions that they undergo. Furthermore, as will be appreciated by those of ordinary skill in the art, and is discussed in more detail below, in embodiments utilizing at least two monomers, each monomer is selected to react with the other monomer being employed. Thus, the chemical nature of the moiety on the first monomer that is available for linkage to the second monomer places constraints on the nature of the acceptable second monomer moiety and therefore limits the selection of the second monomer, and also limits the resulting stereoselectivity.

In certain preferred embodiments of the invention, at least one monomer contains a reactive moiety available for linkage to the solid phase. Such linkage may be direct or indirect. For example, the monomer may be linked to another molecule, preferably a biomolecule (and most preferably a peptide) that is itself linked to the solid phase. Methods of linking compounds to the solid phase are known in the art and a variety of methods may be employed in the present invention. (See, for example, Brown, "Recent Developments in Solid-Phase Organic Synthesis" *Contemporary Organic Synthesis,* 1997, p. 216; Hiroshige et al., Tet. Lett. 1995, 36, 4567; Rotella, D., *J. Am. Chem. Soc.* 1996, 118, 12246 and references cited therein.)

Figure 3:
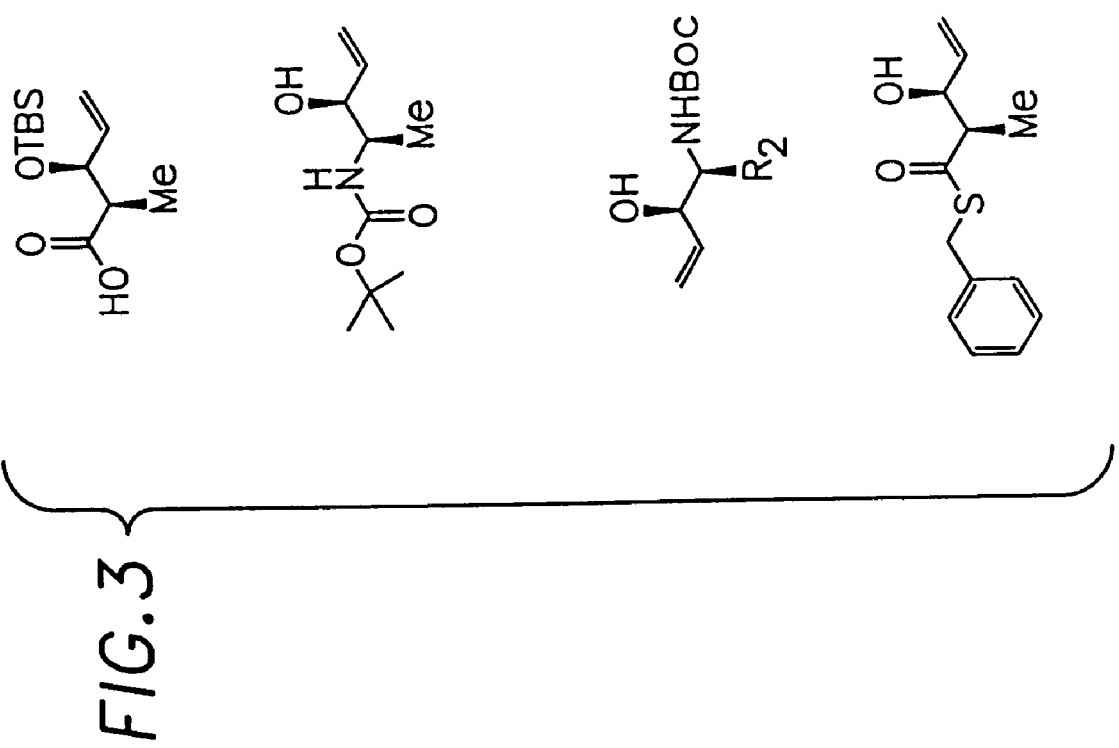
FIG. 3 depicts certain preferred monomers having a syn relationship between the allylic alcohol and the functional group.

The monomers utilized in the present invention are preferably easily synthesized, in high yields with high diastereo- and enantioselectivity. Examples of certain preferred monomers having a syn relationship between the allylic alcohol and the functional (R) group are depicted in FIG. 3. In addition to providing monomers having a syn relationship, the present invention provides monomers having an anti relationship as depicted in Examples 13–29. Thus, the ability to provide monomers having all possible stereoisomers enables the synthesis of compounds and libraries of compounds having significant stereodiversity. Formula 50 below, depicts a general scheme of a particularly preferred embodiment of the present invention for the synthesis of inventive compounds and libraries of compounds:

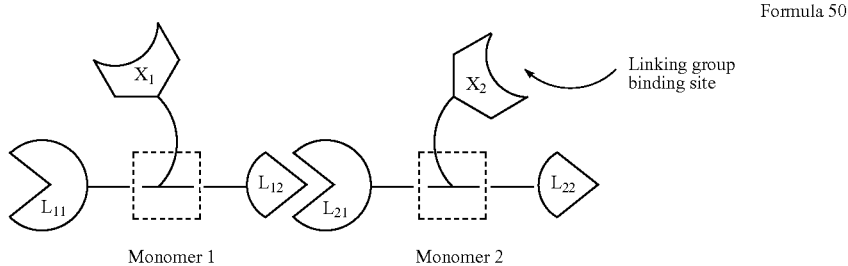

Formula 50

As depicted, each monomer contains first ($L_{11}$ and $L_{21}$) and second ($L_{12}$ and $L_{22}$) terminal functionalities capable of either (1) linking to another monomer in an inter- or intramolecular fashion; (2) being immobilized on the solid support, or (3) attaching to other amino acids or peptides. Each monomer also contains an optional linking group binding site ($X_1$ or $X_2$) that can be employed to link the monomers together in an intramolecular fashion. Furthermore, any or all of the base monomer structures, the terminal functionalities, and the linking group binding sites may contain reactive sites available for further diversification, as is discussed in more detail below.

As will be appreciated by those of ordinary skill in the art, a wide variety of first and second terminal functionalities may be employed in accordance with the present invention. As will also be appreciated, the selection of these functionalities for each monomer will depend on the nature of the moiety with which each functionality is to react. Terminal functionalities that may be employed include but are not limited to amines, carboxylic acids, halogenated aromatics for transition metal catalyzed cross coupling reactions, terminal aldehydes for pinacol couplings, terminal alkynes for hydrozirconation, and terminal alkenes for olefin metathesis and nucleophilic addition. FIGS. 4, 5, 6, 7, 8 and 9 show the preferred cross-coupling, pinacol coupling, tandem aldol/Curtius rearrangement, hydrozirconization, nucleophilic addition, and NHK (Nozaki-Hiyama-Kishi (Fürstner et al., J. Am. Chem. Soc. 1996, 118, 12349)) coupling, respectively.

Figure 10:
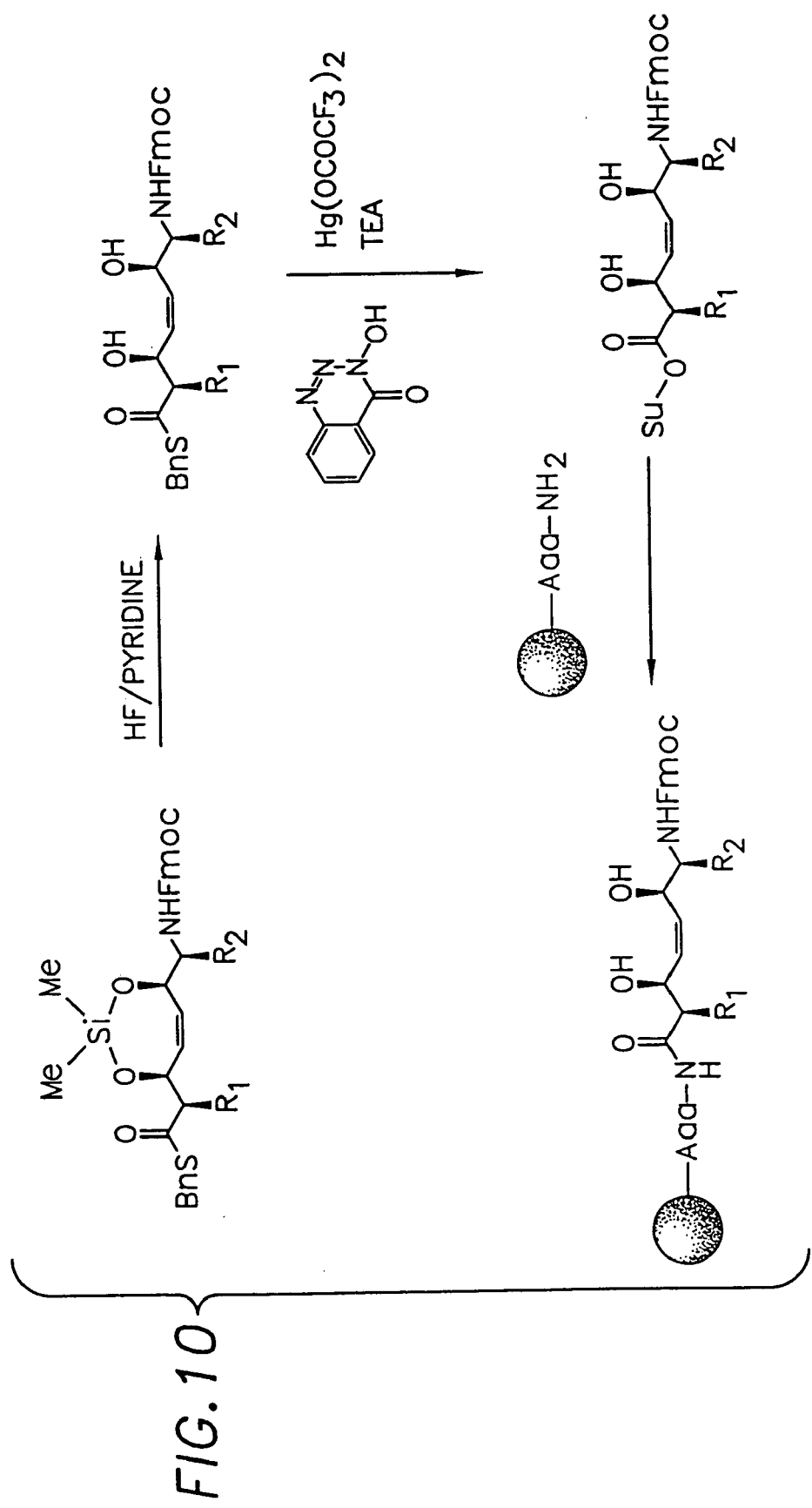
FIG. 10 depicts attachment of a morphed segment to the resin.

In one particularly preferred embodiment, the second terminal functionality ($L_{i2}$) of the first monomer and the first terminal functionality ($L_{21}$) of the second monomer are each alkenes, selected to be capable of reacting with one another. In another particularly preferred embodiment, one or both of the first terminal functionality ($L_{11}$) of the first monomer and the second terminal functionality ($L_{22}$) of the second monomer is either an amine or carboxylic acid capable of further reacting with amino acids. In yet another preferred embodiment, at least one of the first terminal functionality ($L_{11}$) of the first monomer and the second terminal functionality ($L_{22}$) of the second monomer is selected for linkage to a solid phase resin. FIG. 10 depicts the attachment of the diversifiable peptidomimetic structure of the present invention to the resin.

Those of ordinary skill in the art will appreciate that any of a variety of linking group binding sites may be employed in accordance with the present invention, so long as the binding site can be reacted with a linking reagent to add a linking group to the monomer. The linking group then reacts to link the first and second monomers to one another.

Representative linking reagents include sulfonyl chloride, dimethyl dichlorosilane, diisopropylamino chlorophosphoramidite and metals (such as boron and titanium) that are capable of temporary binding as a linker. One of ordinary skill in the art will realize that other linking reagents can be employed to generate mixed carbonates (R and R'), carbamates, disulfides, ureas, acetals, ortho esters, phosphates and oxides as linking groups.

Linking group binding sites can include any functionality capable of reaction with the selected linking reagent. Preferably, the linking group binding site comprises a carbon, oxygen, nitrogen, or sulfur atom, for example a hydroxyl, amino, or thiol group, through which the linking group becomes attached to the monomer. Formula 51, below, depicts one particular preferred embodiment of a monomer for use in the present invention, in which $L_{11}$ and $L_{12}$ preferably each comprise the same or different terminal reactive moiety selected from the group consisting of hydrogen, protecting group, alkene, alkyne, amine, carboxylic acid, halogenated aromatic, aldehyde and vinyl halide; $R_1$, $R_2$ and $R_3$ are preferably selected from the group consisting of hydrogen, alkyl, aryl, phenoxy, methoxy, halide, methylene cyclohexyl, benzyl, heteroaryl, aryloxy, carboxyl, carboxalkyl, carboxaryl, arylalkyl, thio and hydroxyl; X preferably comprises a functional moiety selected from the group consisting of carboxyl, amino, gem-dialkyl, and methylene; $X_1$ preferably comprises a functionality containing nitrogen, oxygen, sulfur or carbon; and L preferably comprises a group, including but not limited to mixed carbonates (R and R'), carbamates, disulfides, ureas, acetals, ortho esters, phosphates and oxides, produced by reaction with a linking reagent.

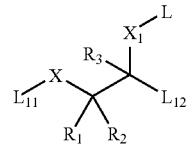

Formula 51

Formula 52 depicts the first monomer of Formula 51 after linkage to a second monomer. In a particularly preferred embodiment, the two monomers connected by the linking group are in a syn relationship to each other. Preferably $L_1$, $L_{12}$, $L_{21}$, and $L_{22}$ each comprise the same or different terminal reactive moiety selected from the group consisting of hydrogen, protecting group, alkene, alkyne, amine, carboxylic acid, halogenated aromatic, aldehyde and vinyl halide; $R_1$, $R_2$ and $R_3$ are preferably selected from the group consisting of hydrogen, alkyl, aryl, phenoxy, methoxy, halide, methylene cyclohexyl, benzyl, heteroaryl, aryloxy, carboxyl, carboxalkyl, carboxaryl, arylalkyl, thio and hydroxyl; $X_3$ and $X_4$ each preferably comprises a functional moiety selected from the group consisting of carboxyl, amino, gem-dialkyl, and methylene; $X_1$ and $X_2$ preferably each comprise a functionality containing nitrogen, oxygen, sulfur or carbon; and L preferably comprises a group, including but not limited to mixed carbonates (R and R'), carbamates, disulfides, ureas, acetals, ortho esters, phosphates and oxides, produced by reaction with a linking reagent. As will be appreciated by one of ordinary skill in the art, these monomers can be attached to a solid support unit, or may also be attached to a biomolecule or a polymer. The further treatment of such linked monomers is discussed more in detail below.

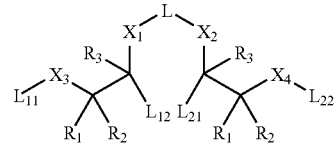

Formula 52

Figure 11:
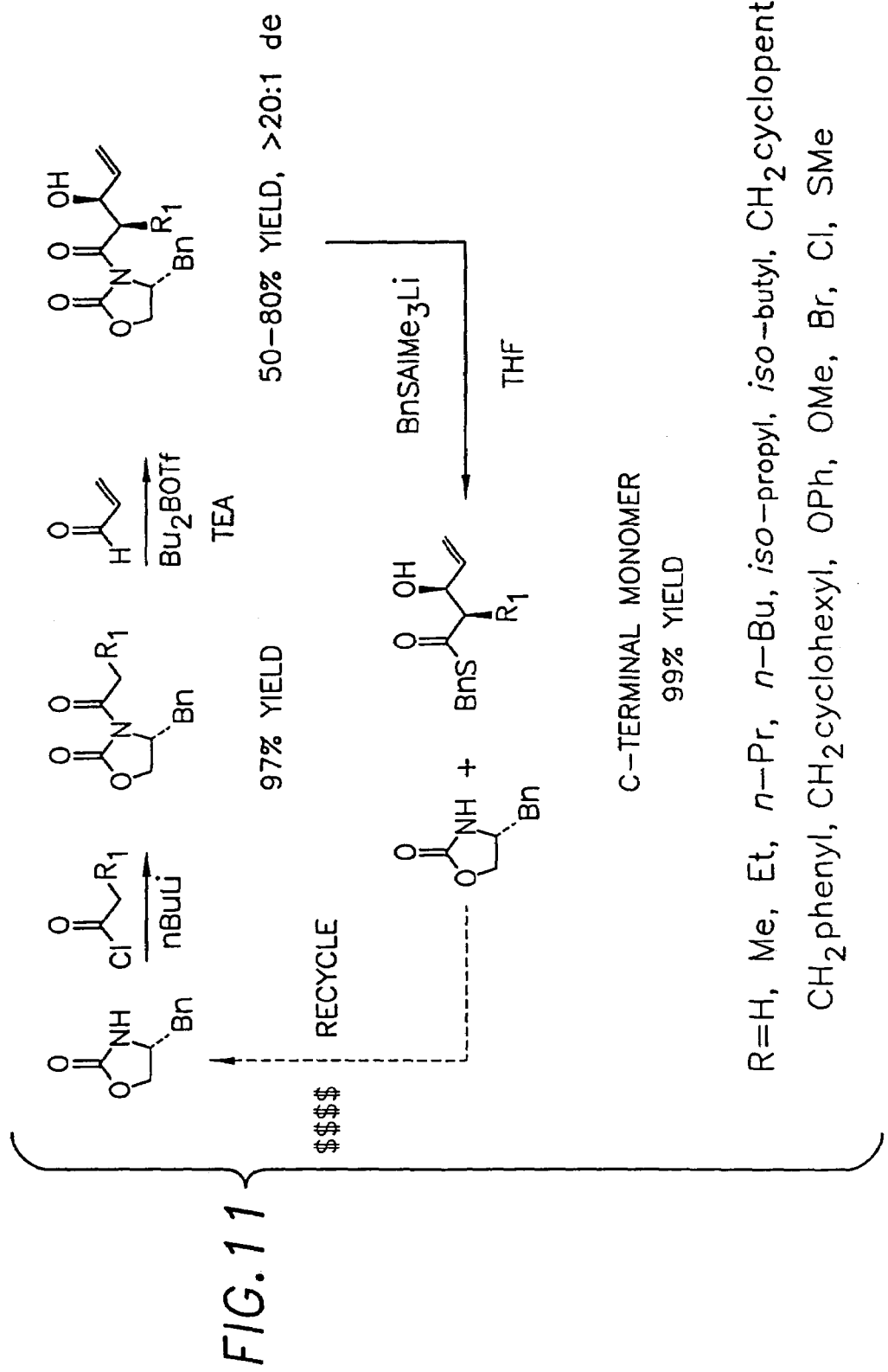
FIG. 11 depicts synthesis of the C-terminal (first) monomer.
Figure 12:
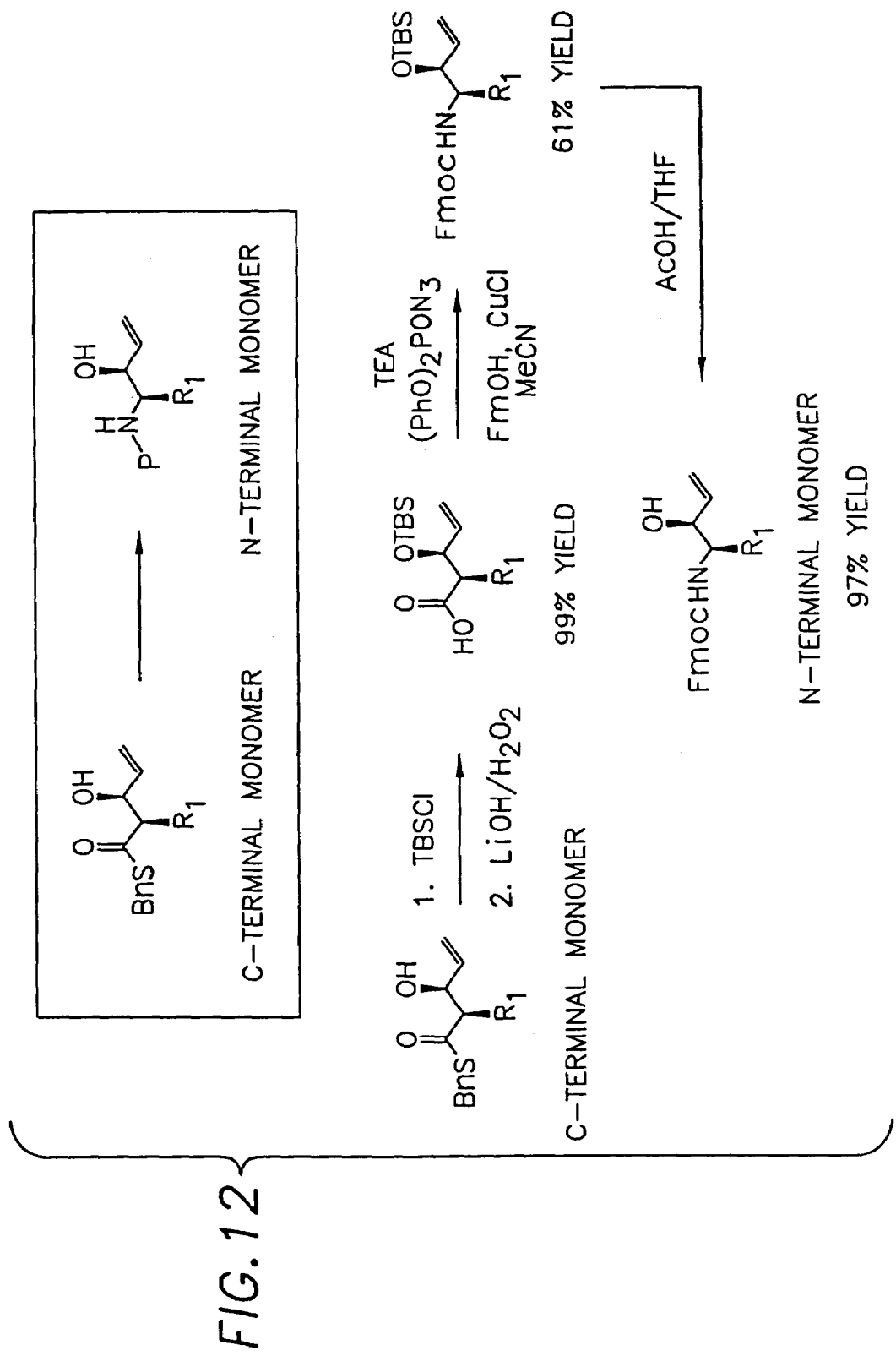
FIG. 12 depicts the synthesis of the N-terminal (second) monomer.
Figure 13:
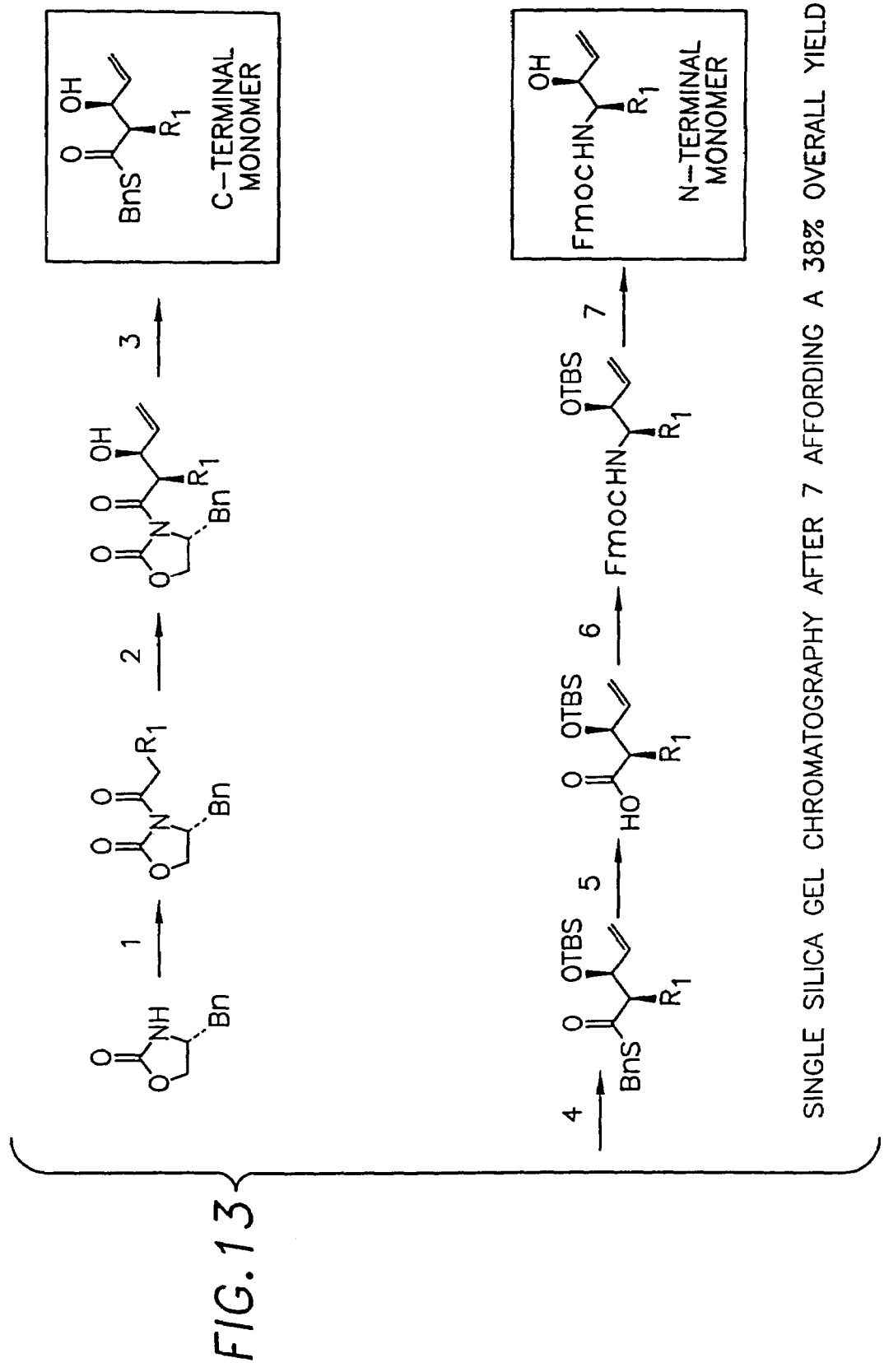
FIG. 13 depicts a convergent and efficient synthesis of monomers.

In one particularly preferred embodiment of the present invention, the first and second monomers are structurally related to one another so that the second monomer can be produced by chemical conversion of the first. For example, FIGS. 11, 12 and 13 depict preferred embodiments of the present invention in which first and second monomers (depicted as C-terminal and N-terminal monomers, respectively) are synthesized convergently using known Evans' aldol chemistry (Evans et al., J. Am. Chem. Soc. 1982, 104, 1737).

These particular monomers are especially useful because they can be obtained in high yield. Furthermore, the monomer is capable of extensive diversification. For example, R can be, but is not limited to, methyl, ethyl, n-propyl, iso-propyl, cyclopentyl, phenoxy, methoxy, bromide, and methylene cyclohexyl, benzyl, chloride, carboxyalkyl, carboxaryl, arylalkyl, thio, hydroxyl, and heteroaryl functionalities. One of ordinary skill in the art will realize that the diversification is only limited by the compatibility of the particular functionality with subsequent chemical reactions.

Another important aspect of the monomers utilized in the present invention includes the ability to produce both syn and anti products. Specifically, Examples 1–12 present the synthesis of syn products, and examples 13–19 present the synthesis of anti products.

Figure 14:
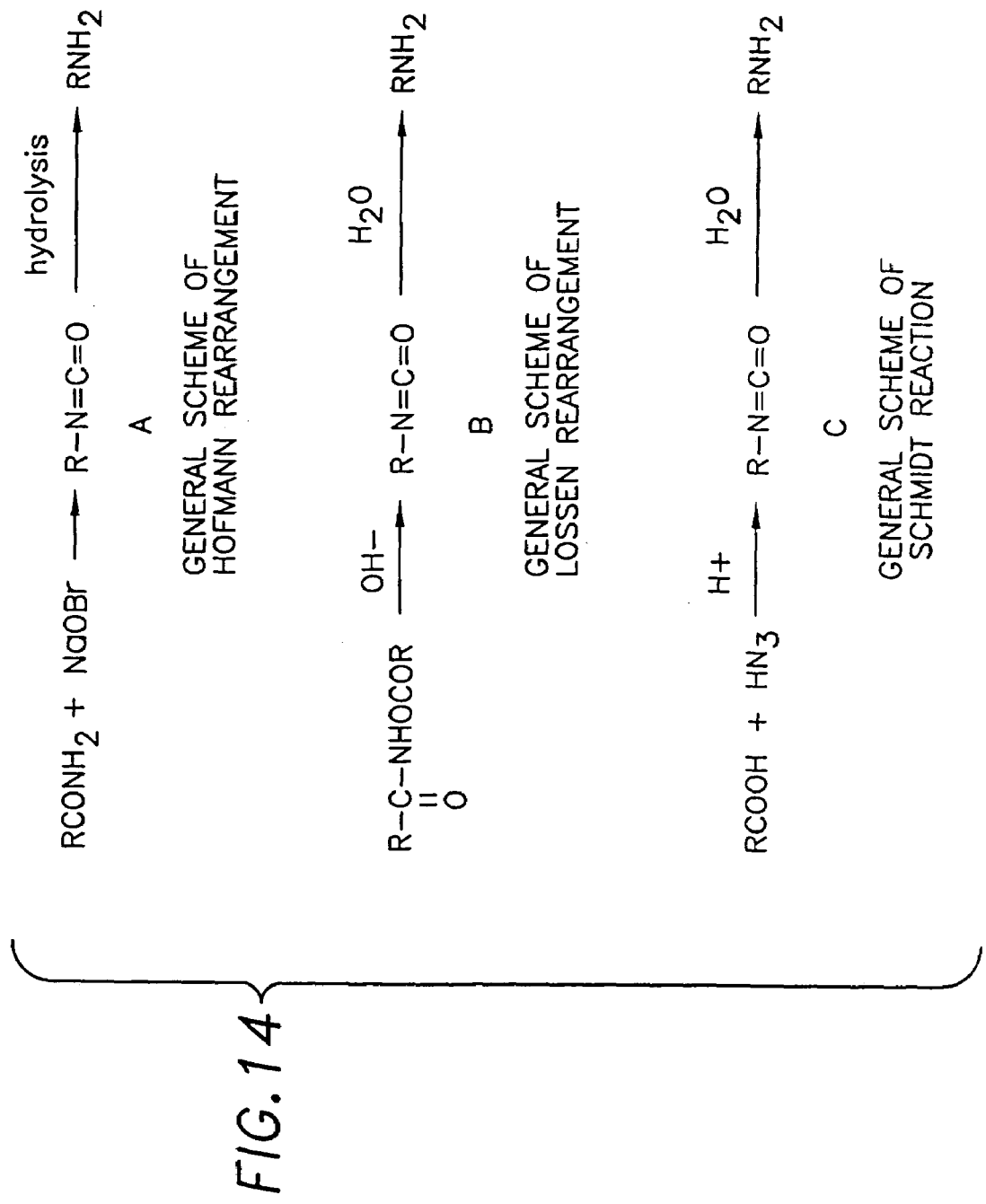
FIG. 14 depicts Hoffman, Lossen and Schmidt Rearrangements.

Yet another important aspect of the particular monomers produced according to FIGS. 11 and 12 is their ability to be converted into useful second monomers by utilizing the Curtius rearrangement as shown below in FIGS. 12 and 13. The Curtius rearrangement yields a stereochemically pure second monomer from the first monomer and thus under these reaction conditions, the stereocenters are rigidly set. In addition, stereochemically pure monomers can be obtained from other rearrangements such as the Hofmann, Lossen and Schmidt Rearrangements, as shown generally in FIG. 14. The capability of controlling the stereochemistry of the present invention allows the development of peptidomimetics or libraries of peptidomimetics that may have certain desired conformational and binding properties.

Reacting the Monomers

Once appropriate monomers are selected to have the desired structural and reactive characteristics discussed above, a first monomer may be reacted with a second monomer, or a sole monomer may be diversified. In multiple monomer embodiments, the reaction of the first and second monomers may occur inter-or intramolecularly. That is, if the monomers have already been linked to one another as described above (see for example, Formula 52), their subsequent reaction is intramolecular; if they have not been so linked, their reaction is intermolecular. Whether the reaction employed is intermolecular or intramolecular, the monomers are selected to have terminal functional moieties $L_{12}$ and $L_{21}$ capable of reaction with one another so that the monomers become attached. In particularly preferred embodiments of the invention, $L_{12}$ and $L_{21}$ are both terminal alkenes. Alternatively, each of $L_{12}$ and $L_{21}$ may be selected from the group comprising but not limited to alkenes, alkynes, amines, carboxylic acids, halogenated aromatics, aldehydes, and vinyl halides.

Figure 15:
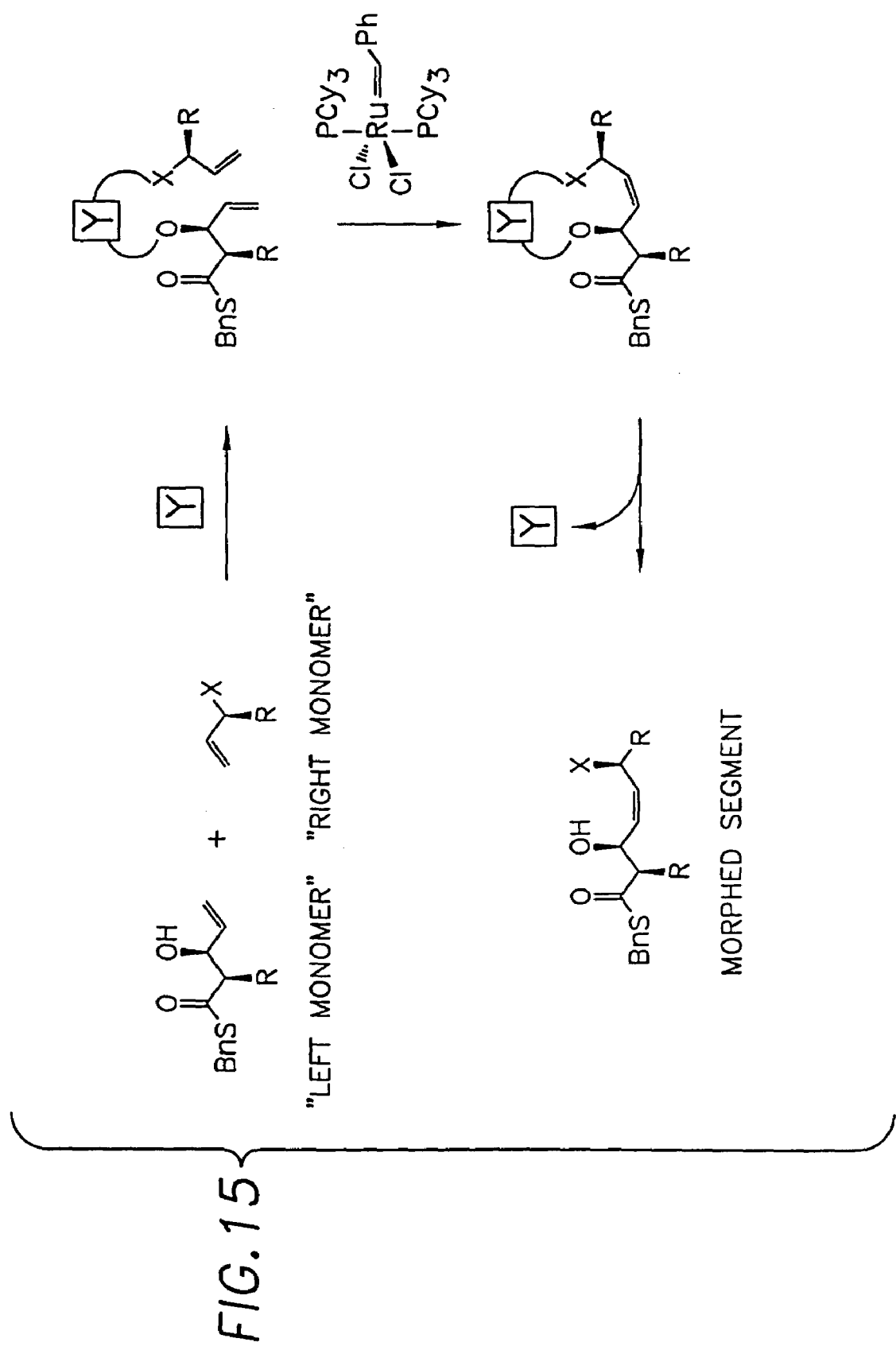
FIG. 15 depicts intramolecular olefin metathesis.
Figure 16:
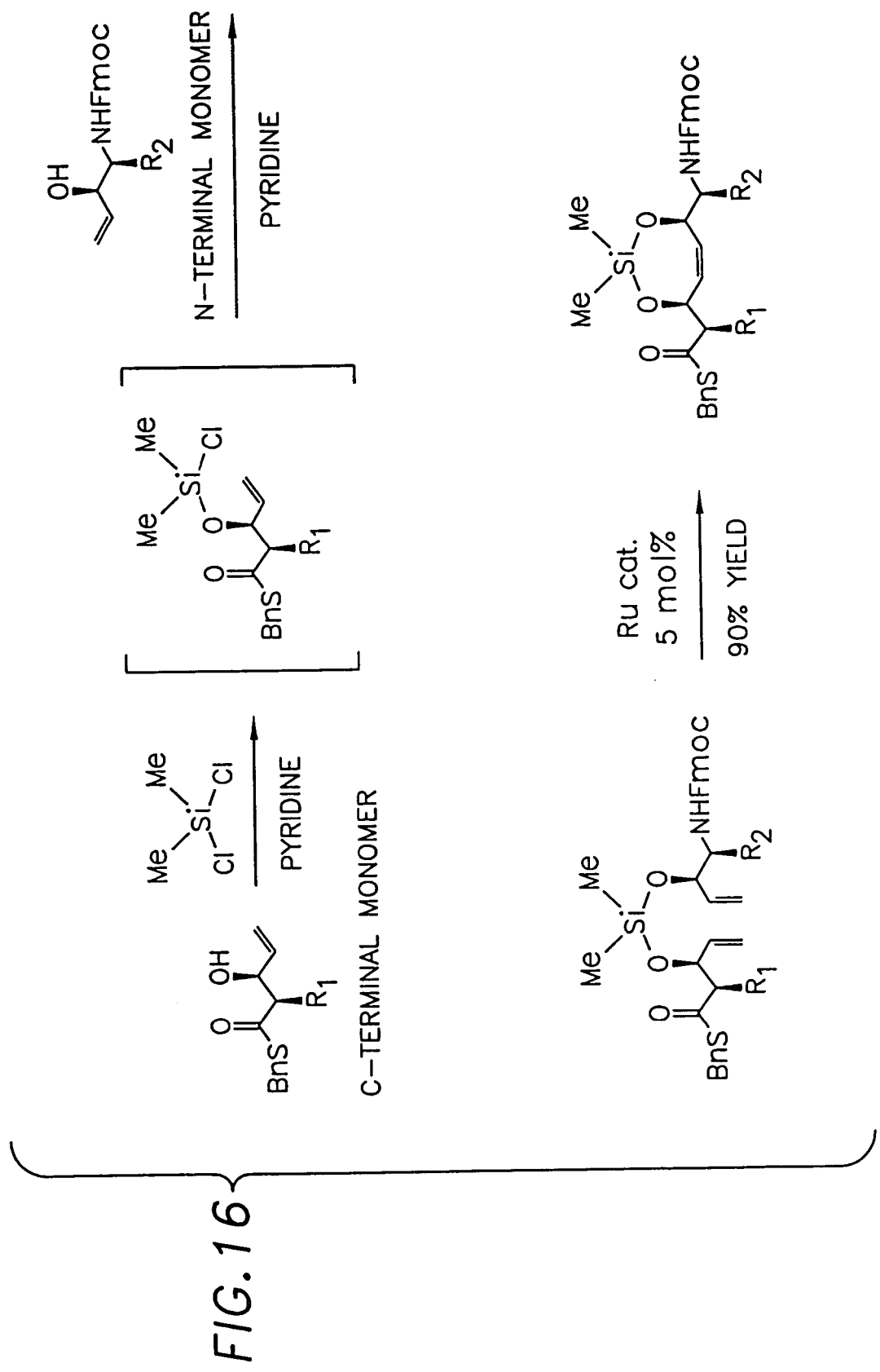
FIG. 16 depicts reaction of a dimethyldichlorosilane linker with preferred monomers of the invention.
Figure 17:
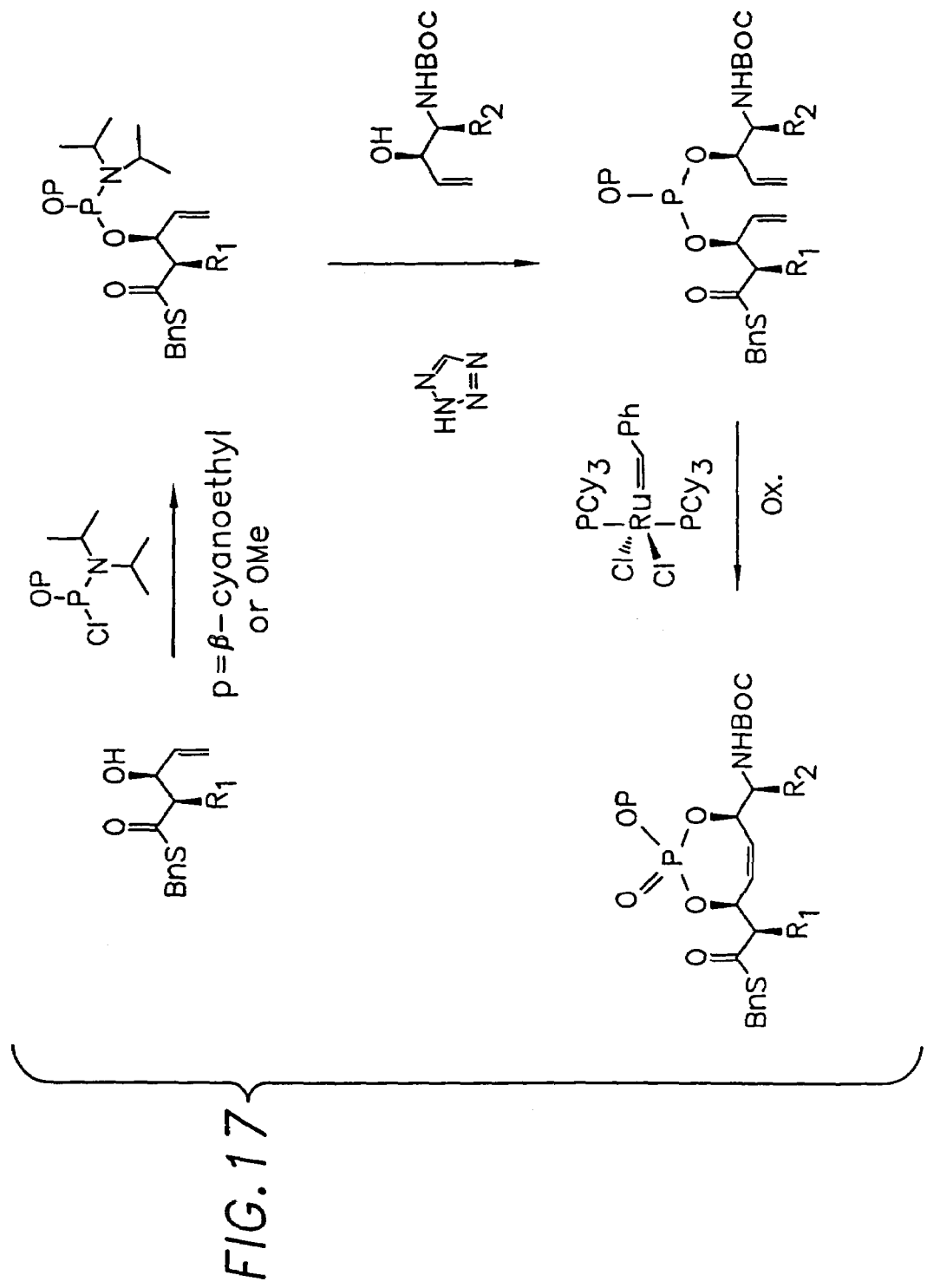
FIG. 17 depicts reaction of a diisopropylamino chlorophosphoramidite linker with preferred monomers of the invention.

In an intramolecular reaction according to the present invention, the first and second monomers (depicted as C-terminal and N-terminal monomers, respectively) each have a linking group binding site and are linked together by means of a crosslinking reagent as shown in FIG. 15. In a particularly preferred embodiment of the present invention, the first and second monomers each have a heteroatom-containing linking group binding site and are linked together by means of a silicon crosslinker such as dimethyldichlorosilane as shown in FIG. 16. In another particularly preferred embodiment of the invention, the monomers each contain a hydroxyl or amine linking group binding site and diisopropylamino chlorophosphoramidite is utilized as a linking reagent as shown in FIG. 17. It is particularly preferred that these linked monomers comprise alkene terminal reactive moieties and thus are subjected to reaction conditions to effect an intramolecular metathesis reaction to generate an alkene moiety. One particular advantage of this approach is that the resultant linker provides a phosphorous moiety that can act as an additional site for functionalization. For example, oxidation can be employed to generate an oxide, which will enable further diversification. Additionally, the generation of a phosphate is advantageous because phosphorylation of peptides is a key step in many intracellular processes, and therefore peptidomimetic structures containing a phosphate-like moiety might be expected to interact with signaling proteins. Other preferred linking reagents include, but are not limited to sulfonyl chloride and suitable reagents containing metals such as boron or titanium (e.g., $TiCl_4$)

Figure 4:
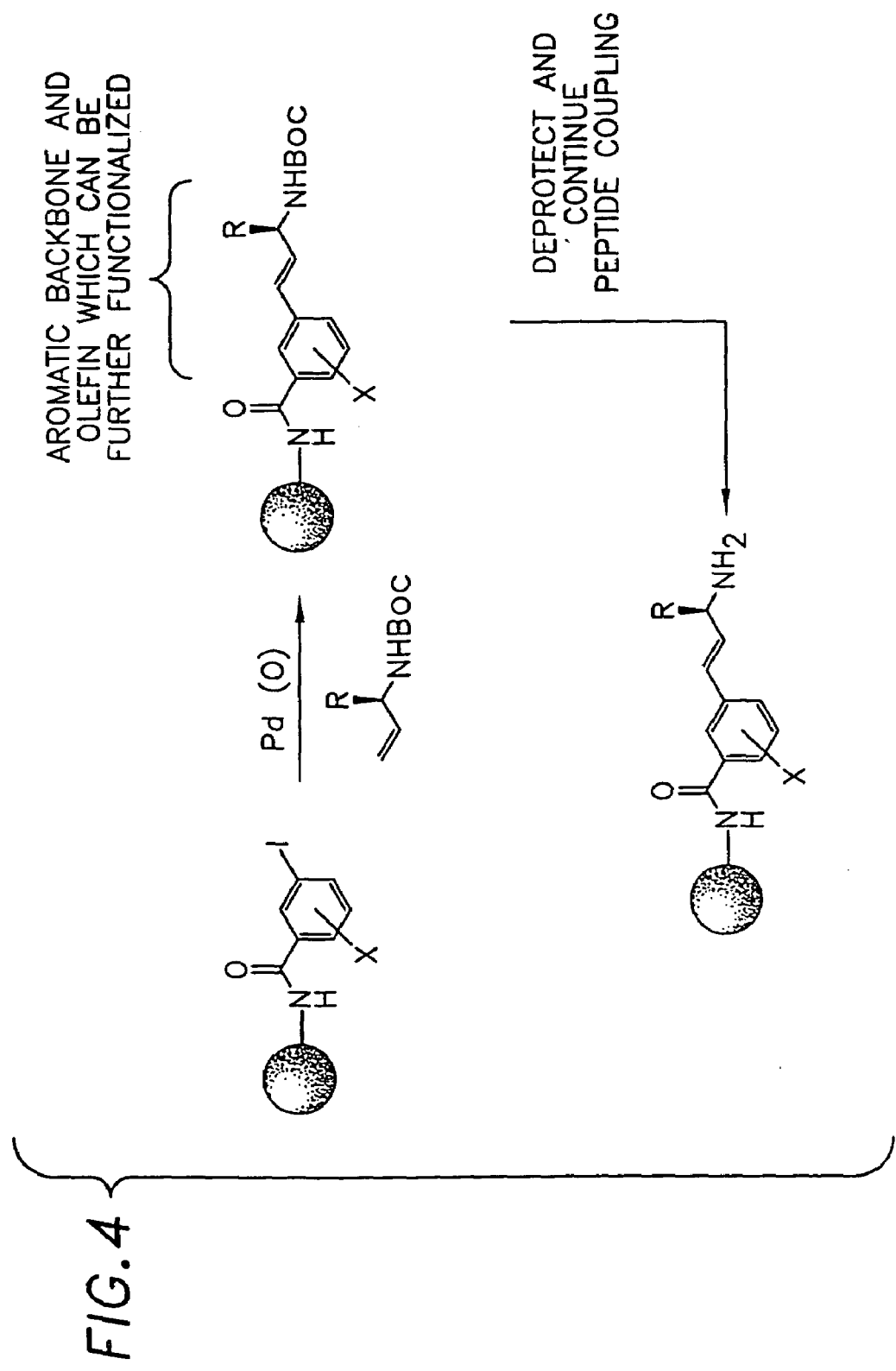
FIG. 4 depicts bond construction through palladium coupling.
Figure 5:
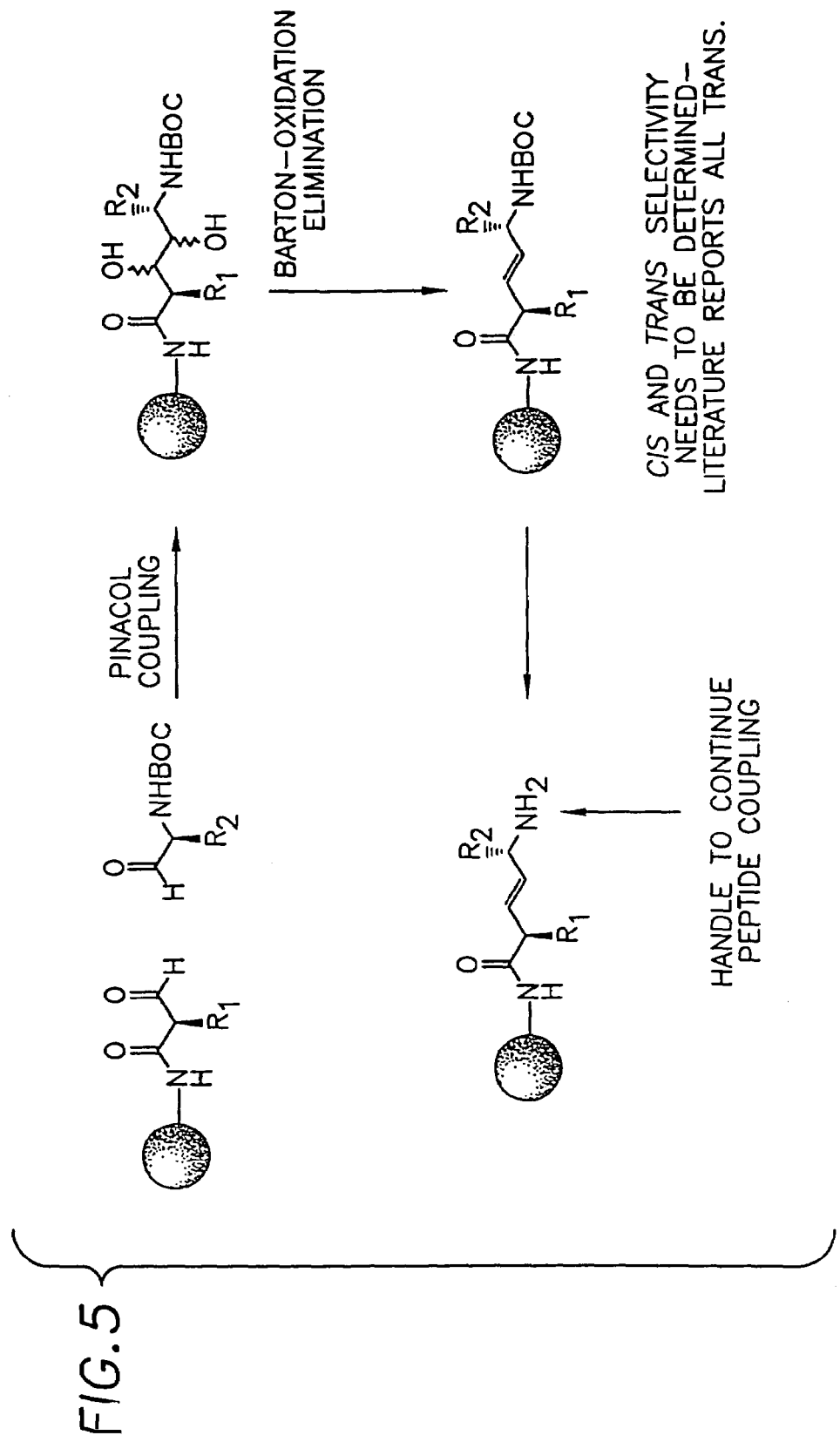
FIG. 5 depicts bond construction through pinacol coupling.
Figure 6:
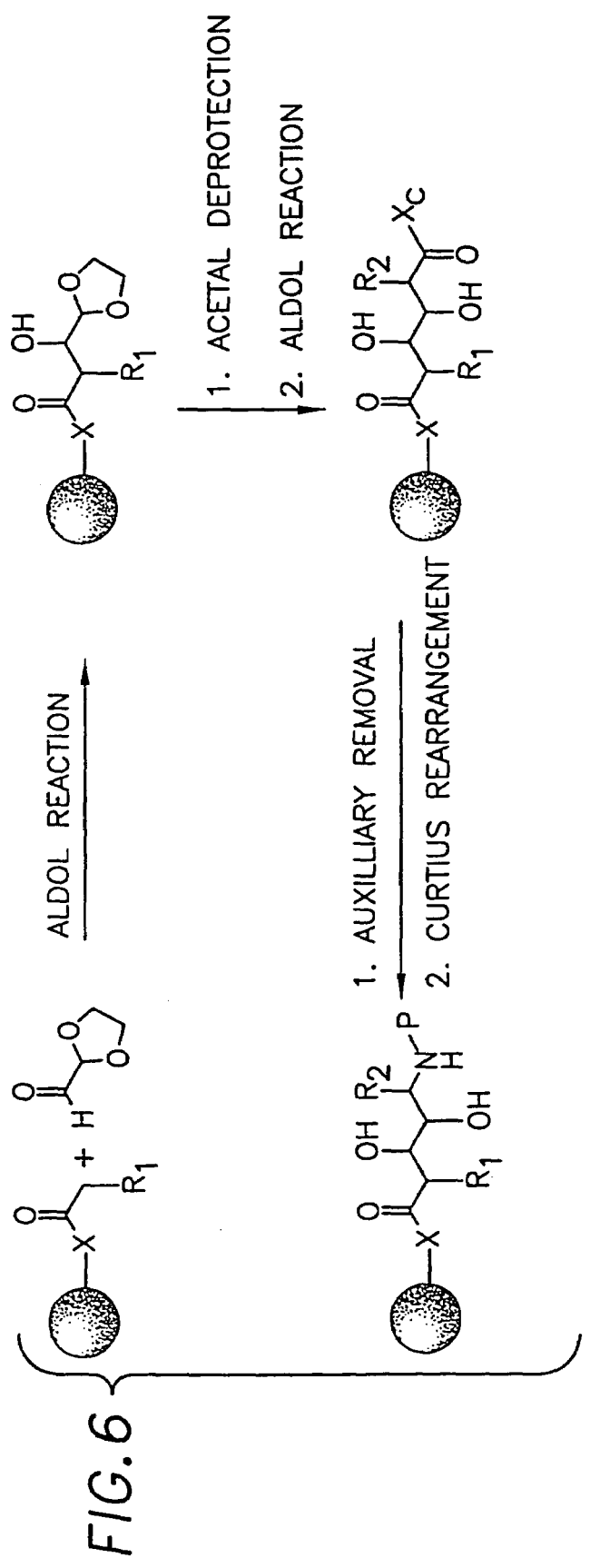
FIG. 6 depicts bond construction through tandem aldol reaction followed by Curtius rearrangement.
Figure 7:
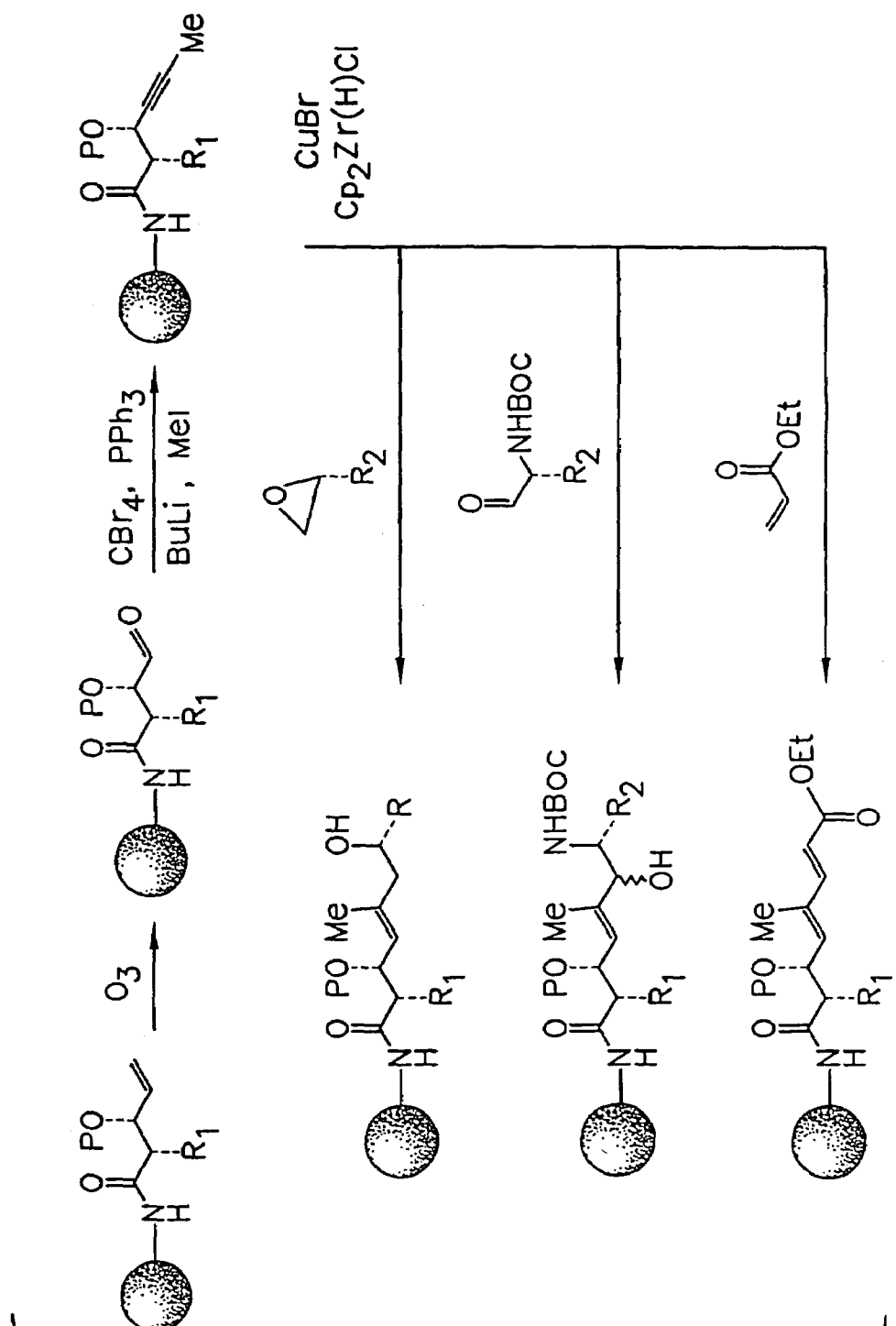
FIG. 7 depicts hydrozirconation reactions.
Figure 8:
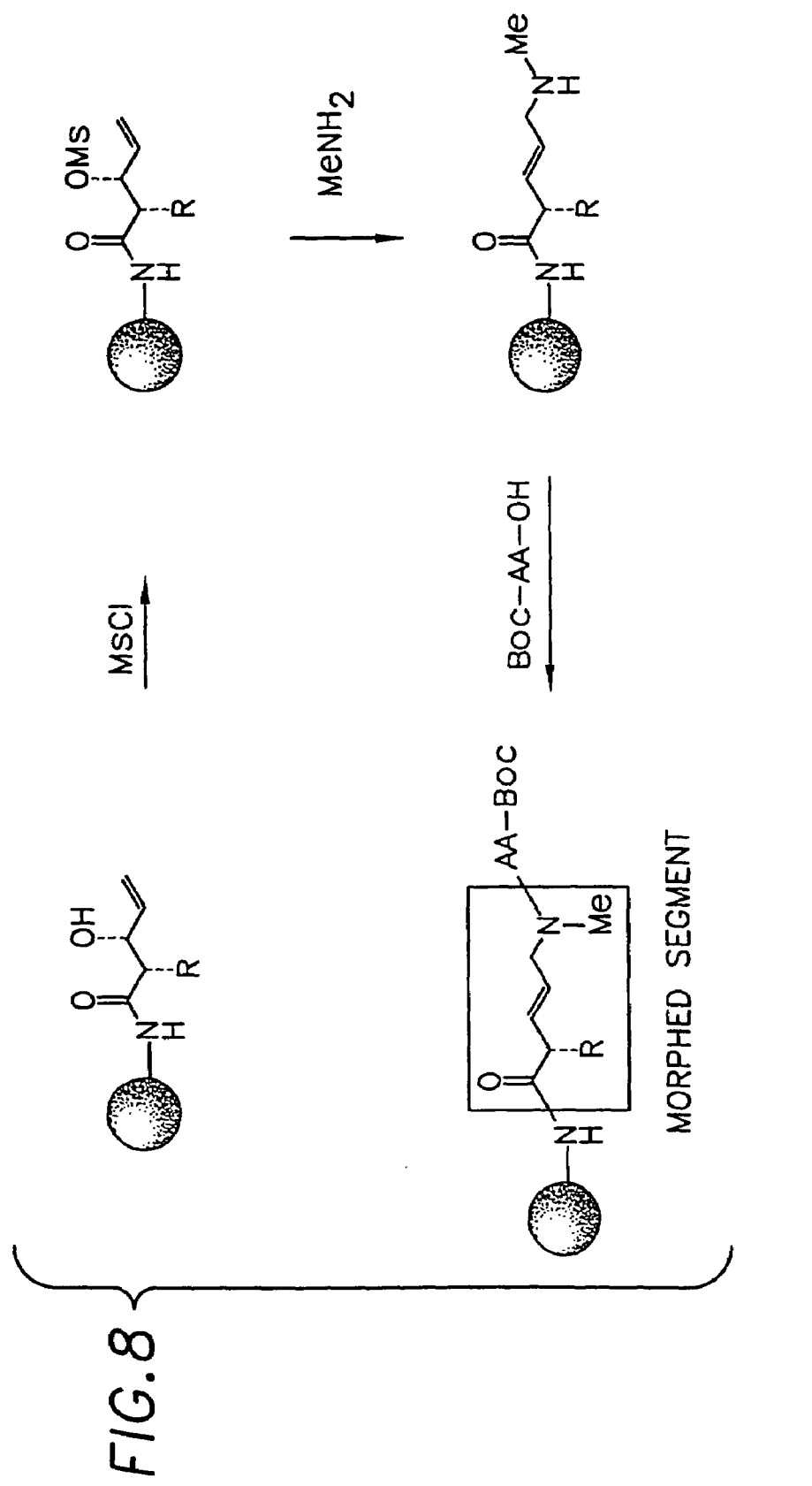
FIG. 8 depicts a nucleophilic addition reaction.
Figure 18:
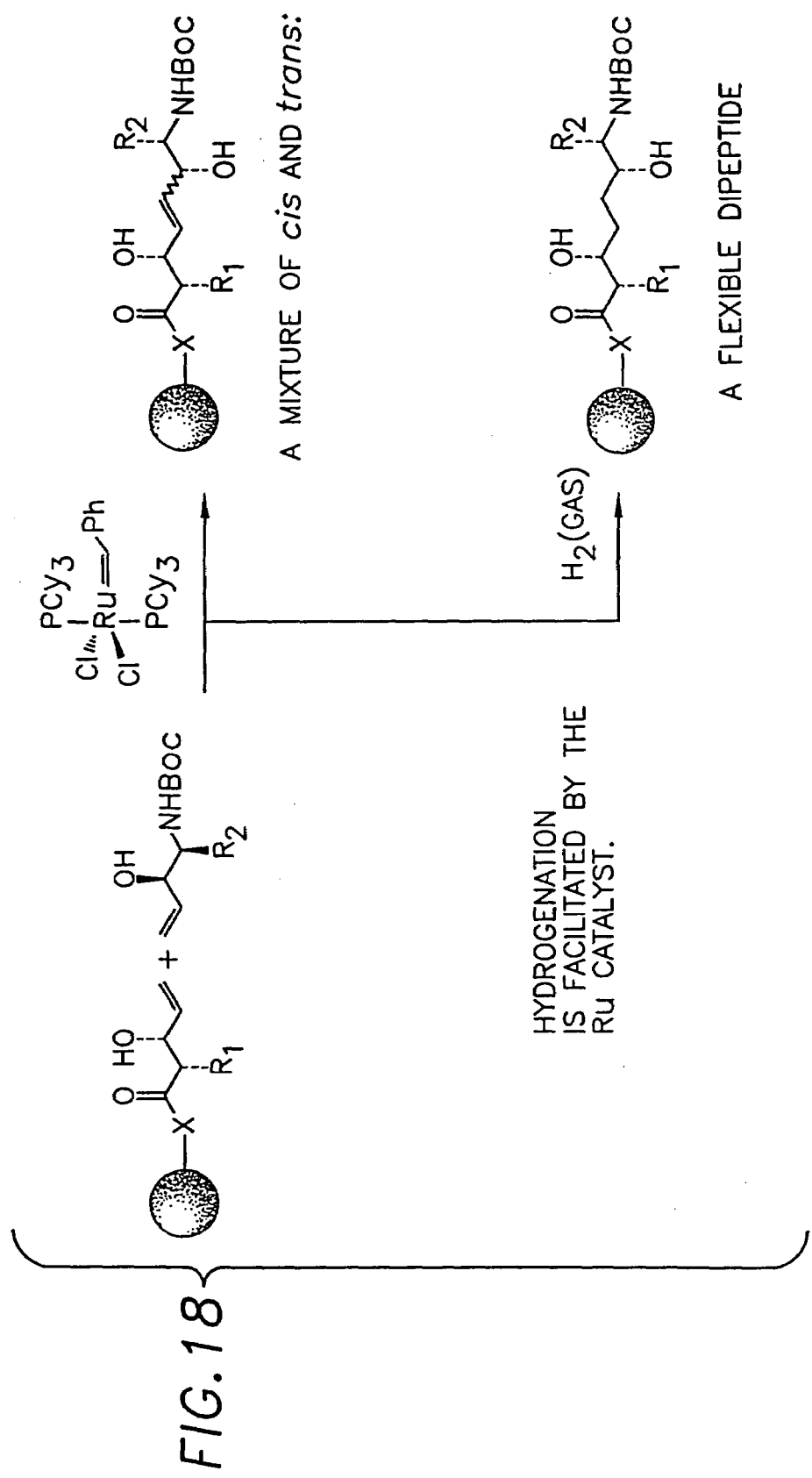
FIG. 18 depicts intermolecular olefin cross metathesis reactions.
Figure 19:
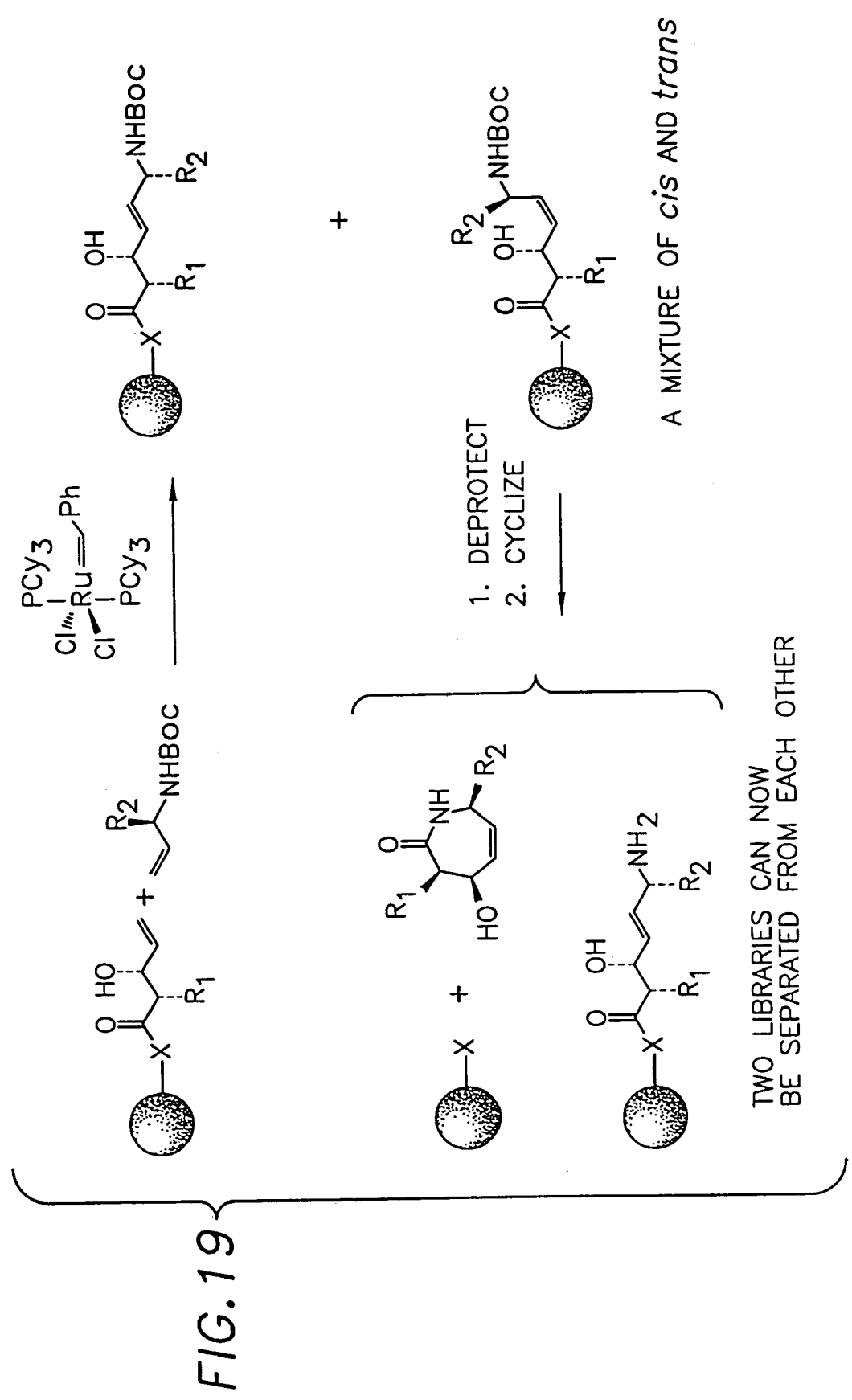
FIG. 19 depicts separation of two libraries generated from intermolecular olefin cross metathesis.

One example of a preferred inventive intermolecular reaction is depicted in FIG. 18, in which an olefin metathesis reaction yields two potential libraries. Olefin metathesis is effected by using transition metal catalysts for ring closing metathesis reactions. Traditionally, Grubbs' catalyst has been utilized for these types of reactions, however, recently, more efficient versions of this catalyst have been developed (see, Tet. Lett., 1999, 40, 2247) to effect ring closing metathesis reactions for more difficult substrates. The mixture of compounds obtained from the non-hydrogenated product can be separated by subsequent deprotection and cyclization, for example as shown in FIG. 19. Preferred intermolecular embodiments of the present invention also include linking the first and second monomers in a transition metal mediated crosscoupling reaction, such as the palladium catalyzed Heck Reaction as shown in FIG. 4, in which a haloaromatic first monomer is reacted with a second monomer under palladium (0) catalysis to yield an aromatic backbone and olefin that can be further functionalized.

Furthermore, the amine functionality can also be deprotected and peptide coupling continued. Preferred intermolecular embodiments of the present invention also include a pinacol coupling followed by elimination to yield an alkene, bond construction through tandem aldol reaction followed by Curtius rearrangement, hydrozirconization of terminal alkynes, and nucleophilic addition involving terminal alkenes, and NI-IK coupling, as shown in FIGS. 5, 6, 7, 8, and 9 respectively.

Figure 20:
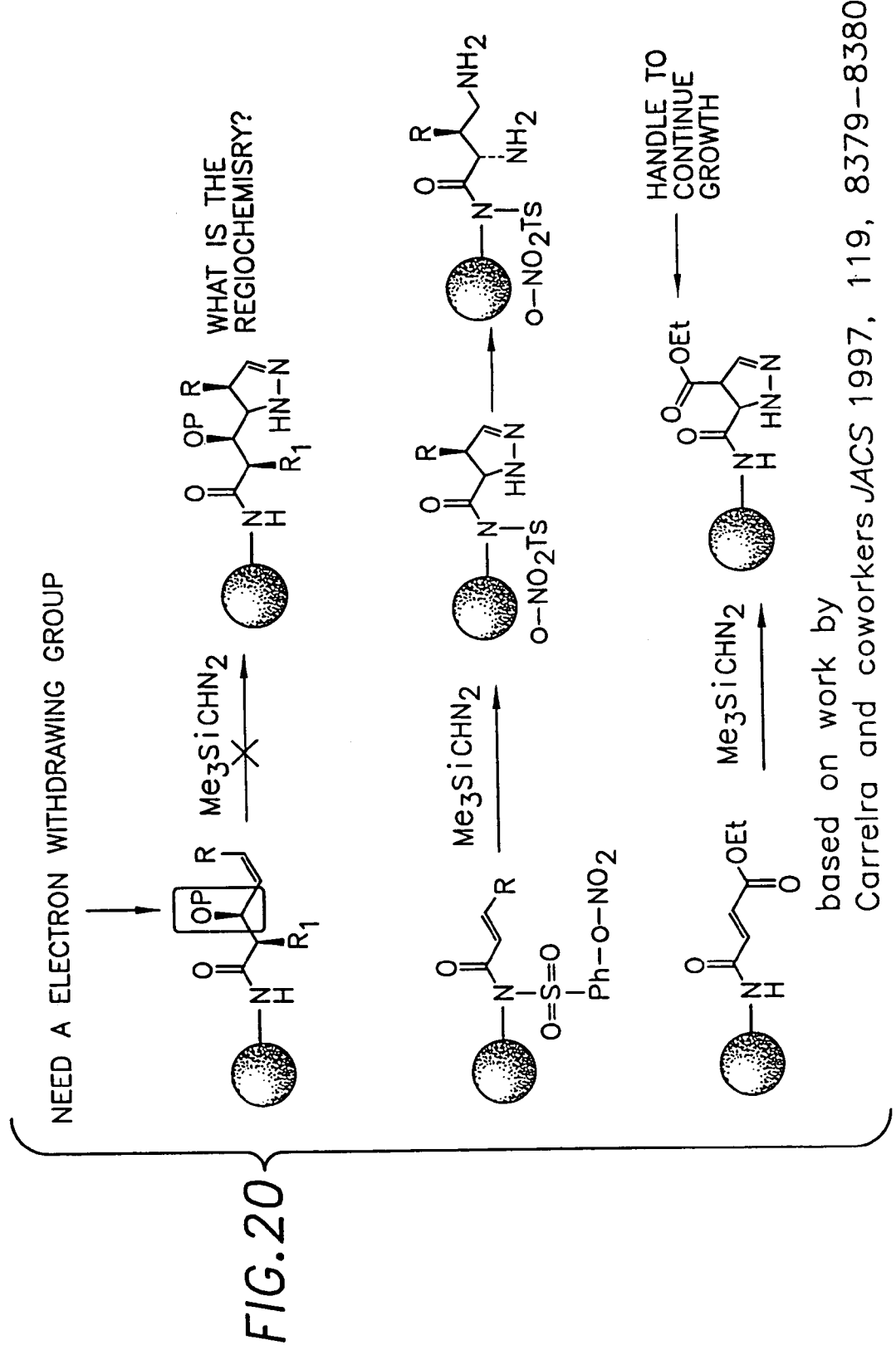
FIG. 20 depicts bond construction through cycloaddition.
Figure 21:
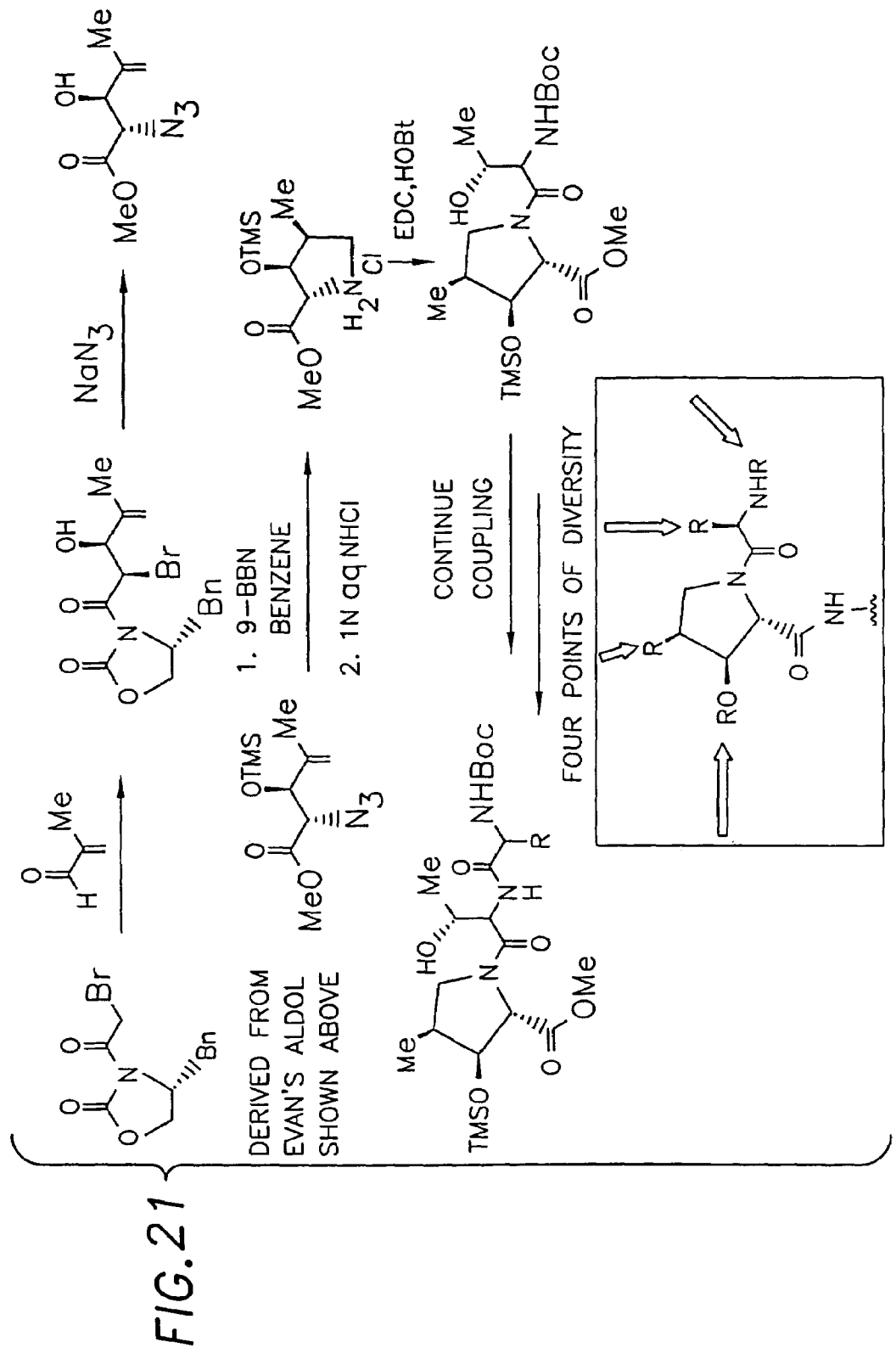
FIG. 21 depicts a diversifiable core structure from the thesis of Ann Weber.
Figure 22:
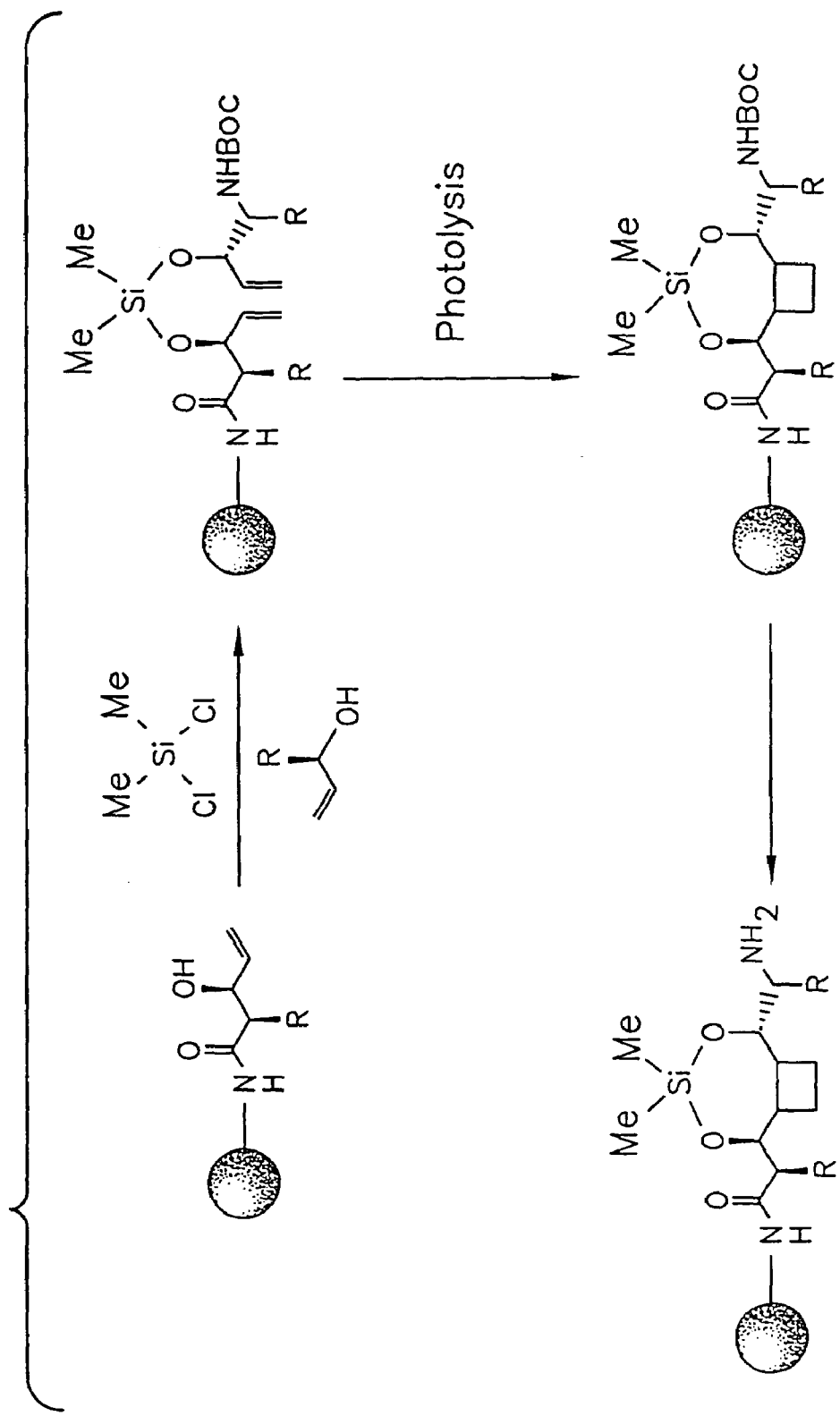
FIG. 22 depicts a directed photolysis reaction using a silicon linker.

In preferred single-monomer embodiments of the present invention, the first monomer, instead of being reacted with a second monomer as described above, is reacted with a reactive moiety to yield a molecule containing a diversifiable segment unit and diversifiable functional groups (R). For example, a diastereoselective cycloaddition, based upon the work of Carreira et al. (J. Am. Chem. Soc. 1997, 119, 8379), is shown in FIG. 20, in which dipolarophiles are reacted with $Me_3SiCHN_2$ to yield $^2$-pyazolines. Each of the structures shown in FIG. 20 contain reactive moieties which may be further functionalized. Alternatively, these reactive moieties are capable of attachment of biomolecules, preferably peptides, to yield complex compounds and libraries of compounds. Additionally, work from the thesis of Ann Weber is shown in FIG. 21 in which a diversifiable monomer is generated which contains four points of diversity. This moiety is also capable of attachment of biomolecules, such as peptides, to yield complex compounds and libraries of compounds.

Diversification and Combinatorial Synthesis

As discussed above, the present invention provides a system for the production of diverse, complex peptidomimetic and/or stereodiverse libraries. As already noted, each of the monomers utilized in the invention is capable of functionalization at one or more sites. That is, each monomer may contain functionalizable moieties as part of the base monomer structure, the terminal functionalities, and the linking group binding site. Where the monomers are linked together prior to attachment through an intramolecular reaction, the linking reagents and therefore the linker attaching the monomers, may also contain one or more functionalizable sites. These functionalizable sites may be diversified with any desirable moiety, including but not limited to hydrogen, alkyl aryl, phenoxy, methoxy, halide, methylene cyclohexyl, benzyl, heteroaryl, aryloxy, carboxyl, carboxalkyl, carboxaryl, arylalkyl, thio, and hydroxyl. This functionalization, however, is in general limited to those functionalities that will not participate in undesirable side reactions during the coupling reaction. For example, olefins, more particularly terminal olefins, interfere with the coupling process because of their ability to participate in undesirable side reactions. Those of ordinary skill in the art will appreciate that monomers and/or linking reagents can be functionalized either before or after being reacted, and thus the chemistry employed must be compatible with existing functionalities. Preferably, the monomers are first reacted to produce a single core molecule that is subsequently functionalized and diversified. The diversification reactions are preferably performed according to combinatorial approaches such as split-and-pool or parallel synthesis. Preferably, the reactions are performed to produce libraries having at least approximately 10 members, more preferably at least approximately 1,000 members, and most preferably 10,000 to about 1,000,000 or about 10,000,000 members.

Formula 53 represents one particular embodiment of a core molecule available for functionalization according to the present invention.

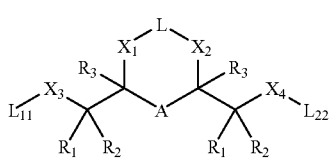

Formula 53

Preferably $L_{11}$ and $L_{22}$ each comprise the same or different terminal reactive moiety selected from the group consisting of hydrogen, protecting group, alkene, alkyne, amine, carboxylic acid, halogenated aromatic, aldehyde and vinyl halide; $R_1$, $R_2$ and $R_3$ are preferably selected from the group consisting of hydrogen, alkyl, aryl, phenoxy, methoxy, halide, methylene cyclohexyl, benzyl, heteroaryl, aryloxy, heteroaryl, carboxyl, carboxalkyl, carboxaryl, arylalkyl, thio and hydroxyl; $X_3$ and $X_4$ each preferably comprises a functional moiety selected from the group consisting of carboxyl, amino, gem-dialkyl, and methylene; $X_1$ and $X_2$ preferably each comprise a functionality containing nitrogen, oxygen, sulfur or carbon; L preferably comprises a group, including but not limited to mixed carbonates (R and R'), carbamates, disulfides, ureas, acetals, ortho esters, phosphates and oxides, produced by reaction with a linking reagent. In this embodiment, the core functionality A is most preferably an alkene. It is well known that (E) olefin isoteres have been shown to be useful replacements for the amide linkage in drug candidates because the (E)—CR═CH group closely approximates the bond lengths, angles, and rigidities of the natural parent amide. However, as discussed above, the ability to generate compounds that do not necessarily mimic the structural properties of peptides, such as the (Z) olefin generated in the present system, constitutes an additional advantage of the present invention because it permits further investigation into unknown interactions between molecules and cellular receptors.

The structure depicted in Formula 53 is available for randomization and diversification at several sites, allowing for the rapid synthesis of a library of compounds capable of emulating peptidic functions and structures, although these compounds are not necessarily required to emulate peptidic structure. For example, diversification can be achieved through functionalization at the R groups, represented by $R_1$, $R_2$ and $R_3$ as shown in Formula 53. At such sites, various functionalities can be substituted including but not limited to hydrogen, alkyl, aryl, phenoxy, methoxy, halide, methylene cyclohexyl, benzyl, heteroaryl, aryloxy, carboxyl, carboxalkyl, carboxaryl, arylalkyl, thio, and hydroxyl.

Figure 23:
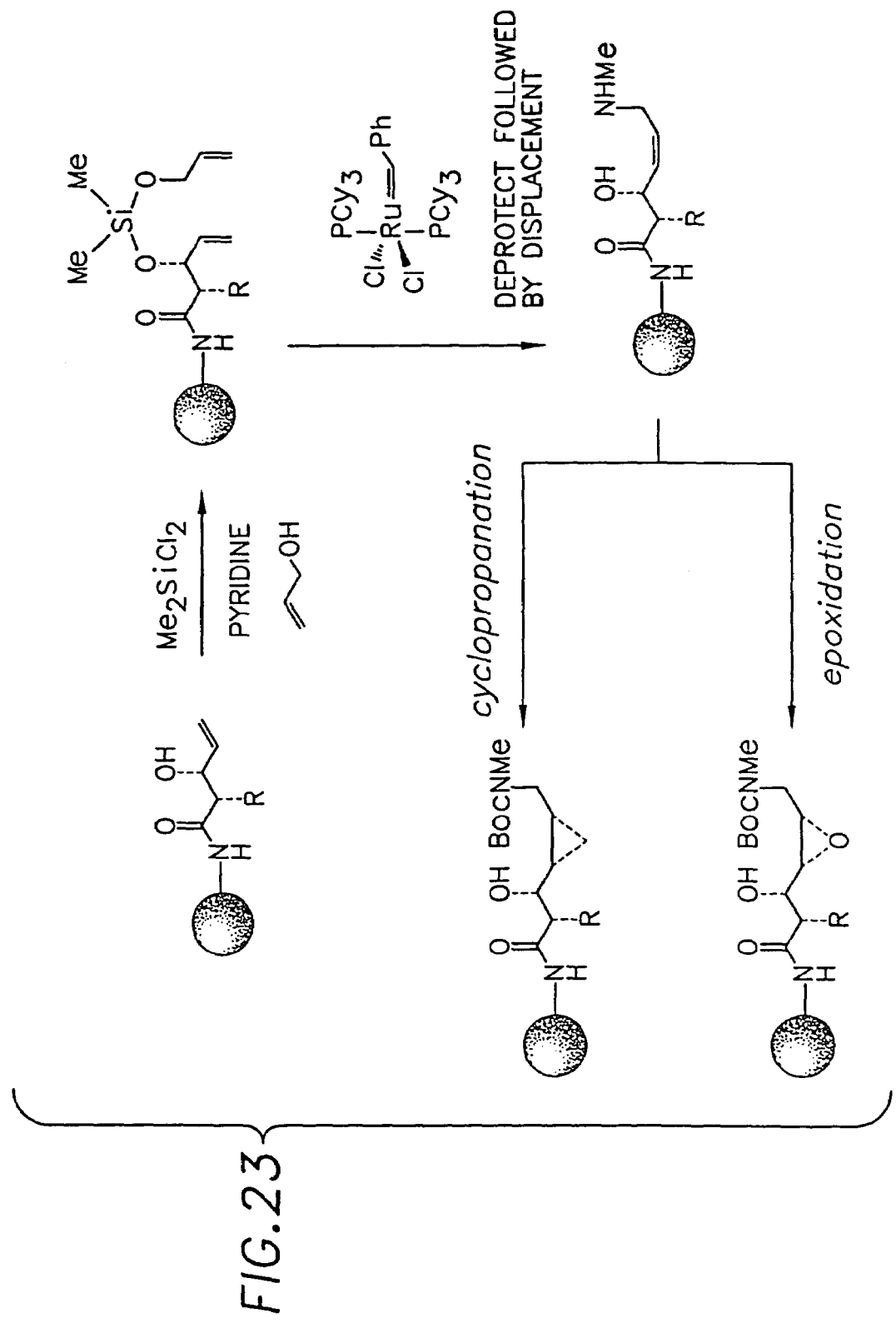
FIG. 23 depicts modification of the olefin functionality.

Alternatively or additionally, the segment unit replacement, represented by A, may be diversified. For example, instead of utilizing olefin metathesis to yield a double bond motif, a 2+2 addition to yield a cyclobutane segment unit can be initiated by photolysis (FIG. 21) or by the use of certain transition metal catalysts such as $Ti(CH_2Ph)_4$. This segment unit can then be further diversified by cyclobutane ring opening reactions including but not limited to reactions with cuprates, radical type fragmentations and DeMayo fragmentations. Alternatively, the double bond product can be converted into a cyclopropane (FIG. 23) which also can be further diversified by reaction with a variety of nucleophiles, such as cuprates or organometallics. Additional diversification of the double bond may be achieved by hydrogenation, epoxidation, or dihydroxylation.

Figure 9:
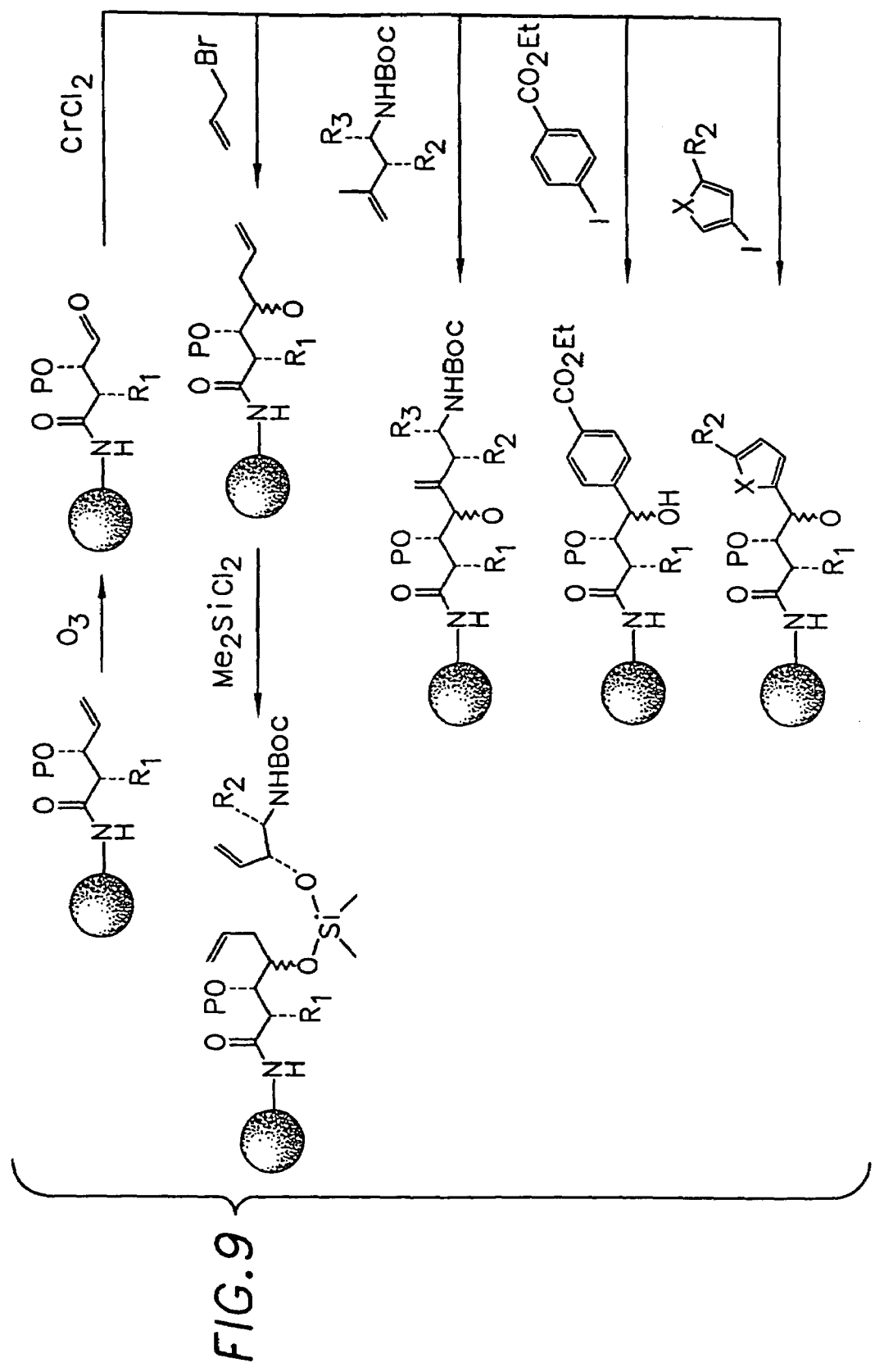
FIG. 9 depicts Nozaki-Hiyama-Kishi coupling reactions.

Although Formula 53 depicts linked monomers, one of ordinary skill in the art will realize that the present discussion of the diversification of A can be extended to other embodiments where the monomers are reacted intermolecularly. In such embodiments, the diversification of the segment unit A is achieved through palladium coupling reactions (FIG. 4), Pinacol couplings (FIG. 5), tandem aldol reactions/Curtius rearrangements (FIG. 6) hydrozirconations (FIG. 7), nucleophilic additions (FIG. 8), and NHK couplings (FIG. 9). The segment unit A also includes but is not limited to cyclobutane, cyclopropane, alkene, alkane, heteroatom, alkyne and aromatic functionalities.

Figure 24:
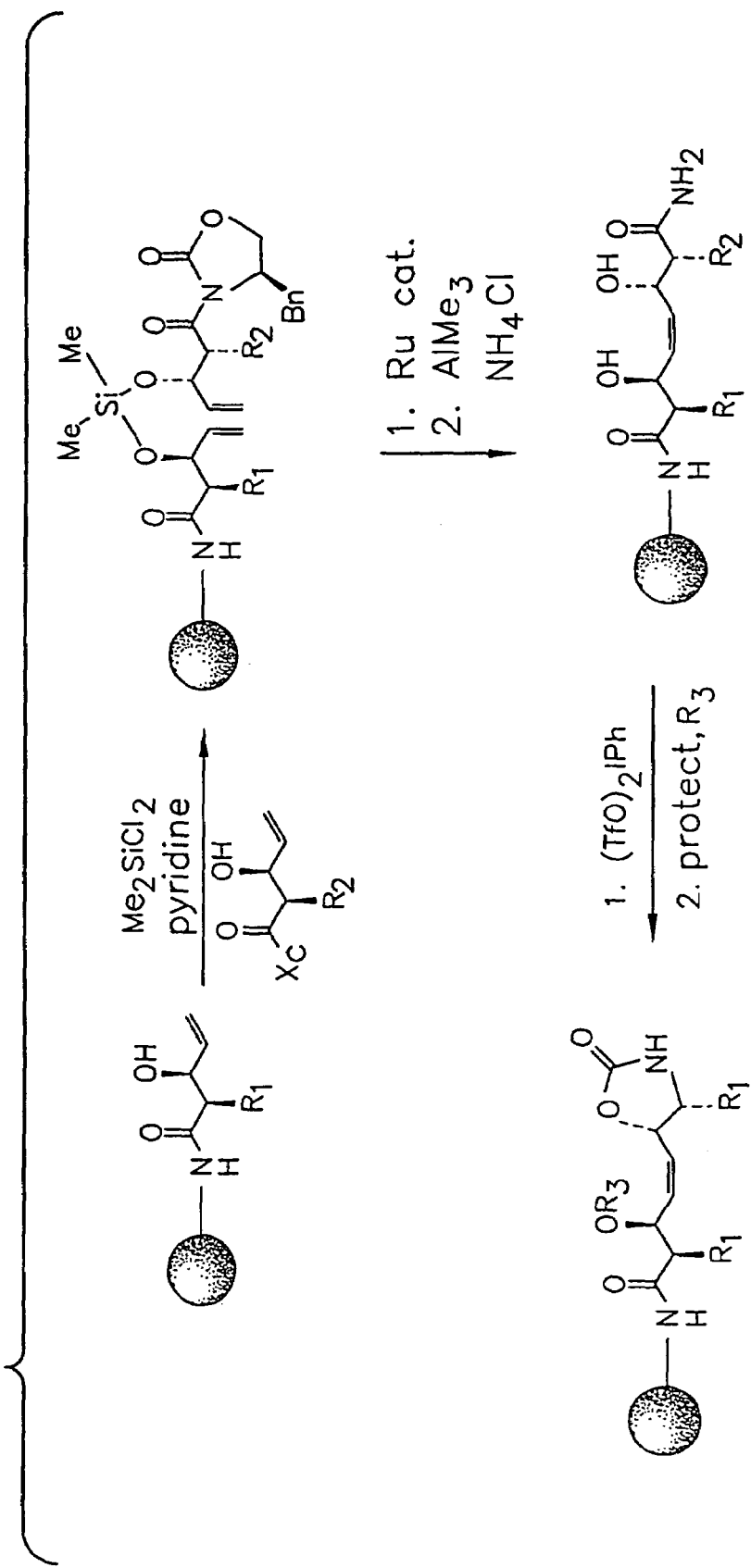
FIG. 24 depicts selective protection of a linking moiety on the resin.

In another preferred embodiment of the present invention, the linking group can be removed to yield further diversifiable functionalities $X_1$ and $X_2$, as shown in Formula1. These linking groups are preferably carbon, oxygen, sulfur or nitrogen containing functionalities such as hydroxy, thiol, or amine functionalities, which are capable of further-FIG. 24 is selectively protected via the Hoffman Rearrangement. Preferably $L_{11}$ and $L_{22}$ each comprise the same or different terminal reactive moiety selected from the group consisting of hydrogen, protecting group, alkene, alkyne, amine, carboxylic acid, halogenated aromatic, aldehyde and vinyl halide; $R_1$, $R_2$ and $R_3$ are preferably selected from the group consisting of hydrogen, alkyl, aryl, phenoxy, methoxy, halide, methylene cyclohexyl, benzyl, heteroaryl, aryloxy, carboxyl, carboxalkyl, carboxaryl, arylalkyl, thio and hydroxyl; $X_3$ and $X_4$ each preferably comprises a functional moiety selected from the group consisting of carboxyl, amino, gem-dialkyl, and methylene; and $X_1$ and $X_2$ preferably each comprise a functionality containing nitrogen, oxygen, sulfur or carbon. In this embodiment, the core functionality A is most preferably an alkene.

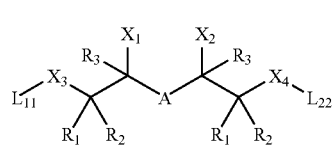

Formula 54

Combinatorial Methods

As mentioned above, the monomers may be diversified prior to or after reaction to generate core structures. Additionally, after their synthesis, the core structures can also be diversified. As will be appreciated by one of ordinary skill in the art, the synthesis of libraries from the above-described core structures and monomers can be performed using established combinatorial methods for solution phase, solid phase, or a combination of solution phase and solid phase synthesis techniques. The synthesis of combinatorial libraries is well known in the art and has been reviewed (see, e.g., "Combinatorial Chemistry", Chemical and Engineering News, Feb. 24, 1997, p. 43; Thompson, L. A., Ellman, J. A., Chem. Rev. 1996, 96, 555.) One of ordinary skill in the art will realize that the choice of method will depend upon the specific number of compounds to be synthesized, the specific reaction chemistry, and the availability of specific instrumentation, such as robotic instrumentation for the preparation and analysis of the inventive libraries. In particularly preferred embodiments, the reactions to be performed on the monomers and core structures to generate the libraries are selected for their ability to proceed in high yield, and in a stereoselective fashion.

In one embodiment of the present invention, the inventive libraries are generated using a solution phase technique. Traditional advantages of solution phase techniques for the synthesis of combinatorial libraries include the availability of a much wider range of organic reactions, and the relative ease with which products can be characterized. Notable disadvantages of solution phase techniques includes the inability to easily synthesize libraries of compounds containing very large numbers, such as one million or more library members, because one reaction vessel must be provided for each library member, and the inability to use excess reagents without time-consuming purification steps, such as chromatography. Recently, however, advances have been made in solution phase synthesis techniques such as the use of a "covalent scavenger" which selectively removes from solution via covalent bond formation. The "covalent scavenger" is essentially a solid phase bound nucleophile or electrophile that reacts with these excess reagents. (Kaldor, Eli Lilly, Frechet et al., Tetrahedron Lett., 21, 617 (1980)). In a preferred embodiment, for the generation of a solution phase combinatorial library, a parallel synthesis technique is utilized, in which all of the products are assembled separately in their own reaction vessels. In a particularly preferred parallel synthesis procedure, a microtitre plate containing n rows and m columns of tiny wells which are capable of holding a few milliliters of the solvent in which the reaction will occur, is utilized. It is possible to then use n variants of reactant A, such as a carboxylic acid, and m variants of reactant B, such as an amide to obtain n×m variants, in n×m wells. One of ordinary skill in the art will realize that this particular procedure is most useful when smaller libraries are desired, and the specific wells can provide a ready means to identify the library members in a particular well.

In another more particularly preferred embodiment of the present invention, a solid phase synthesis technique is utilized, in which the desired scaffold structures are attached to the solid phase directly or though a linking unit, as discussed above. Advantages of solid phase techniques include the ability to more easily conduct multi-step reactions and the ability to drive reactions to completion because excess reagents can be utilized and the unreacted reagent washed away. Perhaps one of the most significant advantages of solid phase synthesis is the ability to use a technique called "split and pool", in addition to the parallel synthesis technique, developed by Furka. (Furka et al., Abstr. 14th Int. Congr. Biochem., Prague, Czechoslovakia, 1988, 5, 47; Furka et al., Int. J. Pept. Protein Res. 1991, 37, 487; Sebestyen et al., Bioorg. Med. Chem. Lett., 1993, 3, 413.) In this technique, a mixture of related compounds can be made in the same reaction vessel, thus substantially reducing the number of containers required for the synthesis of very large libraries, such as those containing as many as or more than one million library members. As an example, the core structures or monomers can be divided into n vessels. A here n represents the number species of reagent A to be reacted with the core structures or monomers. After reaction, the contents from n vessels are combined and then split into m vessels, where m represents the number of species of reagent B to be reacted with the core structures or monomers. This procedure is repeated until the desired number of reagents is reacted with the core structures or monomers to yield the inventive library.

The use of solid phase techniques in the present invention may also include the use of a specific encoding technique. Specific encoding techniques have been reviewed by Czarnik. (Czarnik, A. W., Current Opinion in Chemical Biology, 1997, 1, 60.) As used in the present invention, an encoding technique involves the use of a particular "identifying agent" attached to the solid support, which enables the determination of the structure of a specific library member without reference to its spatial coordinates. One of ordinary skill in the art will also realize that if smaller solid phase libraries are generated in specific reaction wells, such as 96 well plates, or on plastic pins, the reaction history of these library members may also be identified by their spatial coordinates in the particular plate, and thus are spatially encoded. It is most preferred, however for large combinatorial libraries, to use an alternative encoding technique to record the specific reaction history.

Examples of particular preferred alternative encoding techniques that can be utilized in the present invention include, but are not limited to, spatial encoding techniques, graphical encoding techniques, including the "tea bag" method, chemical encoding methods, and spectrophotometric encoding methods. Spatial encoding refers to recording a reaction's history based on its location. Graphical encoding techniques involve the coding of each synthesis platform to permit the generation of a relational database. Examples of preferred spectrophotometric encoding methods include the use of mass spectroscopy, fluorescence emission, and nuclear magnetic resonance spectroscopy. In a most preferred embodiment, chemical encoding methods are utilized, which uses the structure of the reaction product to code for its identity. Decoding using this method can be performed on the solid phase or off of the solid phase. One of ordinary skill in the art will realize that the particular encoding method to be used in the present invention must be selected based upon the number of library members desired, and the reaction chemistry employed.

Peptide Morphing

As mentioned above, one particular aspect of the present invention is the provision of methods and reagents for preparing and identifying chemical compounds that mimic certain desired structural and/or functional properties of a predetermined peptide. For example, a variety of techniques (e.g., alanine scanning mutagenesis, NMR, X-ray crystallography, etc.) are available for defining within a biologically active protein particular peptide sequences, or dispersed amino acids or small collections of amino acids, that are responsible for part or all of the protein's function. Once such an active sequence is defined, the present invention provides a novel approach for preparing a non-peptide compound that captures the functionality of that sequence.

In particular, the methods discussed above provide libraries of chemical compounds that typically resemble of di- or tri-peptide moieties. As discussed above, the libraries can be prepared in the context of an existing peptide structure, that functions as a biasing element for the library, or can be embedded within a peptide after their preparation.

Thus, the techniques described herein allow preparation of a library of peptide derivatives corresponding to a known active sequence except that two or three residues of the sequence are replaced with an inventive library. This peptide derivative library can readily be screened to identify those compounds within it that retain the peptide activity of interest. In this way, a portion of the peptide is "morphed" into another compound that retains the peptide activity.

This morphing method is not limited to substitution of a single di- or tri-peptide unit within an active sequence. Once one unit has been morphed, a second unit within the peptide can be subjected to the same procedure, and so on. Alternatively, two or more units may be morphed simultaneously. As yet another alternative, two or more units may be morphed in parallel and the final morphed structures may subsequently be embedded within a single peptide.

Once a portion of an active sequence has been successfully morphed, it may be possible to remove some or all remaining peptide sequence without destroying the peptide-like activity of the compound. Another way of removing all peptide components from an active sequence, of course, is to morph the entire sequence.

Uses

The method, compounds, and libraries of the present invention can be utilized in various disciplines. Any available method may be employed to screen the libraries produced according to the present invention to identify those with desirable characteristics for a selected application.

Figure 25:
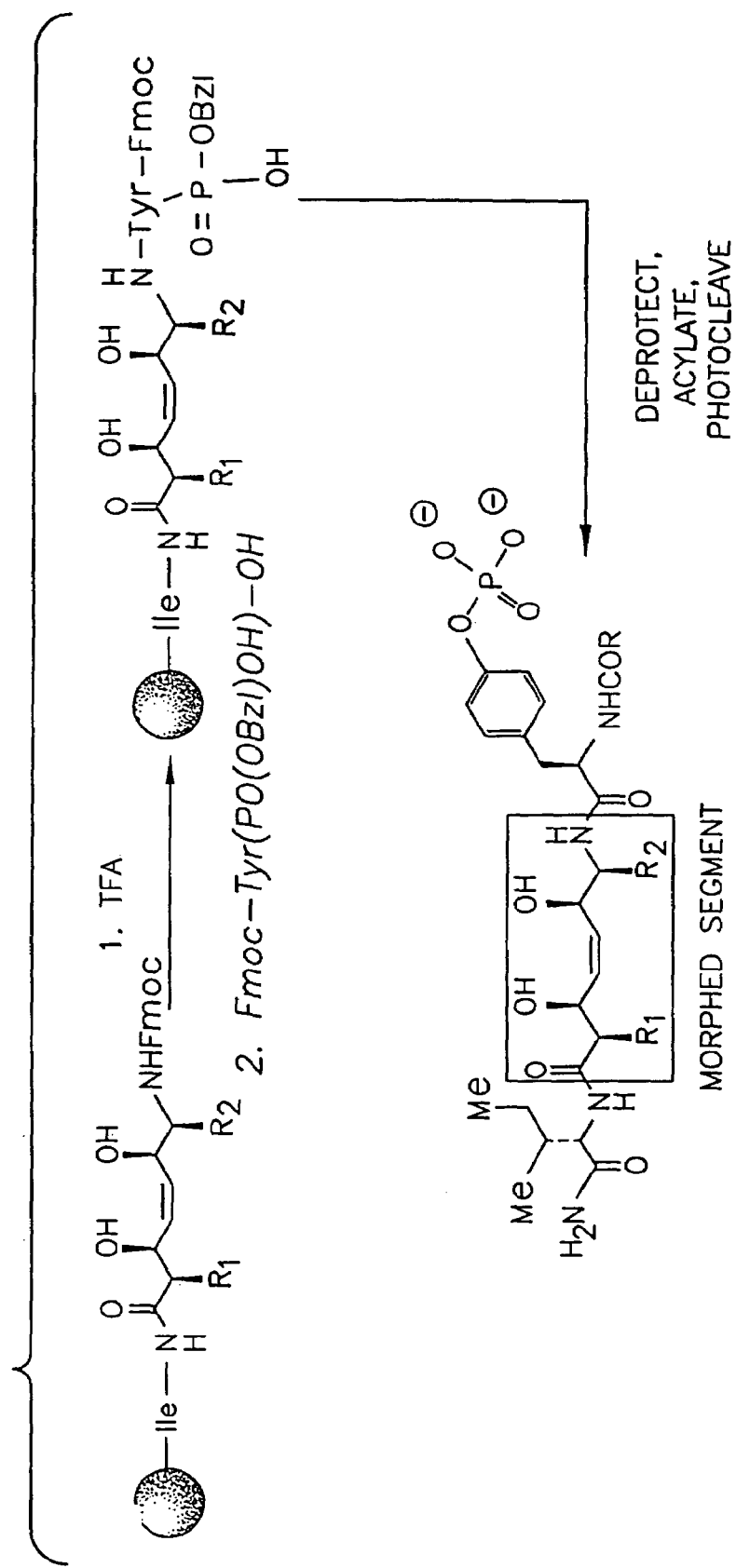
FIG. 25 depicts embedding morphed segment in an $SH_2$ binding peptide.
Figure 27:
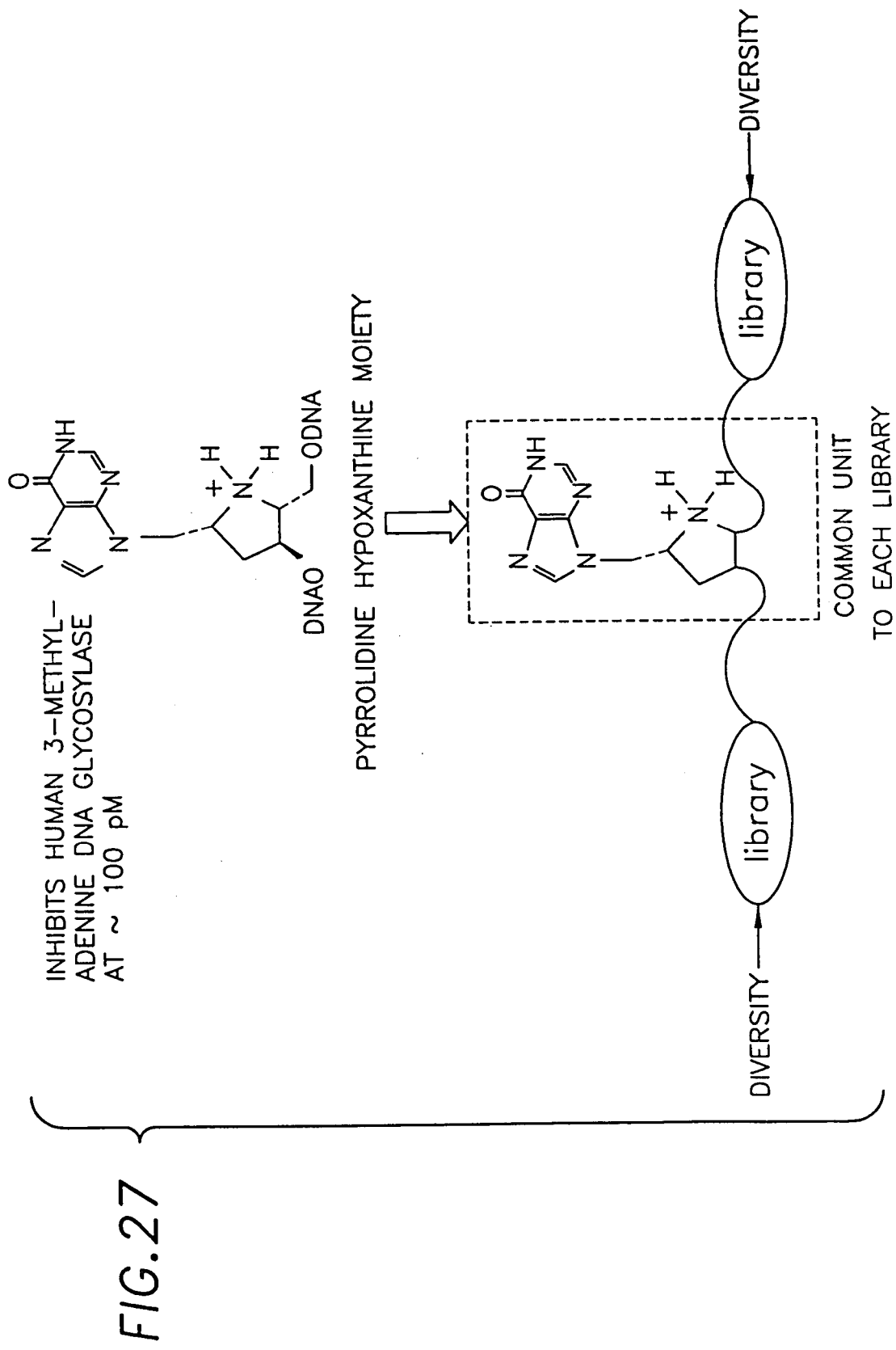
FIG. 27 depicts a library of inhibitors of DNA glycosylases.
Figure 28:
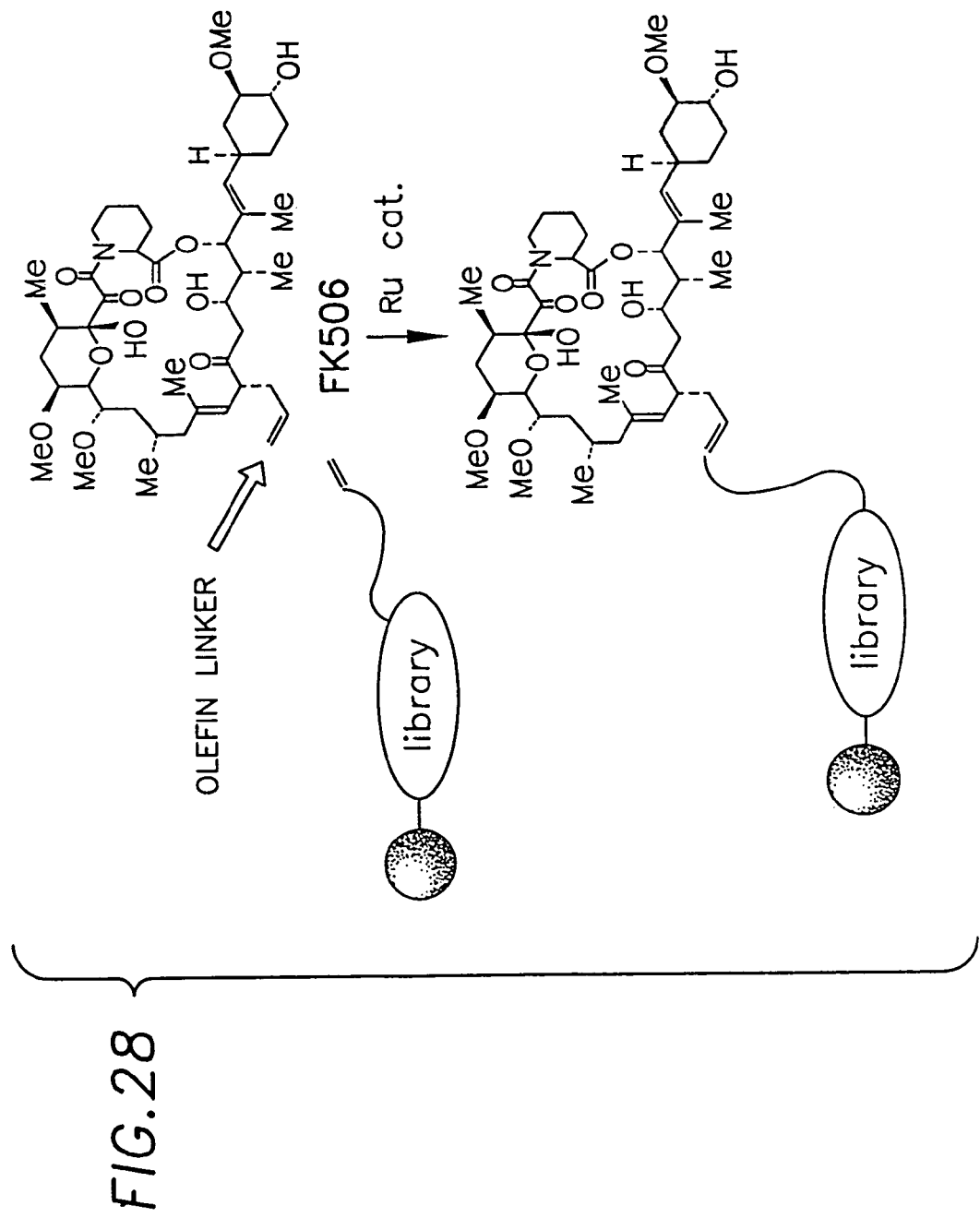
FIG. 28 depicts a library of synthetic transcriptional regulators.
Figure 29:
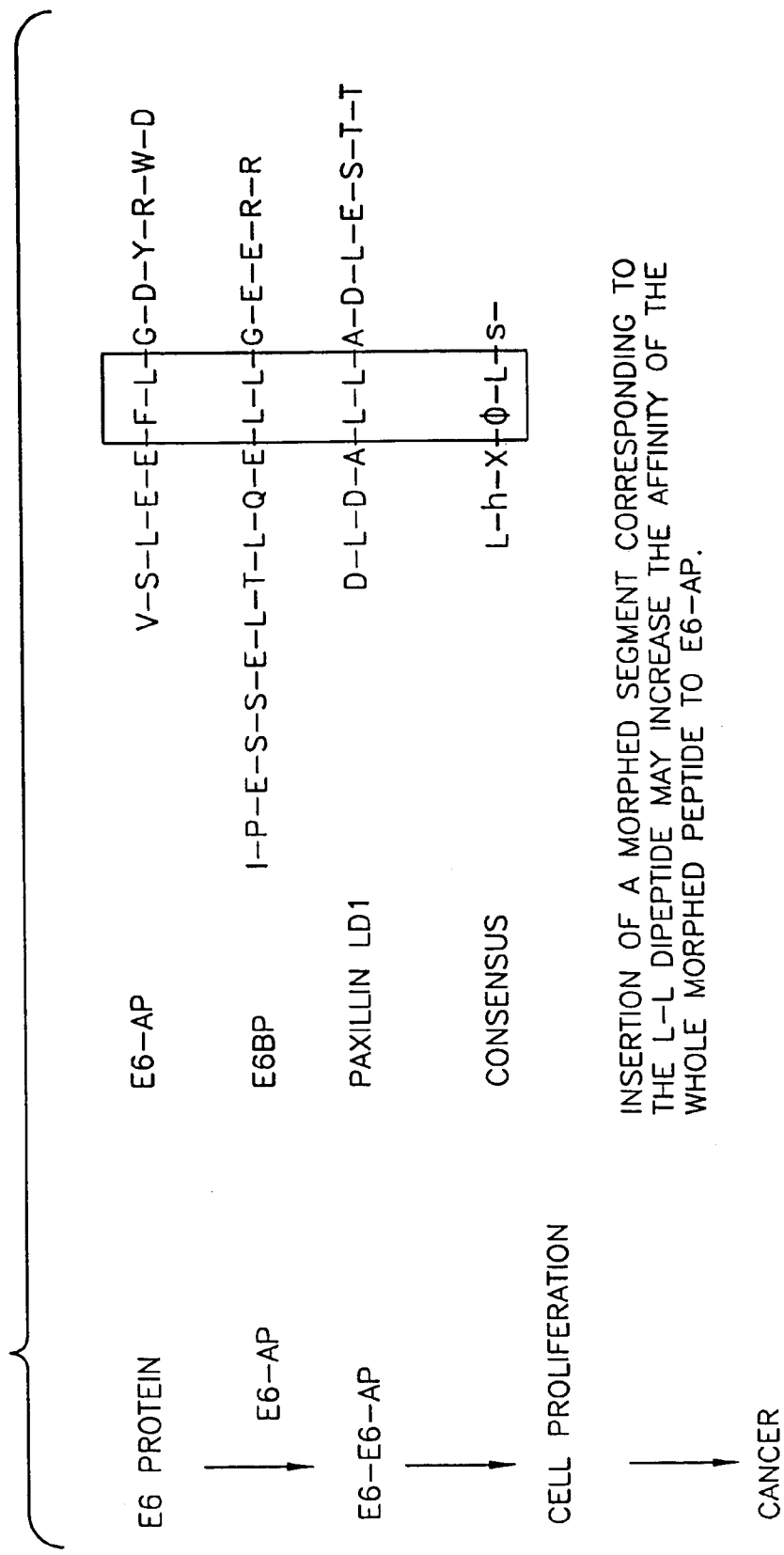
FIG. 29 depicts a use for the compounds and libraries of the present invention in the E6E6-AP system.
Figure 30:
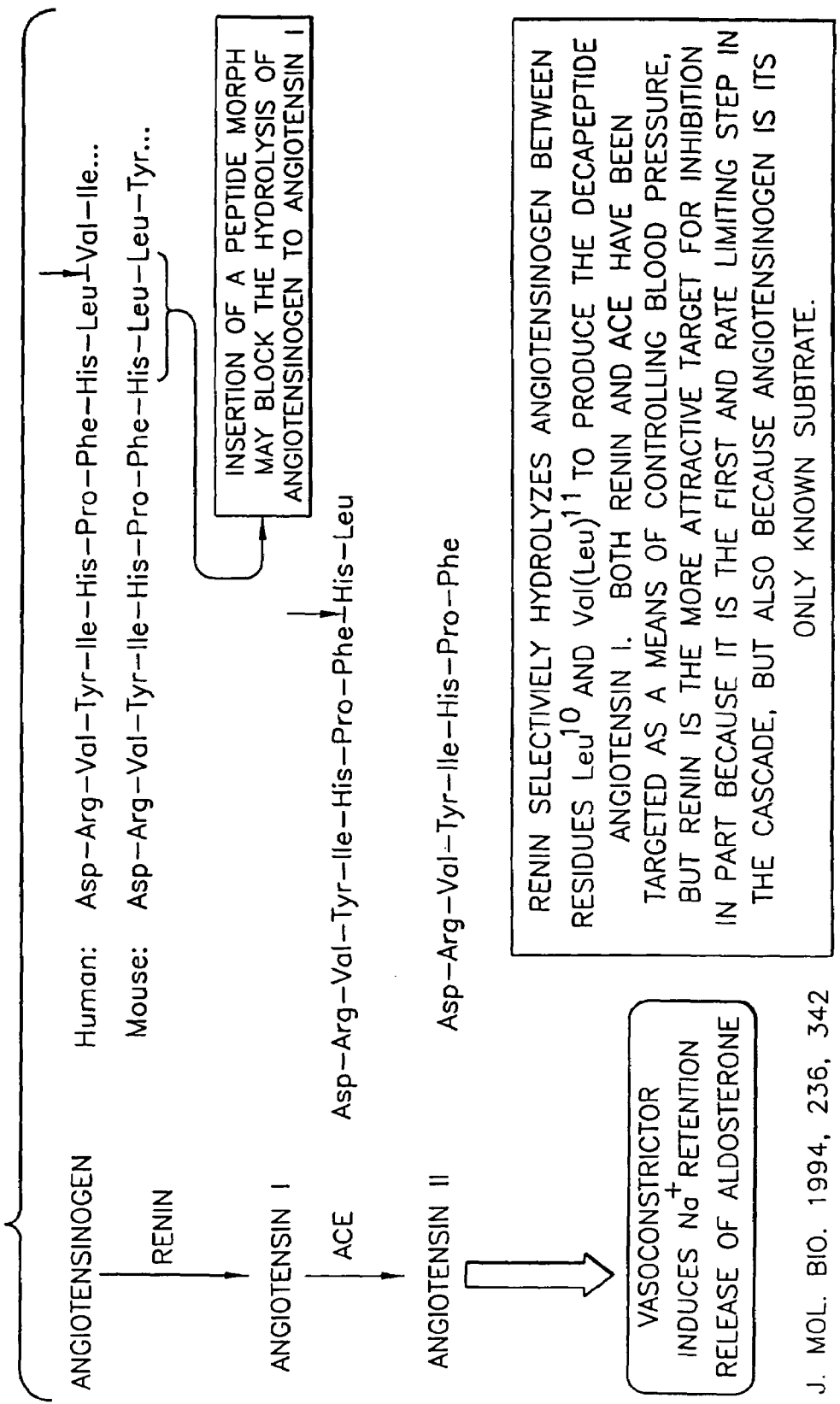
FIG. 30 depicts a use for the compounds and libraries of the present invention in the renin-angiotensin system.
Figure 31:
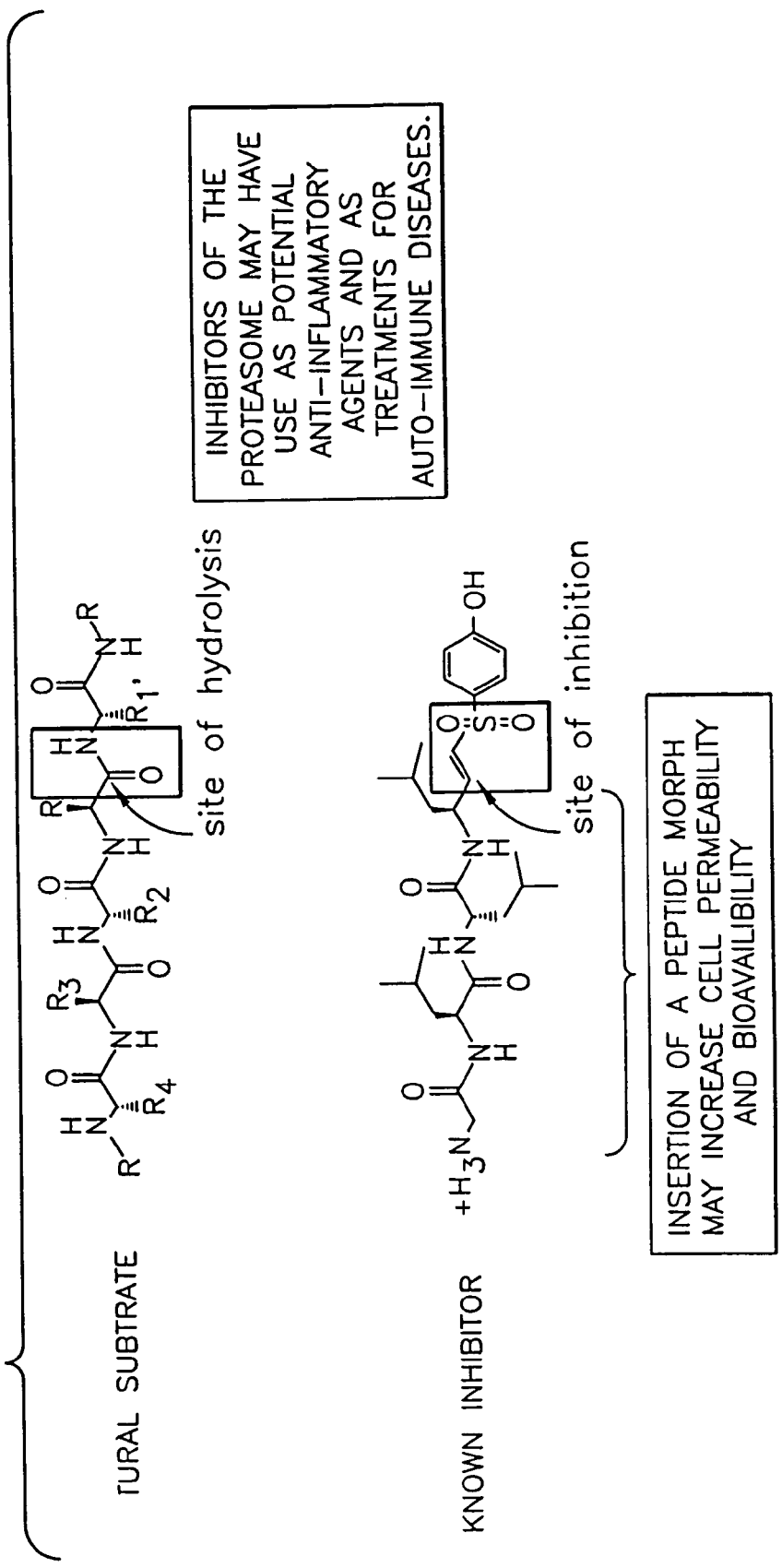
FIG. 31 depicts a use for the compounds and the libraries of the present invention as inhibitors of the proteasome.
Figure 32:
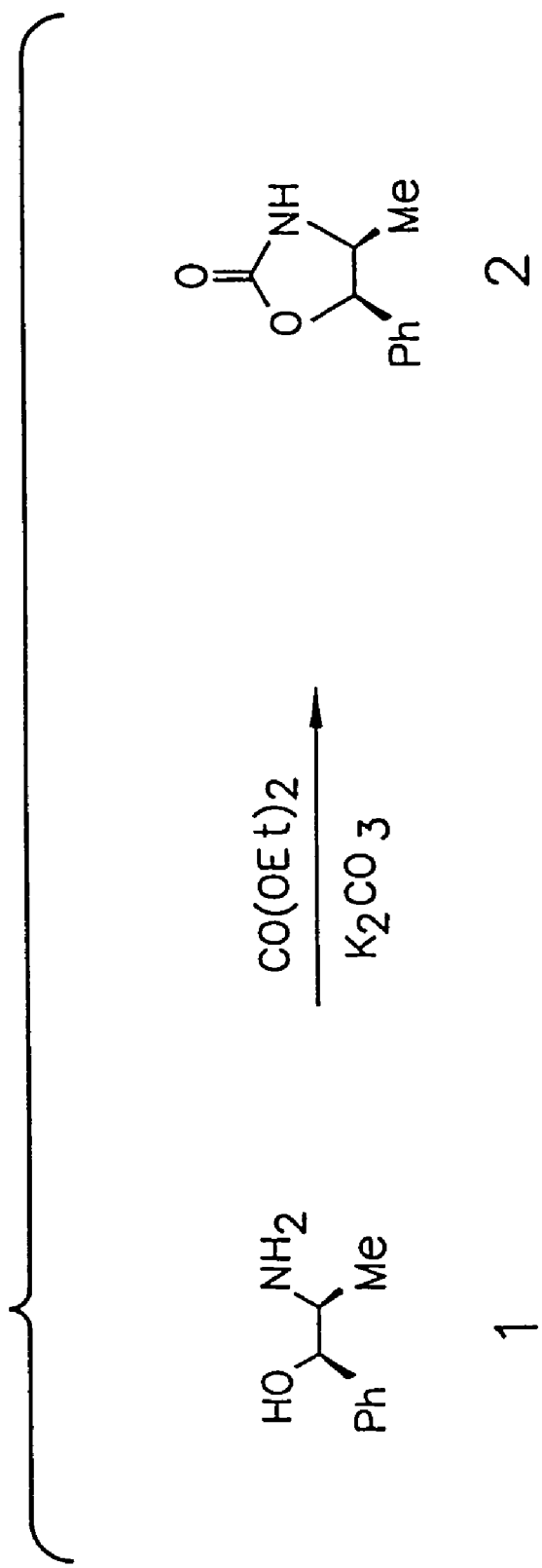
FIG. 32 depicts the synthesis of compound 2.
Figure 33:
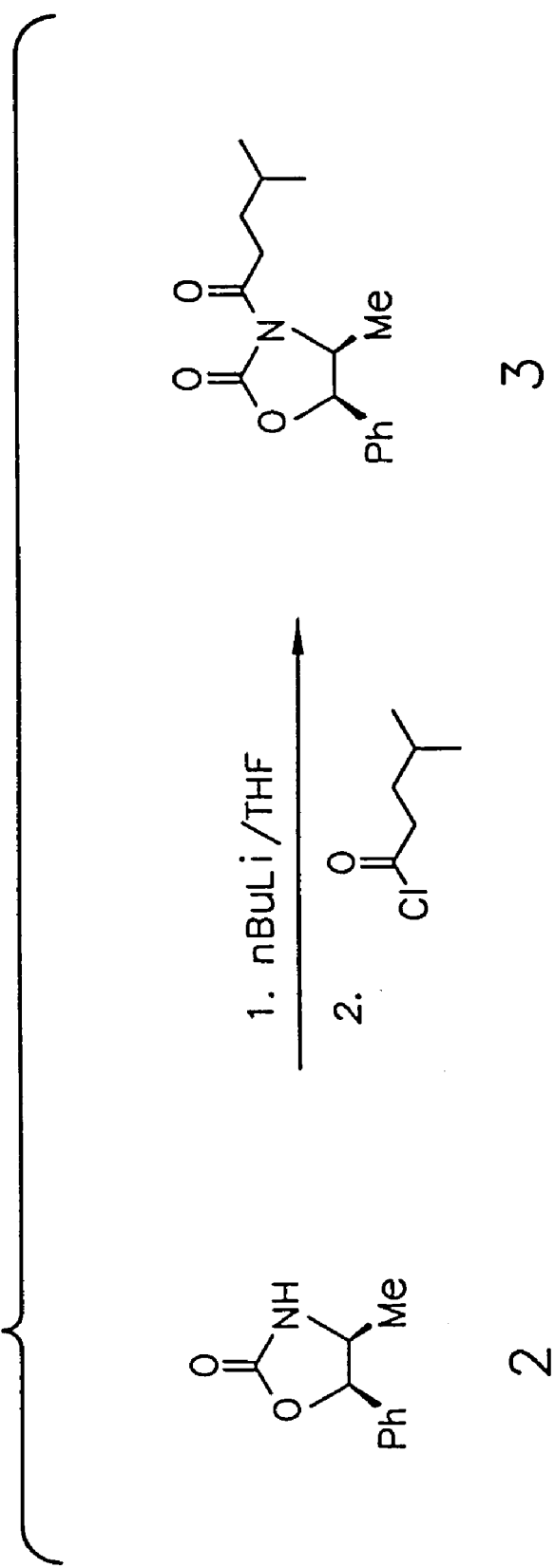
FIG. 33 depicts the synthesis of compound 3.
Figure 34:
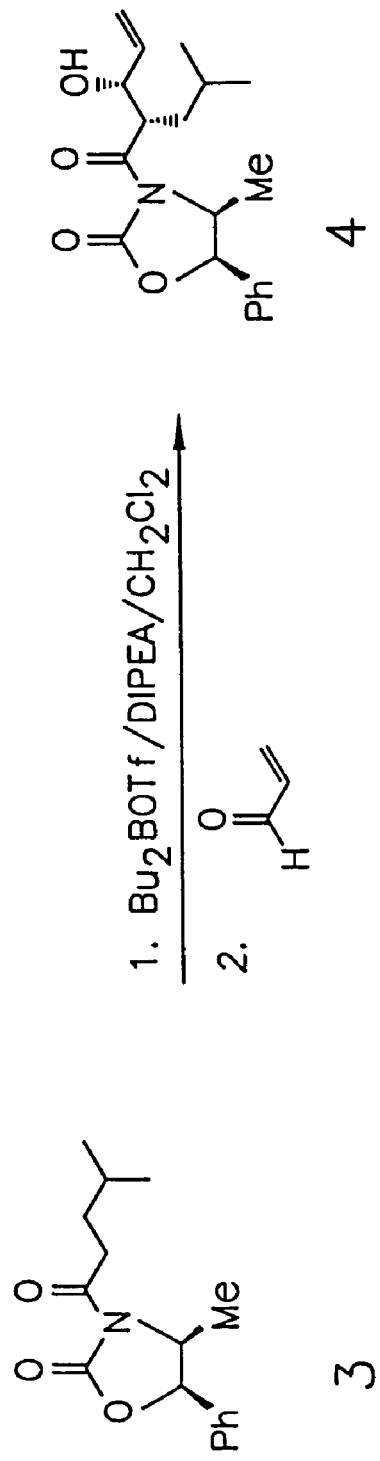
FIG. 34 depicts the synthesis of compound 4.
Figure 35:
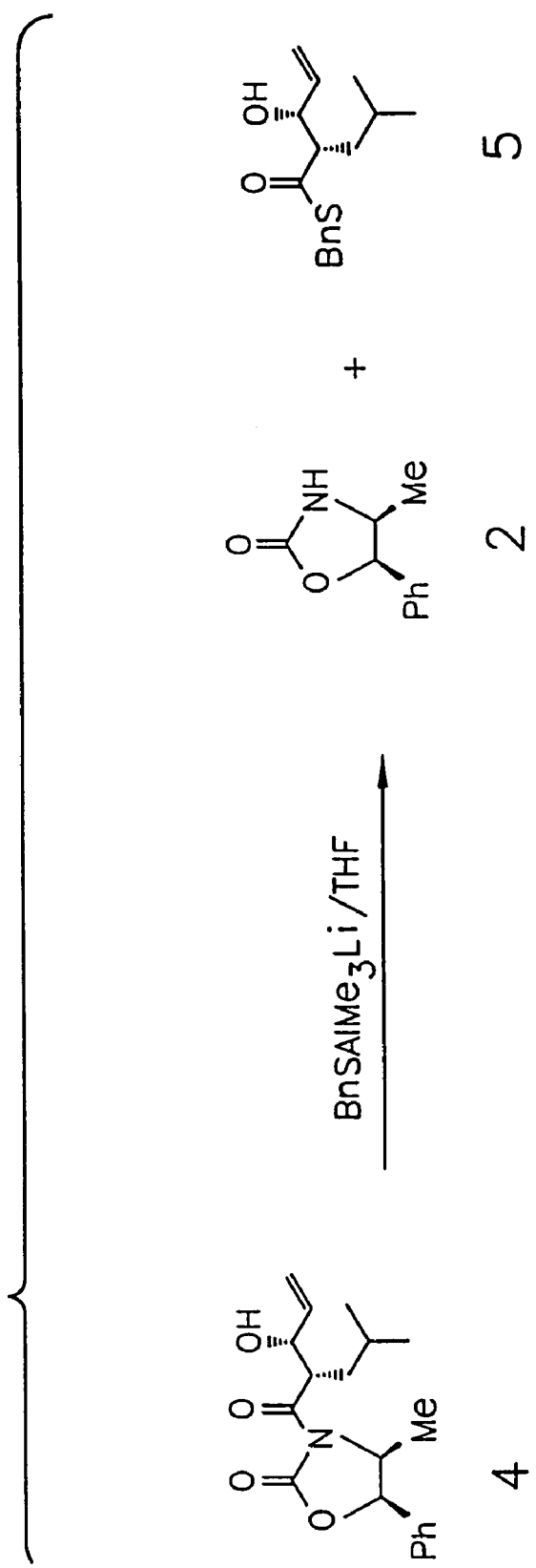
FIG. 35 depicts the synthesis of compound 5.
Figure 36:
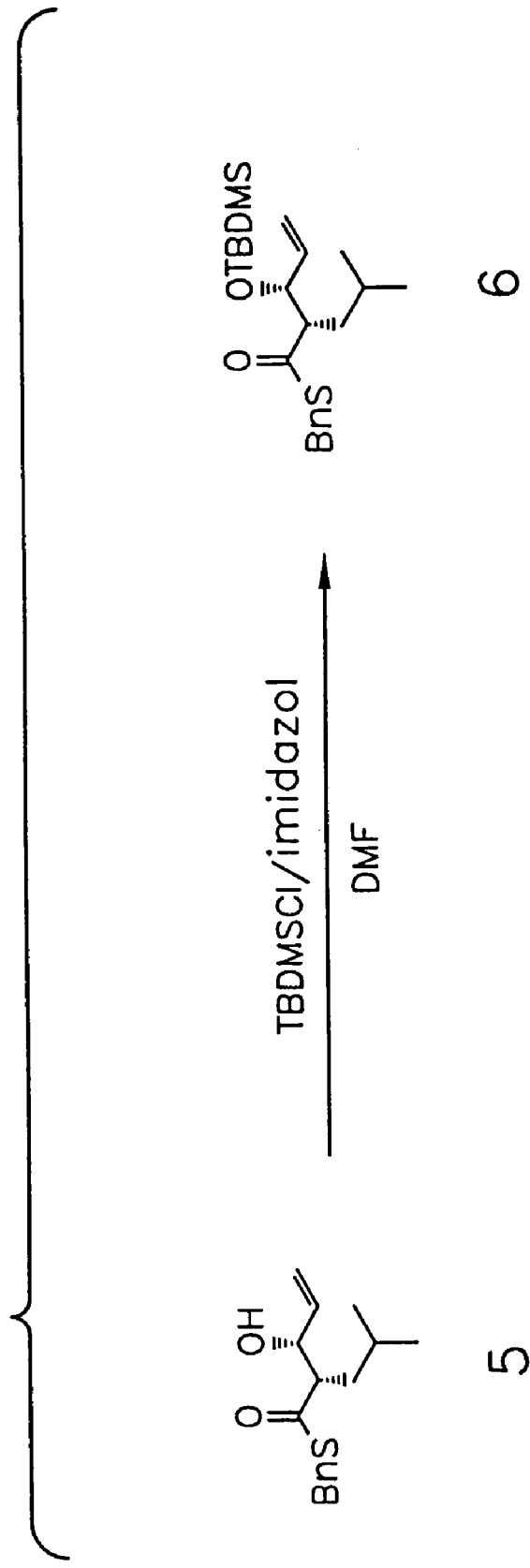
FIG. 36 depicts the synthesis of compound 6.
Figure 37:
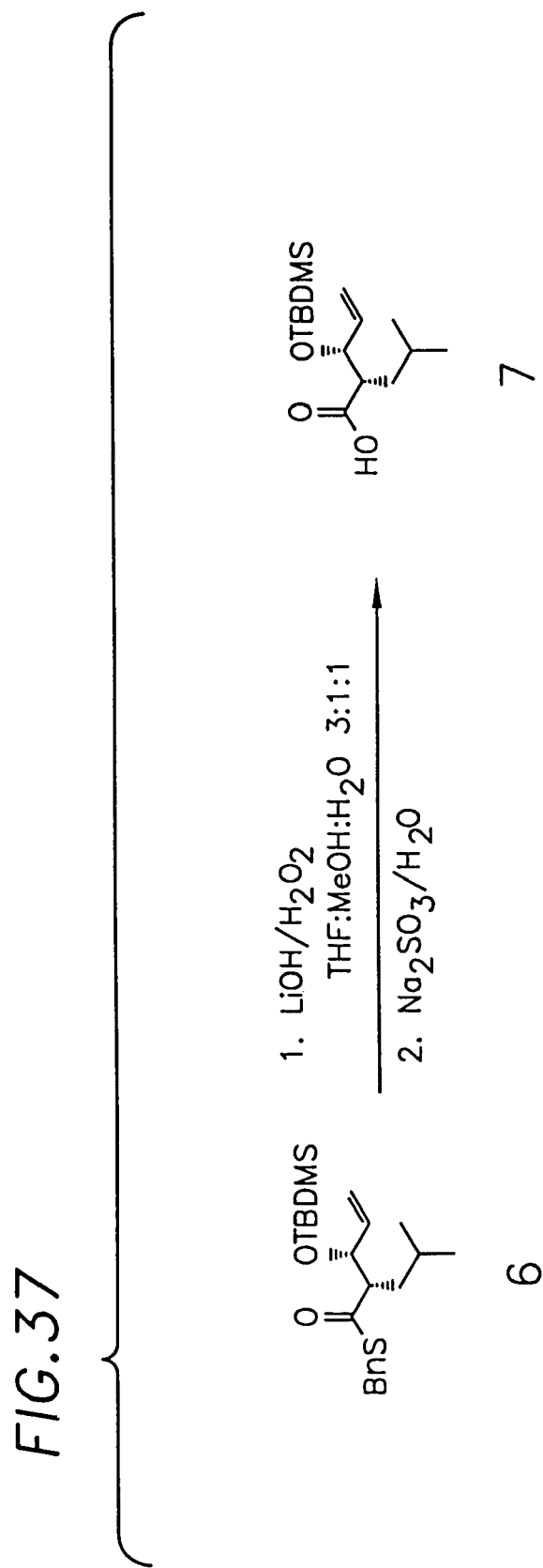
FIG. 37 depicts the synthesis of compound 7.
Figure 38:
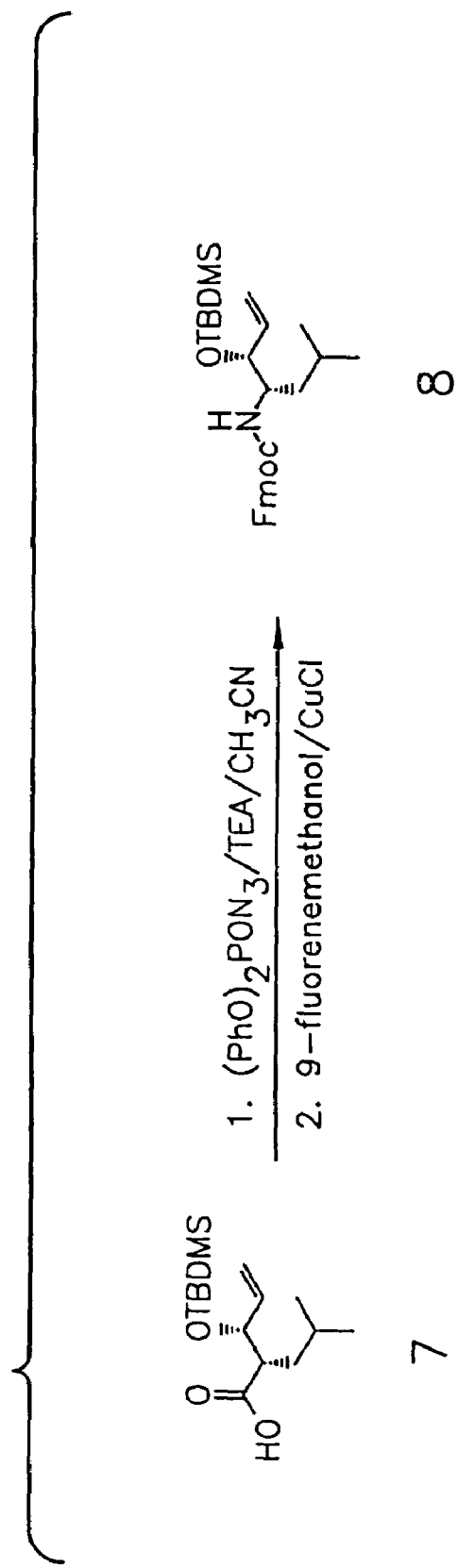
FIG. 38 depicts the synthesis of compound 8.
Figure 39:
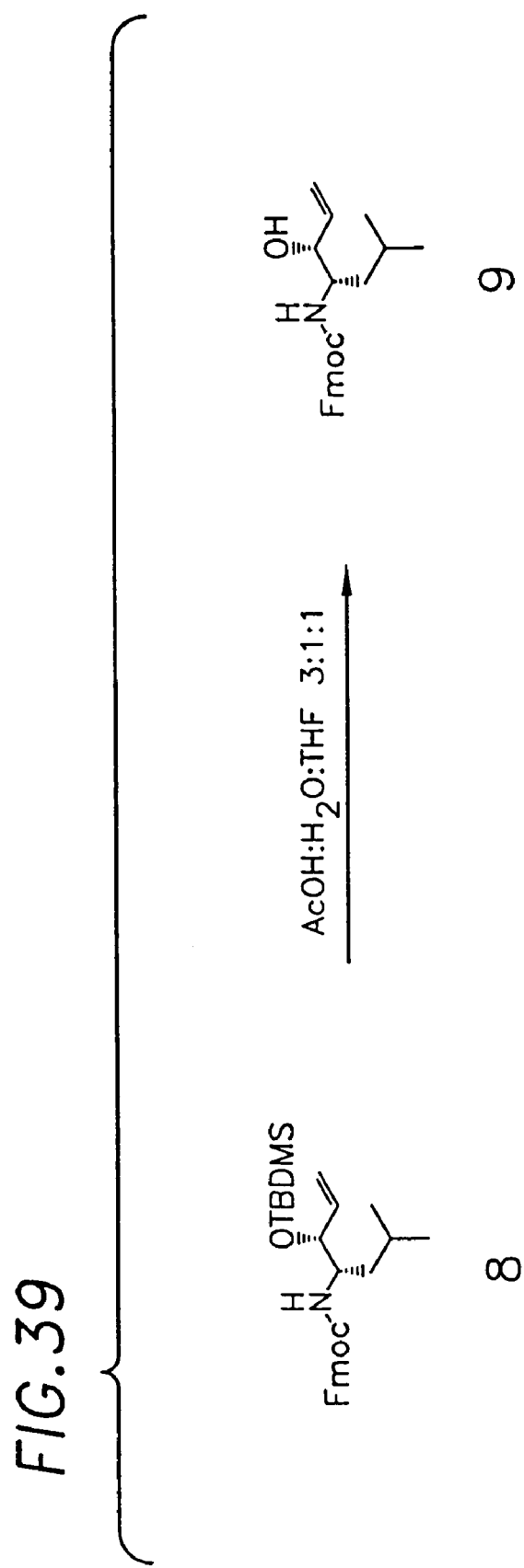
FIG. 39 depicts the synthesis of compound 9.
Figure 40:
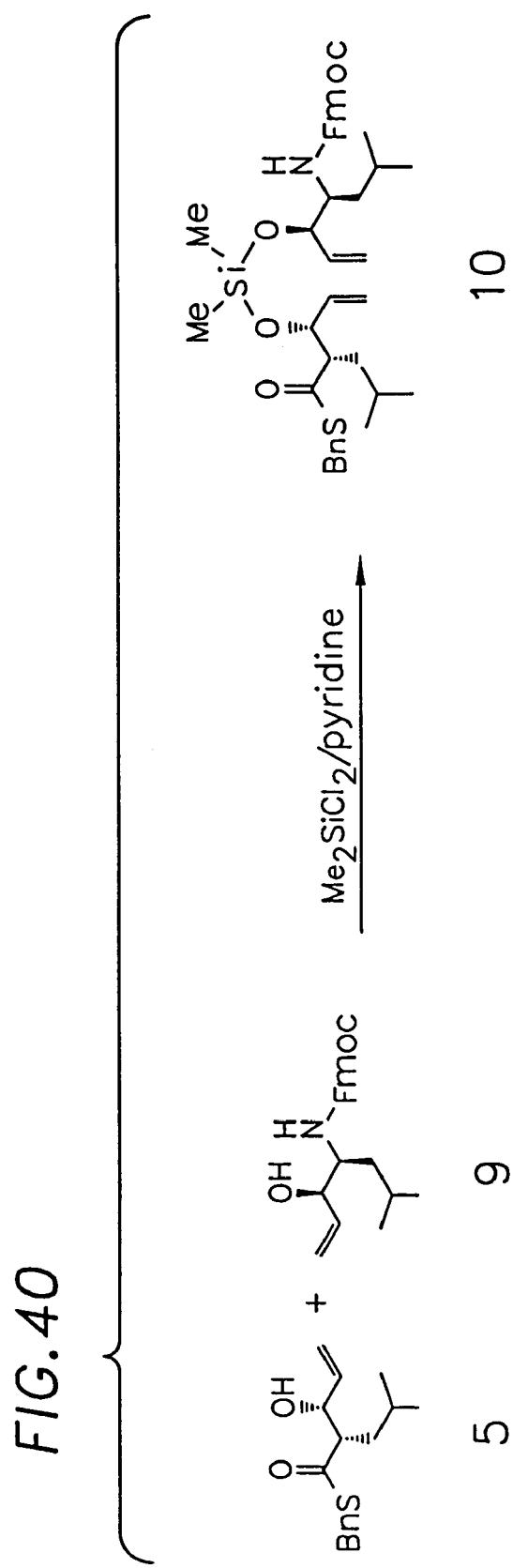
FIG. 40 depicts the synthesis of compound 10.
Figure 41:
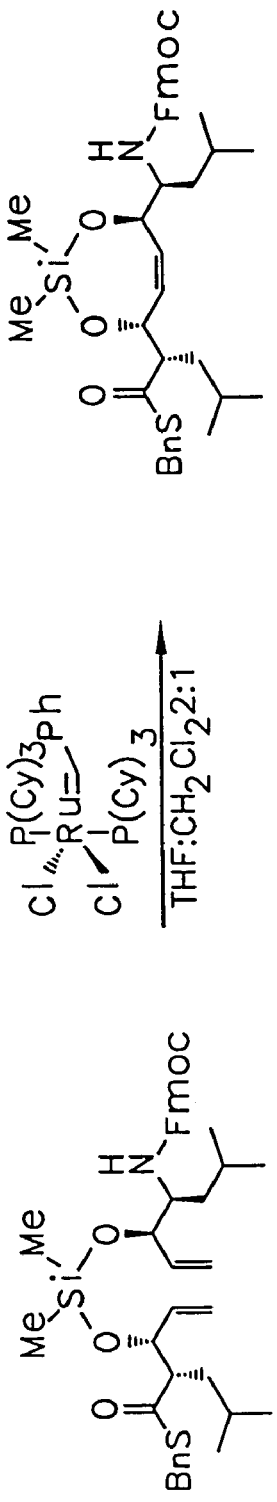
FIG. 41 depicts the synthesis of compound 11.
Figure 42:
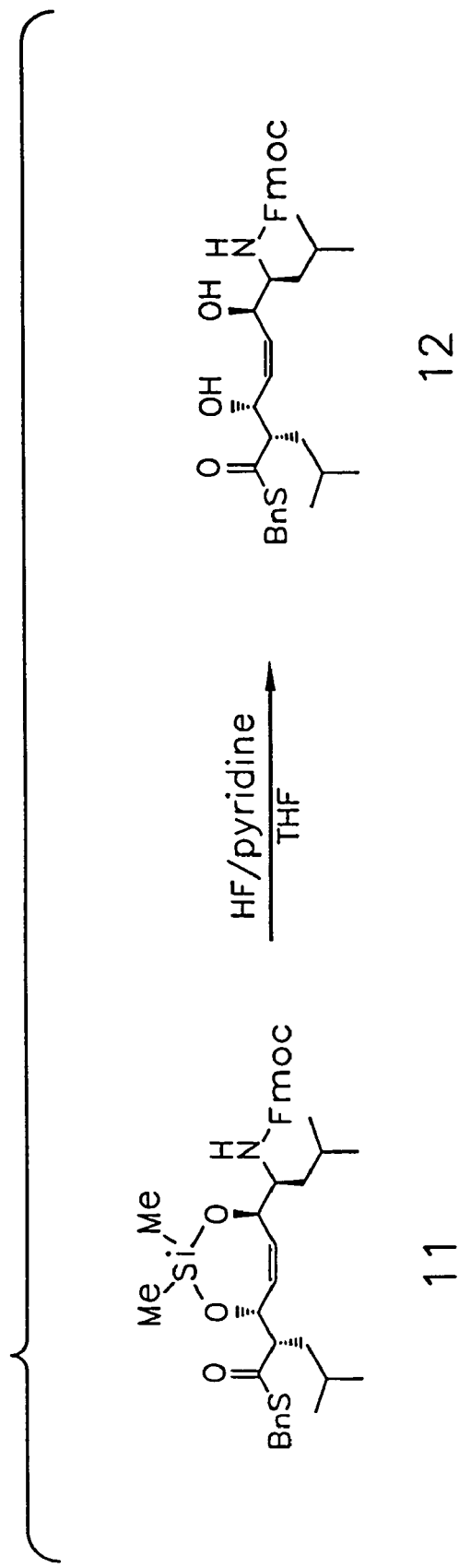
FIG. 42 depicts the synthesis of compound 12.
Figure 43:
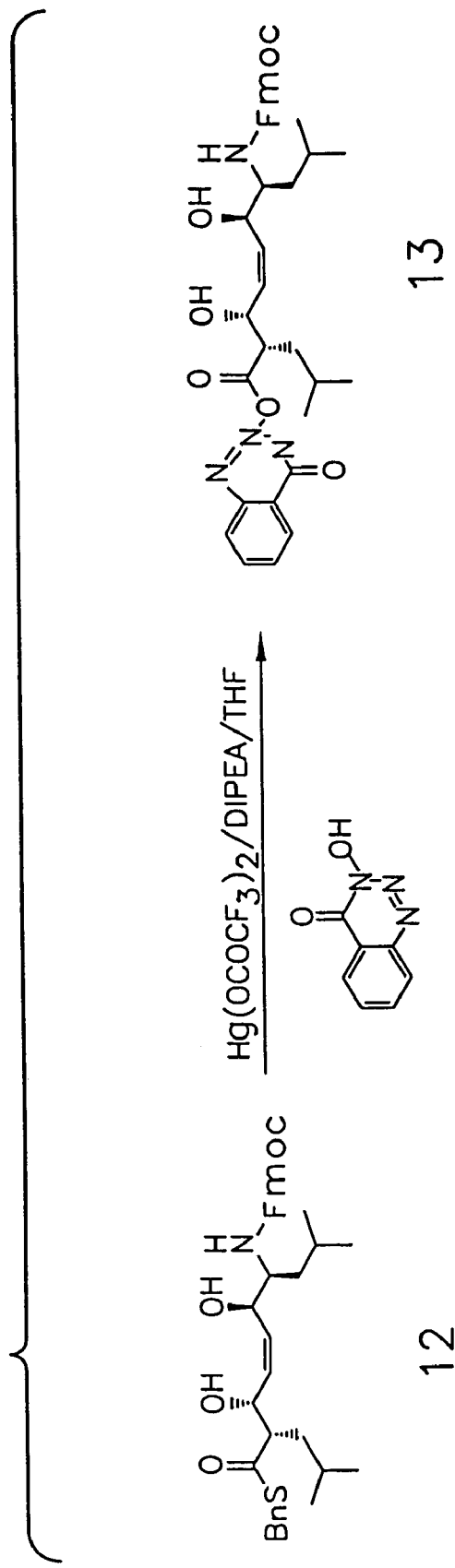
FIG. 43 depicts the synthesis of compound 13.
Figure 44:
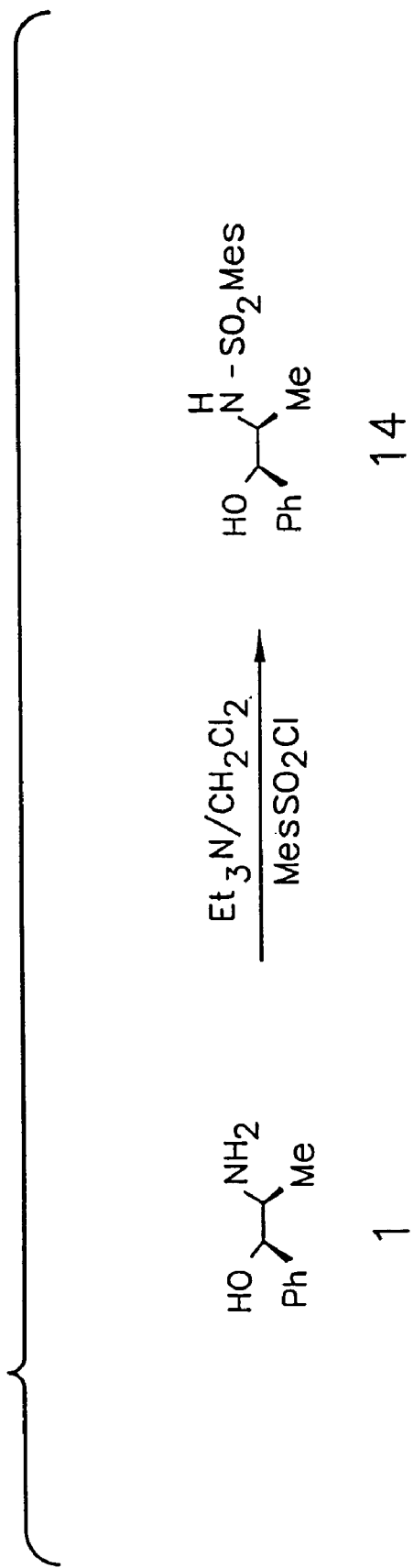
FIG. 44 depicts the synthesis of compound 14.
Figure 45:
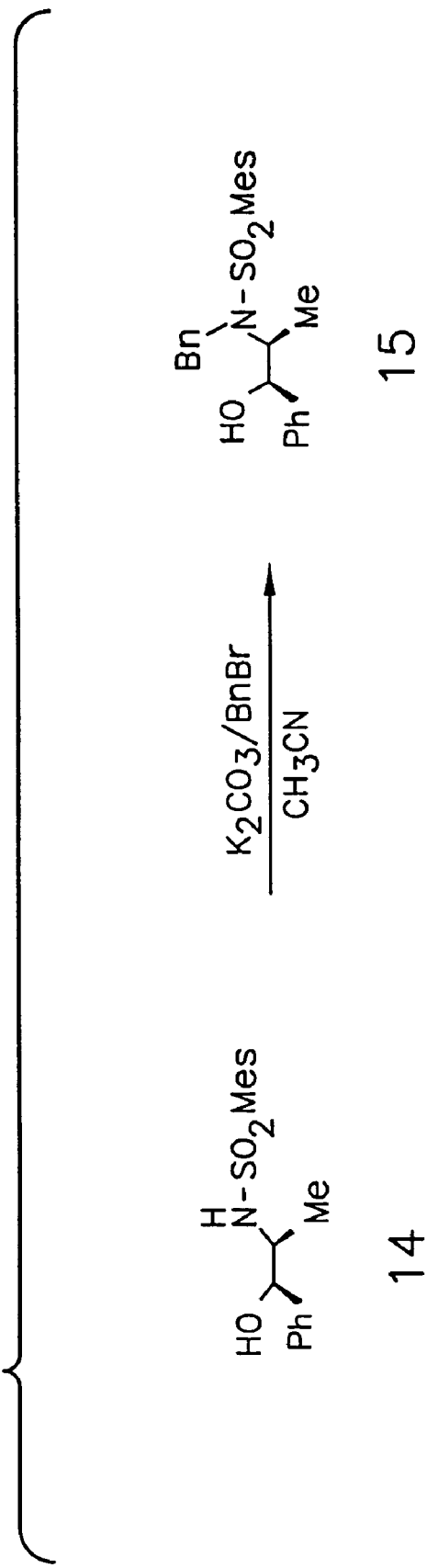
FIG. 45 depicts the synthesis of compound 15.
Figure 46:
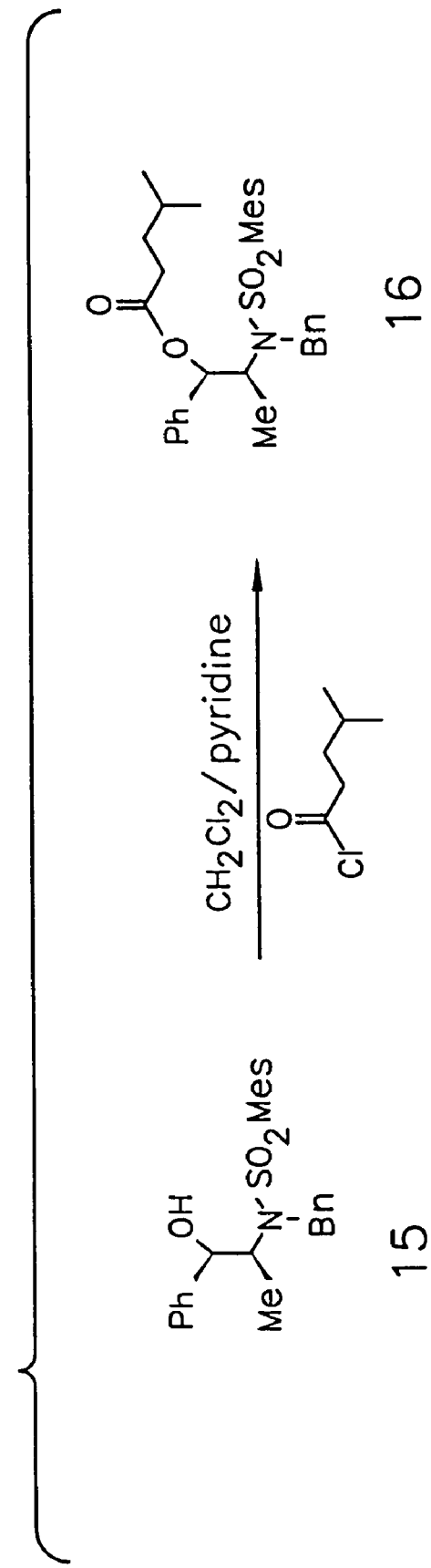
FIG. 46 depicts the synthesis of compound 16.
Figure 47:
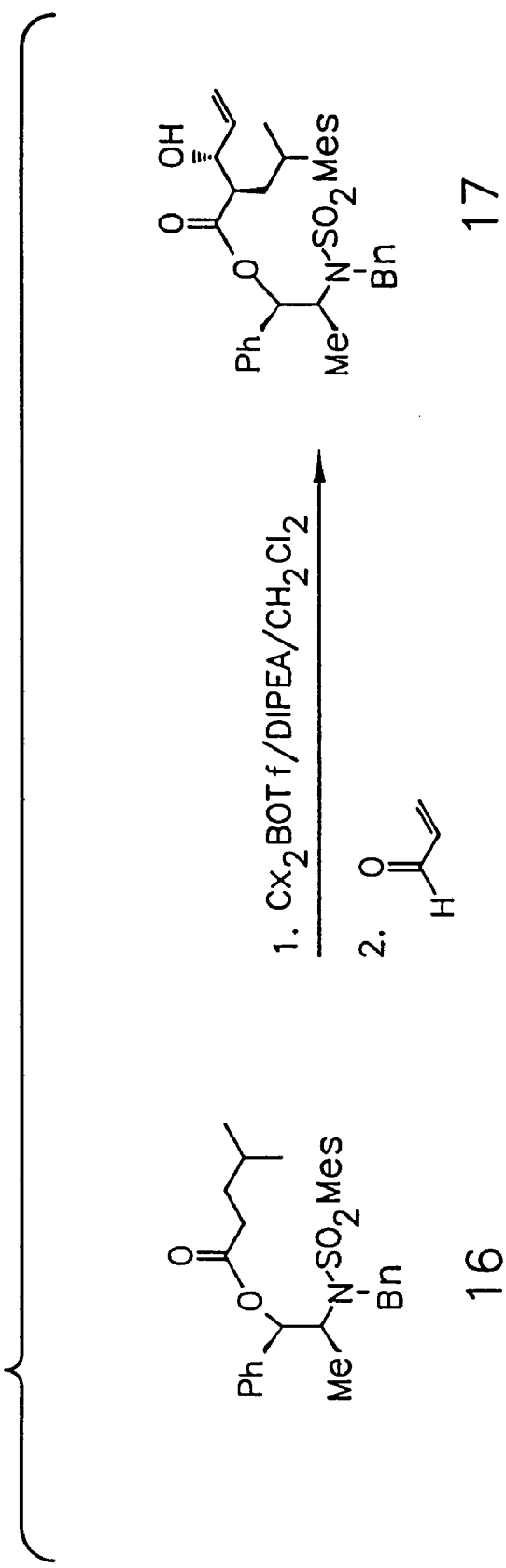
FIG. 47 depicts the synthesis of compound 17.
Figure 48:
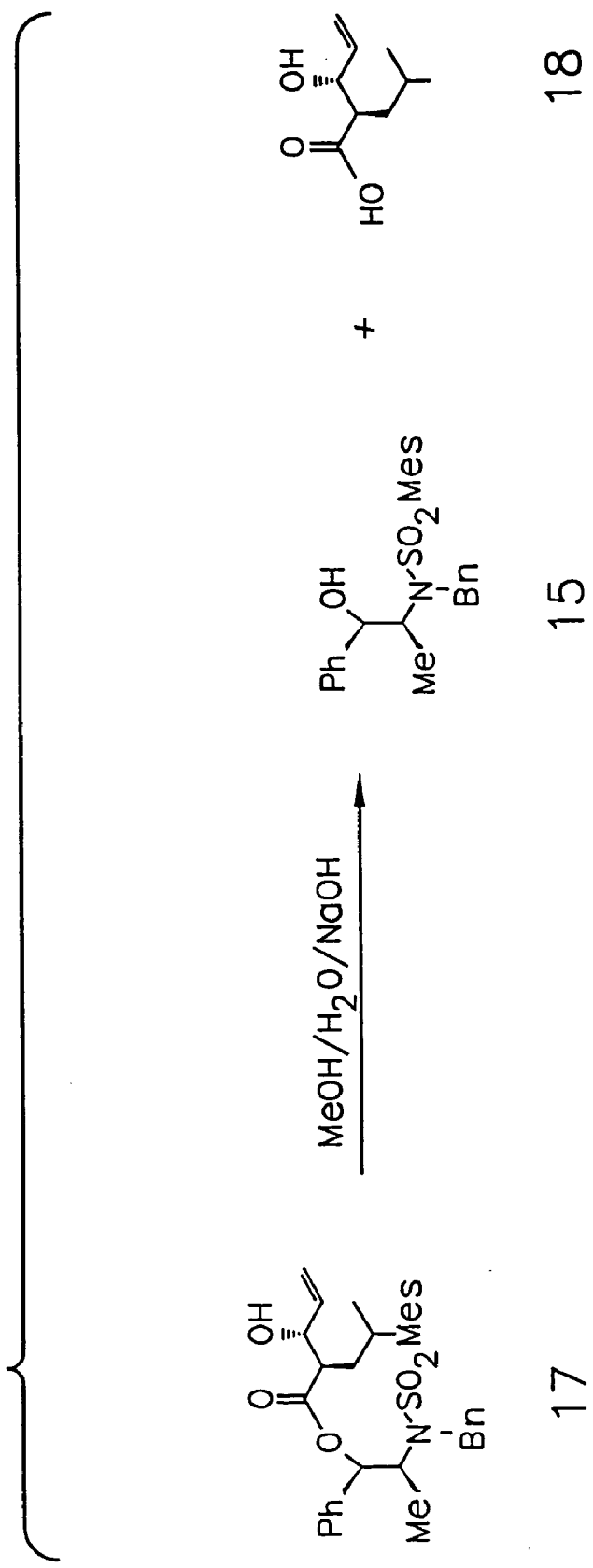
FIG. 48 depicts the synthesis of compound 18.
Figure 49:
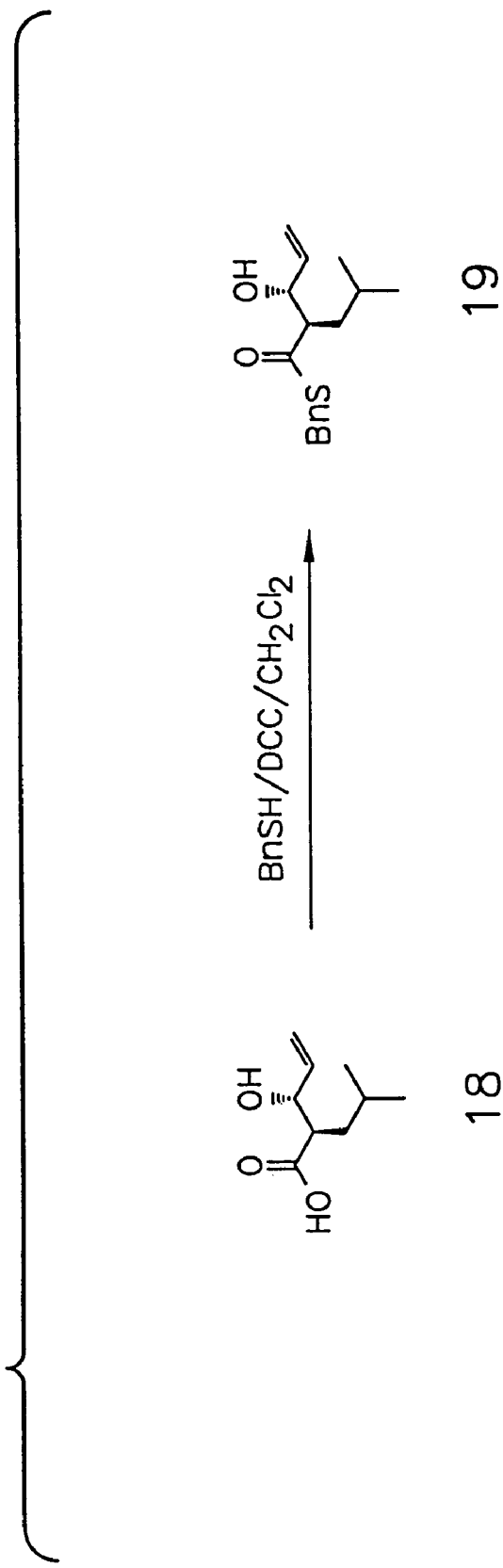
FIG. 49 depicts the synthesis of compound 19.

To give just a few examples, the present invention can be utilized to produce peptidomimetic compounds that control (i.e., promote or inhibit) cell functions. Such compounds may be formulated and utilized as therapeutic pharmaceuticals. For example, such therapeutic pharmaceuticals, through interactions with cellular receptors, can control HLV production, cell proliferation, viral replication, gene expression, or any other cell signaling process. For example, a morphed segment produced according to the present invention can be embedded in a $SH_2$ binding peptide, as shown in FIG. 25. FIG. 26 depicts model studies showing the binding of a morphed peptide to a $SH_2$ domain. In another example, a library of inhibitors of DNA Glycosylases as shown in FIG. 27 can be synthesized according to the method of the present invention. Additionally, a library of synthetic transcriptional regulators can be developed by the attachment of FK506 to the resin linked library of the present invention via an olefin linker as depicted in FIG. 28. Furthermore, FIG. 29 depicts a use for the inventive compounds and libraries in the E6E6-AP system. FIG. 30 depicts a use for the inventive compounds and libraries in the renin-angiotensin system. Finally, FIG. 3 depicts a use for the inventive compounds and libraries as inhibitors of the proteasome.

Inventive peptidomimetic or stereodiverse compounds can alternatively or additionally be used for catalysis, either as a ligand for a transition metal capable of mimicking an important biological environment, or by acting in concert with a particular transition metal catalyst to effect a particular desired enantioselective chemical reaction.

Inventive peptidomimetic or stereodiverse compounds are also useful in the area of materials science. Because of the reactive moieties present at the terminal ends of these compounds, molecules such as lipids and other polymeric molecules may be attached and thus generate potentially important biomaterials.

It will be appreciated by one of ordinary skill in the art that the present invention is not intended to be limited to the abovementioned uses, but rather may be employed in many contexts and disciplines.

EXAMPLES (ILLUSTRATED IN FIGS. 32–49)

Example 1

Norephedrine (compound 1) was purchased from Aldrich (28,255-3, 31,750-0, both enantiomers available) and used as received. Norephedrine (32 g, 211 mmoles) was placed in a flame-dried 250 ml round bottom flask equipped with a stir bar. Diethyl carbonate (60 ml, 422 mmoles) (Aldrich D9,155-1) and $K_2CO_3$ (2.5 g, 21 mmoles) were added and the resulting slurry was heated to 120° C. under a Dean-Stark trap for 16 hours. After that time, the reaction mixture was diluted with methylene chloride and water and extracted (3×) with 300 ml of methylene chloride, dried with anhydrous $MgSO_4$, filtered and concentrated under vacuum. Compound 2 was recrystallized from 1:2 EtOAc/Hexanes. Yield: 34 g (91%).

Example 2

Compound 2 (8.9 g, 50 mmoles) was placed in a 500 ml round bottom flame-dried flask equipped with a stir bar and then dissolved in 150 ml THF. The solution was then cooled to −78° C. and to this solution was added dropwise over a period of five minutes 31.6 ml (50.5 mmoles) of 1.6 M solution of n-BuLi in hexanes (Aldrich 18,617-1). Upon complete addition, 4-methylvaleroyl chloride (Pfaltz & Bauer M30370) was added via syringe. The solution was stirred at −78° C. for 30 minutes and then allowed to warm up to room temperature over 15 minutes. At this time, 100 ml of saturated $NH_4Cl$ was added. The organic solvent was removed under vacuum and the remaining slurry was then extracted (3×) with 250 ml of methylene chloride, dried with anhydrous $MgSO_4$, filtered and concentrated under vacuum. Yield: 14.4 g (105%). Compound 3 was used in the next step without further purification.

Example 3

To a solution of compound 3 (15.4 g, 50 mmol) in 200 ml of methylene chloride cooled down to 0° C. were added dropwise 55.0 ml of 1.0 M solution of dibutylboron triflate in methylene chloride (Aldrich 26,147-5) and redistilled diisopropylamine (10.5 ml, 60 mmol) at a rate such that the internal temperature did not exceed 3.0° C. The resulting clear, colorless solution was cooled down to −78° C. and acrolein (16.7 ml, 250 mmol, Aldrich 11,022-1), dried by pouring through a short plug of neutral aluminum oxide immediately before use) was then added via syringe over a period of five minutes. After stirring for 60 minutes at −78° C., the reaction was quenched by adding 200 ml of 5:1 $MeOH/H_2O_2$, which was precooled to 0° C., and stirred for another 10 minutes at −78° C. and then 30 minutes at 0C. The reaction volume was reduced by removing the organic solvents under vacuum, 300 ml of methylene chloride and 300 ml of 5% $NaHCO_3$ were added and the product was extracted (3×) with methylene chloride, dried with anhydrous $MgSO_4$, filtered and concentrated under vacuum.

Yield: 22.0 g (133%). The crude compound 4 was used in the next step without further purification.

Example 4

In a flame-dried round bottom flask equipped with a stir bar, benzylmercaptane (11.3 ml, 100 mmol, Aldrich B2,540-1) was dissolved in 75 ml of THF and the solution was cooled to 0° C. and 1.6 M solution of n-BuLi in hexanes (62.5 ml, Aldrich 18,617-1) was added dropwise over a period of five minutes. To that solution, 2.0 M solution of AlMe$_3$ in toluene (50.0 ml, Aldrich 19,804-8) was added dropwise over a period of five minutes. The reaction was allowed to stir for an additional 30 minutes at 0° C. and the solution of BnSAlMe$_3$Li was added dropwise via cannula. The reaction was stirred for 120 minutes at 0° C., carefully quenched with 200 ml of 1.0 M aqueous solution of HCl (vigorous foaming) at 0° C. and then stirred for an additional 30 minutes at room temperature. The reaction was extracted (3×) with 200 ml of EtOAc, dried with anhydrous MgSO$_4$, filtered and concentrated under vacuum. Compounds 2 and 5 in the crude reaction mixture were separated by precipitating compound 13 from neat hexanes. The hexane solution of compound 5 was concentrated under vacuum and purified by flash chromatography in 7:1 Hexanes/EtOAc+0.2% MeOH. Yield: 8.0 g (58% over the last three steps). Compound 2 was recrystallized from 1:2 hexanes/EtOAc. Yield: 6.1 g (68%).

Example 5

In a 25 ml flame-dried round-bottom flask equipped with a stir bar, compound 5 (4.50 g, 16 mmol) was dissolved in 4.0 ml of DMF and to this solution was added TBDMSCl (3.0 g, 20 mmoles, Aldrich 19,050-0) and imidazole (2.2 g, 32 mmoles, Aldrich 43,615–1). The reaction was allowed to stir for 14 hours at room temperature. After this time, the reaction was quenched by the addition of 30 ml of saturated aqueous NaHCO$_3$ and extracted (3×) with methylene chloride, dried with anhydrous MgSO$_4$, filtered and concentrated under vacuum. Yield: 6.9 g 110%). Compound 6 was used in the subsequent step without further purification.

Example 6

In a 500 ml round-bottom flask equipped with a stir bar, compound 6 (5.31 g, 13 mmoles) was dissolved in 160 ml of THF, 50 ml of MeOH and 50 ml H$_2$O. The solution was cooled down to 0° C. and 1.2 g of LiOH and 9.0 ml of 30% H$_2$O$_2$ was added, respectively. The reaction was allowed to warm up to room temperature and, after 8 hours at room temperature, it was quenched by addition of 1.0 M aqueous solution of Na$_2$SO$_3$ (156 ml, Aldrich 20,784-5) at 0° C. and stirred at room temperature for an additional 30 minutes. The reaction was acidified to pH=2 by adding 200 ml of 1.0 M KHSO$_4$ (pH of the aqueous layer was checked by using pH paper strips). The reaction was extracted (3×) with methylene chloride, dried with anhydrous MgSO$_4$, filtered and concentrated under vacuum. Yield: 4.8 g (105%). Compound 7 was used in the subsequent step without further purification.

Example 7

REFERENCE: Synthesis 131, (1989)
In a 250 ml flame-dried round-bottom flask equipped with a stir bar compound 7 (4.8 g, 16 mmoles) was dissolved in 80 ml of distilled acetonitrile. To this solution, freshly distilled TEA (2.5 ml, 18 mmoles) was added followed by diphenylphosphoryl azide (3.8 ml, 18 mmoles, Aldrich 17,875-6). A condenser was placed on the flask and the reaction was refluxed for 30 minutes at 85° C. The reaction was then cooled to room temperature and CuCl (0.4 g 4 mmoles, Aldrich 22,962-8) was added followed by 9-fluorenemethanol (9.4 g, 48 mmoles. Aldrich 16,050-4). The reaction was stirred for additional 120 minutes at room temperature and quenched by addition of 100 ml of saturated NaHCO$_3$. The reaction was extracted (3×) with EtOAc, dried with anhydrous MgSO$_4$, filtered and concentrated under vacuum. The crude product was purified by flash chromatography (19:1 hexanes/EtOAc+0.2% MeOH). Yield: 3.6 g (47%).

Example 8

REFERENCE: JACS 94, 6195, (1972)
In a 250 ml round-bottom flask equipped with a stir bar, compound 8 (3.6 g, 7.5 mmoles) was dissolved in 45 ml of AcOH, 15 ml of H$_2$O and 15 ml of THF and stirred at 45° C. for 4 hrs. After that time, the solvent was removed under vacuum by azeotropic distillation with toluene and the crude product was purified by flash chromatography (4:1 Hexanes/EtOAc+0.2% MeOH). Yield: 2.0 g (73%).

Example 9

REFERENCE: JACS 113, 9661, (1991)
A 25 ml flame-dried round bottom flask was charged with freshly distilled dimethyldichlorosilane (2.4 ml, 20 mmoles, Aldrich 44,027-2) and 5 ml of freshly distilled pyridine were added. In a separate flask, compound 5 (278 mg, 1 mmole) was dissolved in 2.0 ml of freshly distilled pyridine and transferred via cannula to the solution of dimethyldichlorosilane in pyridine. The flask was then washed with another 0.5 ml of pyridine and the reaction was stirred for 2 hrs at room temperature. After that time, a short-path distillation head was placed on the flask and excess dichlorodimethylsilane and pyridine were removed under high vacuum. To the resulting slurry, compound 9 (365 mg, 1 mmole) dissolved in a separate flask in 9 ml of freshly distilled pyridine was transferred via cannula and the reaction was stirred for another 2 hours at room temperature. The excess of pyridine was removed under high vacuum. 20 ml of saturated NaHCO$_3$ were added and the reaction was extracted (3×) with EtOAc, dried with anhydrous MgSO$_4$, filtered and concentrated under vacuum. The crude product was purified by flash chromatography (15:1 hexanes/EtOAc+0.2% MeOH). Yield: 427 mg (61%).

Example 10

A 25 ml flame-dried round-bottom flask was charged with compound 11 (427 mg. 0.61 mmoles) and 6 ml of distilled THF were added. A reflux condenser was placed on the flask and the system was flushed with argon. In a separate flask, the Grubbs' catalyst (255 mg, 0.31 mmoles, Strem 44–0065) was dissolved in 3.0 ml of freshly distilled methylene chloride and transferred via cannula to the flask containing compound 12 which was then heated to 40° for 24 hours. After that time, another portion of the Grubbs' catalyst (255 mg, 0.31 mmoles dissolved in 3.0 ml of freshly distilled dichloromethane) was added via cannula and the heating was continued for another 24 hours. The reaction was then concentrated under vacuum and purified by flash chromatography (12:1 hexanes/EtOAc+0.2% MeOH). Yield: 116 mg (28%), recovered starting material: 185 mg (43%). The recovered starting material was resubjected to the same metathesis conditions with the same percentage yield of the product. Additionally, this metathesis reaction can be now carried out with 5% mol percent of the new catalyst (Grubbs et al., Tet. Lett., 1999, 40, 2247; Nolan et al., accepted for publication in *J. Am. Chem. Soc.*). This improved catalyst greatly increases the efficiency of the metathesis reaction.

Example 11

In a 50 ml Corning plastic test tube, compound 11 (166 mg, 0.25 mmoles) was dissolved in 1 ml of THF and cooled down to 0° C. A solution of HF in pyridine (71 ml, 2.5 mmoles, Aldrich 18,422-5) was added dropwise, the reaction was allowed to warm up to room temperature and stirred for additional 30 minutes at room temperature. After that time, the reaction was carefully quenched with 10 ml of 1.0M $Na_2CO_3$ (vigorous foaming), extracted (3×) with EtOAc, dried with anhydrous $MgSO_4$, filtered and concentrated under vacuum. The crude product was purified by flash chromatography (3:1 hexanes/EtOAc+1.0% MeOH). Yield: 85 mg (50%). Note: The low yield is most likely caused by the residual catalyst decomposition products increasing the weight of compound 11 before the deprotection.

Example 12

In a 5 ml flame-dried pear-shaped flask, compound 12 (106 mg, 0.13 mmoles) was dissolved in 1.3 ml of THF. To that solution, DIPEA (46 ml, 0.26 mmoles) and $Hg(O-COCF_3)_2$ (111 mg, 0.26 mmoles, Aldrich 15,648-5) were added, respectively and the resulting yellow solution was stirred for another 30 minutes at room temperature. After that time, the reaction was concentrated under vacuum and the crude product (compound 13) purified by flash chromatography (1:1 hexanes/EtOAc+1.0% MeOH). Yield: 55 mg (65%).

Example 13

REFERENCE: JACS (1997), 119, 2586

Norephedrine (compound 1) was purchased from Aldrich (28,255-3, 31,750-0, both enantiomers available) and used as received. Norephedrine (7.6 g, 50 mmoles) was placed in a flame-dried 500 ml round-bottom flask equipped with a stir bar, dissolved in 200 ml of freshly distilled methylene chloride and cooled down to 0° C. Freshly distilled $Et_3N$ (8.3 ml, 60 mmoles) was added slowly over a period of 5 minutes and then 2-mesitylenesulfonyl chloride (Aldrich M770-7, 11.0 g, 50 mmoles) dissolved in 25 ml of freshly distilled methylene chloride was added slowly via cannula over a period of 5 minutes. The reaction mixture was allowed to warm to room temperature and stirred for another 4 hours. After that time, the reaction mixture was extracted (3×) with EtOAc, dried with anhydrous $MgSO_4$, filtered and concentrated under vacuum. The crude product (compound 14) was recrystallized from methylene chloride:hexane. Yield: 15.7 g (94%).

Example 14

REFERENCE: JACS (1997). 119, 2586

Compound 14 (15.7 g, 47 mmoles) was placed in a 500 ml round-bottom flame-dried flask equipped with a stir bar and then dissolved in 188 ml freshly distilled acetonitrile. To that solution, $K_2CO_3$ (9.7 g, 71 mmoles) and benzyl bromide (Aldrich B1,790–5, 6.8 ml, 56 mmoles) were added, respectively. The flask was equipped with a reflux condenser and refluxed for 36 hours. After that time, the reaction was quenched with 20 ml of saturated $NH_4Cl$ extracted (3×) with EtOAc, dried with anhydrous $MgSO_4$, filtered and concentrated under vacuum. The crude product (compound 15) was purified by flash chromatography (6:1→4:1 hexanes: EtOAc+0.2% MeOH gradient). Yield: 17.7 g (89%).

Example 15

REFERENCE: JACS (1997), 119, 2586

Compound 15 (4.2 g, 10 mmoles) was placed in a 200 ml round-bottom flame-dried flask equipped with a stir bar, dissolved in 43 ml of freshly distilled methylene chloride and cooled down to 0° C. Freshly distilled pyridine (1.1 ml, 13 mmoles) was dropwise and after 10 minutes 4-methylvaleroyl chloride (Pfaltz & Bauer M30370, 1.6 ml, 12 mmoles) was added dropwise via syringe. The reaction was allowed to warm to room temperature and stirred for another 16 hours. After that time, the reaction mixture was extracted (3X) with EtOAc, dried with anhydrous $MgSO_4$. filtered and concentrated under vacuum. The crude product (compound 16) was used in the subsequent step without further purification. Yield: 5.6 g (108%).

Example 16

REFERENCE: JACS (1997), 119, 2586

Compound 16 (5.6 g, 10 mmoles) was placed in a 250 ml round-bottom flame-dried flask equipped with a stir bar, dissolved in 75 ml of freshly distilled methylene chloride and cooled down to 0° C. and freshly distilled $Et_3N$ was added via syringe. The reaction mixture was cooled down to −78° C. and a precooled 1.0 M solution of $Cx_2BOTf$ in methylene chloride (20 ml, 20 mmoles—prepared as described in JOC (1992), 57, 499 and JOC (1993), 58, 147) was added slowly via cannula over a period of five minutes. The reaction was stirred for additional 2 hours at −78° C. after which time acrolein (0.8 ml, 12 mmoles. Aldrich 11.022–1, dried by pouring through a short plug of neutral aluminum oxide immediately before use) was added via syringe and the reaction was stirred for another hour at −78° C. and then for another hour at 0° C. After that time, the reaction was quenched by adding 40 ml of 1.0M phosphate buffer (pH=7.0). 100 ml of MeOH and 10 ml of 30% $H_2O_2$ and stirred for 1 hour at room temperature. The quenched reaction was extracted (3×) with methylene chloride, dried with anhydrous $MgSO_4$, filtered and concentrated under vacuum. The crude product (compound 17) was purified by flash chromatography in 6:1 hexanes:EtOAc+0.2 MeOH. Yield: 5.2 g (90%).

Example 17

REFERENCE: TL (1986), 27, ,1735

Compound 17 (5.2 g, 9 mmoles) was placed in a 200 ml round-bottom flask and dissolved in 72 ml of methanol. To that solution, NaOH (1.8 g, 45 mmoles) dissolved in 18 ml of water was added slowly and the resulting cloudy solution was stirred for additional 14 hours at room temperature. After that time, methanol was removed on rotatory evaporator, 200 ml of water was added to the resulting slurry and the clear solution was extracted (3×) with EtOAc. The organic layer was dried with anhydrous $MgSO_4$, filtered and concentrated under vacuum. The crude compound 15 was recrystallized from methylene chloride: hexane. Yield: 3.4 g (90%). The aqueous layer was acidified to pH=1 by adding concentrated HCl and extracted (3×) with EtOAc dried with anhydrous $MgSO_4$, filtered and concentrated under vacuum. Compound 18 was used in the subsequent step with further purification. Yield: 1.2 g (80%).

Example 18

Compound 18 (1.2 g, 7 mmoles) was dissolved in 3 ml of freshly distilled methylene chloride and benzylmercaptane (2.4 ml, 22 mmoles, Aldrich B2,540–1) was added. The solution was cooled down to 0° C. and 1.0M solution of DCC in methylene chloride (7.9 ml, 7.9 mmoles. Aldrich 37,911-5) was added dropwise via syringe and stirred for another 5 minutes at 0° C. After that time, the reaction was warmed up to room temperature and stirred for additional 2 hours. The reaction mixture was then diluted with $Et_2O$, filtered through a short plus of Celite and concentrated under vacuum. The crude product (compound 19) was purified by flash chromatography in 8:1 hexanes:EtOAc+0.2 MeOH. Yield: 1.5 g (75%).

What we claim is:

1. A method for generating a compound having at least one biological activity of a peptide comprising:
   providing a first monomer, wherein said first monomer is diversifiable and contains first and second terminal reactive moieties, $L_{11}$ and $L_{12}$, respectively, and at least one functionalizable group $R_1$, $R_2$, $R_3$, $X_1$, $X_3$, L, $L_{11}$ or $L_{12}$;
   providing a second monomer, wherein said second monomer is diversifiable and contains third and fourth terminal reactive moieties, $L_{21}$ and $L_{22}$, respectively, and at least one second functionalizable group $R_1$, $R_2$, $R_3$, $X_2$, $X_4$, L, $L_{21}$ or $L_{22}$;
   wherein the first monomer is of the formula

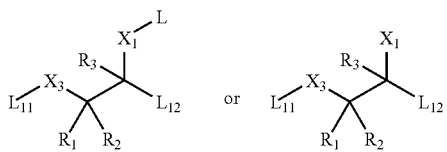

wherein $L_{11}$ and $L_{12}$ are each independently selected from hydrogen, protecting group, alkene, alkyne, amine, carboxylic acid, halogenated aromatic, aldehyde, vinyl halide; $R_1$, $R_2$ and $R_3$ are selected from the group consisting of hydrogen, alkyl, aryl, phenoxy, methoxy, halide, methylene cyclohexyl, benzyl, heteroaryl, aryloxy, carboxyl, carboxalkyl, carboxaryl, arylalkyl, thiol and hydroxyl; L comprises a linking group; $X_3$ comprises a functional moiety selected from carboxyl, amino, gem-dialkyl, and methylene; and $X_1$ comprises a functionality containing oxygen, sulfur or carbon, having a predefined stereochemical relationship, wherein the second monomer is of the formula

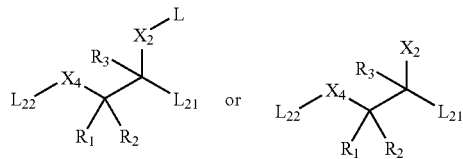

wherein $L_{21}$, and $L_{22}$ are each independently selected from hydrogen, protecting group, alkene, alkyne, amine, carboxylic acid, halogenated aromatic, aldehyde, vinyl halide; $R_1$, $R_2$ and $R_3$ are selected from the group consisting of hydrogen, alkyl, aryl, phenoxy, methoxy, halide, methylene cyclohexyl, benzyl, heteroaryl, aryloxy, carboxyl, carboxalkyl, carboxaryl, arylalkyl, thiol and hydroxyl; L comprises a linking group; $X_4$ comprises a functional moiety selected from carboxyl, amino, gem-dialkyl, and methylene; and $X_2$ comprises a functionality containing oxygen, sulfur or carbon, having a predefined stereochemical relationship;
   and reacting, under stereo- and/or regio-chemically controlled carbon-carbon bond formation reaction conditions, said first monomer with said second monomer to yield a compound in which the monomers are attached to one another by way of the second ($L_{12}$) and third terminal ($L_{21}$) reactive moieties, such that the compound has at least one biological activity of a peptide.

2. The method of claim 1, further comprising functionalizing the compound having at least one biological activity of a peptide by chemical reaction of one or more of the functionalizable groups.

3. The method of claim 1, wherein the providing said first monomer and said second monomer comprises providing first and second monomers each having a desired stereochemistry for reacting under stereo- and/or regio-chemically controlled reaction conditions.

4. The method of claim 2, wherein the functionalizing step comprises reacting at least one functionalizable group with an amino acid.

5. The method of claim 2, further comprising converting at least one functionalizable group by reacting to attach an amino acid or peptide.

6. The method of claim 2, wherein the functionalizing step comprises reacting two or more functionalizable groups with an amino acid.

7. The method of claim 2, further comprising converting two or more functionalizable groups by reacting to attach an amino acid or peptide.

8. The method of claim 1, wherein the reacting is performed in a combinatorial synthesis manner.

9. The method of claim 1, wherein the stereo- and/or regio-chemically controlled reaction condition is an olefin metathesis carbon-carbon bond formation reaction.

10. The method of claim 1, wherein the stereo- and/or regio-chemically controlled reaction condition is an olefin metathesis reaction, a transition metal catalyzed cross-coupling reaction, a pinacol coupling reaction, a tandem aldol/Curtius rearrangement reaction, a hydrozirconation reaction, a nucleophilic addition reaction, or a Nozaki-Hiyama-Kishi coupling reaction.

11. The method of claim 1, wherein said first monomer further contains a first linking group binding site ($X_1$) and said second monomer further contains a second linking group binding site ($X_2$).

12. The method of claim 11, wherein each terminal reactive moiety is selected independently from the group consisting of hydrogen, protecting group, alkene, alkyne, amine, carboxylic acid, halogenated aromatic, aldehyde and vinyl halide; and each linking group binding site is selected independently from the group consisting of nitrogen-, oxygen-, sulfur-, and carbon-containing functionalities.

13. The method of claim 12, wherein each linking group binding site is selected independently from the group consisting of hydroxyl, amino and thiol.

14. The method of claim 12, wherein each functionalizable group is selected independently from the group consisting of hydrogen, alkyl, aryl, phenoxy, methoxy, halide, methylene, cyclohexyl, benzyl, aryloxy, heteroaryl, carboxyl, carboxalkyl, carboxaryl, arylalkyl, thio and hydroxyl.

15. The method of claim 11, further comprising reacting said first monomer and said second monomer through the first and second linking group binding sites, in the presence of a linking reagent.

16. The method of claim 15, wherein the linking reagent is selected from the group consisting of diisopropylamino chlorophosphoramidite, dimethyldichlorosilane, sulfonyl chloride, and metal reagents containing boron or titanium.

17. The method of claim 11, wherein said first and second monomers are attached to one another intermolecularly or intramolecularly using an olefin metathesis reaction to yield a compound in which the monomers are attached to one another by way of an alkenyl segment unit.

18. The method of claim 1, further comprising attaching said first monomer to a solid support though the first terminal reactive moiety or attaching said second monomer to a solid support through the fourth terminal reactive moiety.

19. The method of claim 1, wherein said first monomer and said second monomer are each independently selected from the group consisting of allylic alcohols, allylic thiols, allylic amines, homoallylic alcohols, homoallylic thiols and homoallylic amines.

20. The method of claim 11, wherein said first monomer is of the structure

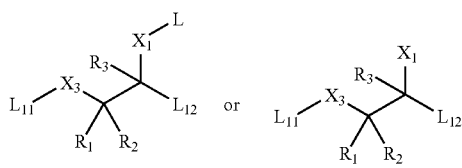

wherein:
$L_{11}$ is a terminal reactive moiety selected from the group consisting of hydrogen, protecting group, alkene, alkyne, amine, carboxylic acid, halogenated aromatic, aldehyde and vinyl halide; and each $L_{12}$ comprises an alkene;
$R_1$, $R_2$ and $R_3$ are functionalizable moieties, each selected independently from the group consisting of hydrogen, alkyl, aryl, phenoxy, methoxy, halide, methylene, cyclohexyl, benzyl, aryloxy, heteroaryl, carboxyl, carboxalkyl, carboxaryl, arylalkyl, thio and hydroxyl;
$X_3$, comprises a functionalizable moiety selected from the group consisting of carboxyl, amino, gem-dialkyl, and methylene;
$X_1$, is a linking group binding site comprising a nitrogen-, oxygen-, sulfur-, or carbon-containing functionality; and
L is a linking group.

21. The method of claim 20, wherein L is a linking group selected from the group consisting of mixed carbonates, carbamates, disulfides, silanes, ureas, acetals, ortho esters, phosphates and oxides.

22. The method of claim 20, wherein said second monomer is of the structure

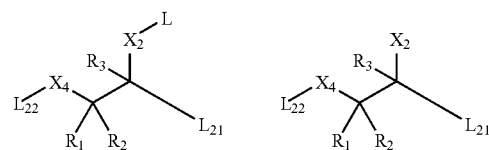

wherein:
$L_{22}$ each comprises a terminal reactive moiety selected from the group consisting of hydrogen, protecting group, alkene, alkyne, amine, carboxylic acid, halogenated aromatic, aldehyde and vinyl halide; and each $L_{21}$ comprises an alkene;
$R_1$, $R_2$, and $R_3$ are functionalizable moieties, each selected independently from the group consisting of hydrogen, alkyl, aryl, phenoxy, methoxy, halide, methylene, cyclohexyl, benzyl, aryloxy, heteroaryl, carboxyl, carboxalkyl, carboxaryl, arylalkyl, thio and hydroxyl;
$X_4$ comprises a functionalizable moiety selected from the group consisting of carboxyl, amino, gem-dialkyl, and methylene;
$X_2$ is a linking group binding site comprising a nitrogen-, oxygen-, sulfur-, or carbon-containing functionality; and
L is a linking group.

23. The method of claim 22 wherein L is a linking group selected from the group consisting of mixed carbonates, carbamates, disulfides, silanes, ureas, acetals, ortho esters, phosphates and oxides.

24. The method of claim 20 wherein the linking group binding site is a hydroxyl, amino or thiol group.

25. The method of claim 22 wherein the linking group binding site is a hydroxyl, amino or thiol group.

26. The method of claim 22, wherein the compound having at least one biological activity of a peptide is of the structure:

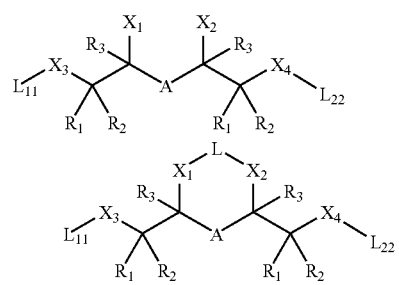

wherein A is formed from the reaction of $L_{12}$ and $L_{21}$.

* * * * *

UNITED STATES PATENT AND TRADEMARK OFFICE
CERTIFICATE OF CORRECTION

| | | |
|---|---|---|
| PATENT NO. | : 7,183,059 B2 | Page 1 of 1 |
| APPLICATION NO. | : 09/949280 | |
| DATED | : February 27, 2007 | |
| INVENTOR(S) | : Verdine et al. | |

It is certified that error appears in the above-identified patent and that said Letters Patent is hereby corrected as shown below:

In the Specification

At Column 1, Line number 13, please add the following paragraph:
GOVERNMENT FUNDING
This invention was made with government support under 9626985 awarded by the National Science Foundation. The government has certain rights in the invention.

Signed and Sealed this
Seventh Day of January, 2025

Derrick Brent
*Acting Director of the United States Patent and Trademark Office*